US012765885B2

(12) United States Patent
Orphanos et al.

(10) Patent No.: US 12,765,885 B2
(45) **Date of Patent: *Oct. 20, 2026**

(54) AUGMENT REAMER AND RELATED METHODS

(71) Applicant: DePuy Ireland Unlimited Company, Ringaskiddy (IE)

(72) Inventors: Stephen J. Orphanos, Bridgewater, MA (US); Gary Fernandes, Assonet, MA (US); Christian Amaral, South Dartmouth, MA (US); Francisco A. Amaral, Acushnet, MA (US); Raymond F. Murphy, Attleboro, MA (US); Robert Ciocca, Woonsocket, RI (US)

(73) Assignee: DePuy Ireland Unlimited Company, Ringaskiddy (IE)

( * ) Notice: Subject to any disclaimer, the term of this patent is extended or adjusted under 35 U.S.C. 154(b) by 223 days.

This patent is subject to a terminal disclaimer.

(21) Appl. No.: 18/444,435

(22) Filed: Feb. 16, 2024

(65) Prior Publication Data

US 2024/0341778 A1 Oct. 17, 2024

Related U.S. Application Data

(63) Continuation of application No. 17/547,384, filed on Dec. 10, 2021, now Pat. No. 11,925,362.

(51) Int. Cl.
*A61B 17/16* (2006.01)

(52) U.S. Cl.
CPC ................................ *A61B 17/1684* (2013.01)

(58) Field of Classification Search
CPC . A61B 17/16; A61B 17/1613; A61B 17/1615; A61B 17/1617; A61B 17/162;
(Continued)

(56) References Cited

U.S. PATENT DOCUMENTS

| | | | |
|---|---|---|---|
| 5,643,271 | A | 7/1997 | Sederholm et al. |
| 6,673,115 | B2 | 1/2004 | Resch et al. |

(Continued)

FOREIGN PATENT DOCUMENTS

| | | | |
|---|---|---|---|
| CN | 109561900 | B | 2/2022 |
| EP | 0893097 | B1 | 9/2004 |

(Continued)

OTHER PUBLICATIONS

**International Search Report and Written Opinion for Application No. PCT/IB2022/062091, issued Mar. 16, 2023, 15 pages.

*Primary Examiner* — Eric S Gibson
(74) *Attorney, Agent, or Firm* — Barnes & Thornburg LLP

(57) ABSTRACT

Reamer instruments and related methods are disclosed for use in preparing bone, such as a glenoid bone surface, to receive an implant requiring one of two or more possible surface geometries. Described reamer instruments can have a modular or multi-component design. A minimal number of components can be particular to a particular required geometry, which can allow assembly and use of reamer instruments of the present disclosure to be flexible, intuitive, and efficient. In some embodiments, a disposable reamer head assembly can be driven by a disposable drive tip through a pin-on-pin connection. The remaining components of the reamer instrument can be sterilized and re-used. To prepare bone for a half-wedge implant, a half-wedge housing can be coupled to a reamer instrument handle and a depth stop can be coupled to the housing to achieve the required geometry. Alternatively, a full-wedge housing can be coupled to the instrument handle.

16 Claims, 38 Drawing Sheets

(58) Field of Classification Search
CPC ............ A61B 17/1622; A61B 17/1624; A61B 17/1626; A61B 17/1628; A61B 17/1631; A61B 17/1633; A61B 17/1659; A61B 17/1662; A61B 17/1664; A61B 17/1666; A61B 17/1684
See application file for complete search history.

(56) References Cited

U.S. PATENT DOCUMENTS

| | | | | |
|---|---|---|---|---|
| 7,008,430 | B2 | 3/2006 | Dong et al. | |
| 7,513,899 | B2 | 4/2009 | Grim | |
| 7,670,343 | B2 | 3/2010 | Meridew et al. | |
| 7,749,227 | B2 * | 7/2010 | Lechot | A61B 17/1666 606/88 |
| 7,780,669 | B2 * | 8/2010 | Lechot | A61B 17/1633 606/86 R |
| 7,789,884 | B2 | 9/2010 | Timperley et al. | |
| 7,955,320 | B2 | 6/2011 | Desarzens et al. | |
| 8,137,359 | B2 | 3/2012 | Poncet | |
| 9,078,672 | B1 | 7/2015 | Rossé | |
| 9,668,757 | B2 | 6/2017 | Ek et al. | |
| 9,724,167 | B2 | 8/2017 | Ziaei et al. | |
| 9,737,313 | B1 | 8/2017 | Sohn et al. | |
| 9,936,960 | B2 * | 4/2018 | Weekes | A61B 17/1622 |
| 10,028,838 | B2 * | 7/2018 | Hodorek | A61F 2/4081 |
| 10,194,924 | B2 | 2/2019 | Fortin et al. | |
| 10,478,197 | B2 * | 11/2019 | Victor | A61B 17/1666 |
| 10,548,617 | B1 * | 2/2020 | Olson | A61B 17/1642 |
| 10,568,649 | B2 | 2/2020 | Roger | |
| 10,687,831 | B2 * | 6/2020 | Kovacs | A61B 17/1684 |
| 10,702,288 | B2 | 7/2020 | Young | |
| 11,234,718 | B2 * | 2/2022 | Fiedler | A61B 17/162 |
| 11,234,826 | B2 * | 2/2022 | Hodorek | A61B 17/1617 |
| 11,246,604 | B2 * | 2/2022 | Rodriguez | A61B 17/1615 |
| 11,925,362 | B2 * | 3/2024 | Orphanos | A61B 17/1659 |
| 12,016,572 | B2 * | 6/2024 | Fiedler | A61B 17/1631 |
| 12,558,109 | B2 * | 2/2026 | Fiedler | A61B 17/162 |
| 2005/0049601 | A1 * | 3/2005 | Keller | A61B 17/1666 606/81 |
| 2015/0374502 | A1 * | 12/2015 | Hodorek | A61F 2/4081 606/80 |
| 2016/0045207 | A1 * | 2/2016 | Kovacs | A61B 17/1631 606/80 |
| 2016/0175112 | A1 * | 6/2016 | Pruvost | A61B 17/1633 606/81 |
| 2018/0008293 | A1 * | 1/2018 | Kovacs | A61B 17/1659 |
| 2018/0280037 | A1 * | 10/2018 | Dassonville | A61B 17/1633 |
| 2018/0353248 | A1 | 12/2018 | Bowling et al. | |
| 2019/0231369 | A1 * | 8/2019 | Cardon | A61B 90/06 |
| 2019/0357924 | A1 * | 11/2019 | Papenfuss | A61B 17/1684 |
| 2019/0358712 | A1 * | 11/2019 | Stefan | B23B 31/003 |
| 2020/0155170 | A1 | 5/2020 | Kovacs et al. | |
| 2020/0163683 | A1 * | 5/2020 | Anderson | A61B 17/1633 |
| 2021/0267609 | A1 * | 9/2021 | Nguyen | A61B 17/1659 |
| 2021/0290255 | A1 * | 9/2021 | Fiedler | A61B 17/162 |
| 2022/0192682 | A1 * | 6/2022 | Fiedler | A61B 17/1664 |
| 2023/0132876 | A1 * | 5/2023 | Fiedler | A61B 17/162 409/211 |
| 2023/0181199 | A1 * | 6/2023 | Orphanos | A61B 17/1659 606/80 |
| 2024/0341778 | A1 * | 10/2024 | Orphanos | A61B 17/1684 |

FOREIGN PATENT DOCUMENTS

| | | | | |
|---|---|---|---|---|
| EP | 3023063 | B1 | 8/2017 | |
| FR | 3028169 | B1 | 2/2020 | |
| WO | 2018009780 | A1 | 1/2018 | |
| WO | 2020056419 | A1 | 3/2020 | |
| WO | WO-2023105504 | A1 * | 6/2023 | A61B 17/1684 |

* cited by examiner

AUGMENT REAMER AND RELATED METHODS

CROSS REFERENCE TO RELATED APPLICATION

The present application is a continuation of and claims priority to U.S. patent application Ser. No. 17/547,384, filed Dec. 10, 2021, entitled "Augment Reamer and Related Methods," the content of which is hereby incorporated by reference herein in its entirety.

FIELD

The present disclosure relates to systems, devices, and methods for preparing a bone surface to accept a surgical implant, and more particular relates to preparing a glenoid bone surface in the shoulder to receive a metaglene implant.

BACKGROUND

Many surgical procedures require preparation of a bone surface to receive an implant. One non-limiting location in the body where this can be required is the shoulder. Patients may suffer from disease or trauma to that region, necessitating the performance of a shoulder procedure, such as a total shoulder replacement, to relieve the patient from pain and incapacity. In a total shoulder replacement procedure, a humeral prosthesis is used to replace the natural head of the patient's humerus. The humeral prosthesis typically includes an elongated post component that is implanted into the intramedullary canal of the patient's humerus and a hemispherically-shaped prosthetic head component that is secured to the post component. In such a total shoulder replacement procedure, the natural glenoid surface of the scapula is typically resurfaced or otherwise replaced with a glenoid component that provides a bearing surface upon which the prosthetic head component of the humeral prosthesis articulates.

However, in some cases the patient's natural shoulder, including its soft tissue, has degenerated to a severe degree of joint instability and pain. In many such cases, it can be necessary to change the mechanics of the shoulder. Reverse shoulder implants can be used to do so. As its name suggests, a reverse shoulder implant reverses the anatomy, or structure, of the healthy shoulder. In particular, a reverse shoulder implant is designed such that the prosthetic head (i.e., the "ball" in the ball-and-socket joint), known as a glenosphere component, among other names, is secured to the patient's scapula, with the corresponding concave bearing (i.e., the "socket" in the ball-and-socket joint), known as a humeral cup, among other names, being secured to the patient's humerus. Such a reverse configuration allows the patient's deltoid muscle, which is one of the larger and stronger shoulder muscles, to raise the arm.

During a reverse shoulder procedure, a glenoid bone can be prepared using a power driven bone reamer for fitment with a shoulder implant. Various shoulder implants may have different geometries. This can vary, for example, based on the anatomy of the patient, the shoulder being treated (e.g., left shoulder vs. right shoulder), the anatomical bone preparation location (e.g., superior vs. posterior), the intended future use of the implant by the patient, the handedness of the surgeon (e.g., left-handed vs. right-handed), and/or other preferences of the surgeon, among other factors. Multiple types of implants may be able to be used with the same patient, and the determination as to which implant is best may not be made until after the surgical procedure begins, e.g., after the surgeon has assessed the bone surfaces internally as part of the procedure. The type, size, and shape of the implant, however, can impact how the bone surface must be prepared. Current reamers, however, lack in providing surgeons the ability to easily adapt to use the same tools for different anatomies or bone preparation changes that may arise. For example, existing glenoid reamers typically operate over a guidewire and are only able to use a cutting head having a single axis of rotation that is not easily adjustable to a different axis of rotation. Further, because it may be desirable to use multiple cutting head configurations and/or one or more single cutting heads that have multiple configurations (e.g., different axes of rotation that can be used) with a single base tool, glenoid reamers should be more adaptable and allow for more interchangeability than they currently do. Providing for a single base tool can allow some components to be disposed of after a single use other components can be sterilized and reused. Existing reamers are often complicated and/or difficult to assemble and disassemble while still providing for consistent use.

Accordingly, there is a need for a reamer that can prepare bone with a precise known geometry that can be selected based on particular needs of the patient and surgery in a robust manner that is intuitive to the surgeon, nurses, back table staff, etc. The reamer should be flexible, adaptable, intuitive, and provide for a high level of precision and performance.

SUMMARY

The systems, devices, and methods described herein generally relate to preparing a bone surface to receive an implant and, more particularly, can be used to prepare a glenoid to receive an implant. Reamers of the present disclosure can have a modular or multi-component design and can be assembled to prepare bone for one of two (or more) different implant geometry angles. Assembly and disassembly of the reamer instruments can be intuitive to a user, with a flexible system that can allow for assembly adjustment based, at least in part, on one or more of patient positioning, anatomical bone preparation location (superior, posterior, left shoulder, right shoulder, etc.), and surgeon preference, e.g., for right or left handed operation of the reamer. For example, a simplified method can be used to attach, remove, and/or secure a reamer bone cutting head to the instrument via a locking collar, as discussed in detail below. The components of reamer instruments disclosed herein and methods of assembly and use of the same can be flexible and easily adapted for use depending upon the requirements of the particular surgical procedure. Reamer instrument of the present disclosure can provide an elegant way to transfer rotation and torque from a drive shaft to a rotating reamer cutting head across two or more different axis of rotation.

One embodiment of an instrument for reaming bone in accordance with the present application includes an elongate body having a proximal end, a distal end, and an inner throughbore extending therebetween, a drive shaft, and a reamer head. The drive shaft has a proximal end to couple to a power source and a distal end with a plurality of engagement pins. The drive shaft extends through the inner throughbore of the elongate body such that the plurality of engagement pins on the distal end of the drive shaft extend distal of the distal end of the elongate body. The reamer head is removably coupled to the distal end of the elongate body.

Further, the reamer head has a body with a distal facing cutting surface to cut bone and at least one engagement aperture extending through at least a portion of the body. A plurality of engagement posts are associated with the at least one engagement aperture. The plurality of engagement pins of the drive shaft couple with the plurality of engagement posts of the reamer head such that rotation of the drive shaft causes rotation of the reamer head.

The devices and methods described herein can have a number of additional features and/or variations, all of which are within the scope of the present disclosure. For example, the reamer instrument can further include a locking collar that can rotate relative to the elongate body to releasably secure the reamer head to the distal end of the elongate body. The distal end of the elongate body can have a plurality of ball bearings. The ball bearing can slide along a ramp on an inner surface of the locking collar when the locking collar rotates relative to the elongate body.

In some embodiments, the plurality of engagement pins can include a first engagement pin and a second engagement and the plurality of engagement posts can include a first engagement post and a second engagement post. The first engagement pin can abut the first engagement post and the second engagement pin can abut the second engagement post such that rotational motion of the drive shaft can cause rotational motion of the reamer head. A central longitudinal axis of the drive shaft can extend at an oblique angle relative to a central longitudinal axis of the engagement aperture when the plurality of engagement pins of the drive shaft are coupled with the plurality of engagement posts of the reamer head. In some embodiments, the at least one engagement aperture of the reamer head can extend from a proximal-facing surface of the body through the distal-facing surface of the body. The plurality of engagement posts can extend along a longitudinal axis of the engagement aperture. The plurality of engagement pins can extend substantially perpendicular to the central longitudinal axis of the drive shaft. The plurality of engagement pins can be circumferentially spaced apart around a distal tip of the drive shaft.

The drive shaft can include an elongate shaft portion and a distal drive tip. The distal drive tip can selectively couple to a distal end of the elongate shaft portion. In some embodiments, the drive shaft can be cannulated from the proximal end of the drive shaft to the distal end of the drive shaft. In other embodiments, a distal end of the drive shaft can be closed. The elongate body of the instrument can include a handle and a housing. The handle can have an inner throughbore extending therethrough and the housing can have an inner throughbore extending therethrough. The housing can be removably coupled to the handle such that the inner throughbore of the handle aligns with the inner throughbore of the housing.

Another embodiment of an instrument for reaming bone in accordance with the present disclosure includes a reamer head having a distal-facing cutting surface to cut bone, a depth-stop, an elongate body, and a drive shaft. The depth stop has a body with an inner surface, an outer surface, and a pair of spaced apart arms. The elongate body has a proximal end, a distal end to selectively couple to the reamer head, an inner throughbore extending from the proximal end to the distal end of the elongate body, and a recessed portion to couple with the depth-stop. The drive shaft extends through the inner throughbore of the elongate body and selectively couples to the reamer head such that rotation of the drive shaft causes rotation of the reamer head. The reamer head couples to the distal end of the elongate body such that a longitudinal axis of the reamer head extends at an oblique angle relative to a longitudinal axis of the inner throughbore of the elongate body. The arms of the depth-stop contact an outer surface of the elongate body and mate with the recessed portion of the elongate body such that at least a portion of the depth-stop body inner surface opposes the distally-facing cutting surface of the reamer head.

In some embodiments, the depth-stop can include a guide pin extending distally from the outer surface of the depth-stop body. The guide pin can extend substantially parallel to the longitudinal axis of the inner throughbore of the elongate body when the arms of the depth stop mate with the recessed portion of the elongate body. The pair of spaced apart arms can form a substantially U-shape. The pair of spaced apart arms can mate with the recessed portion of the elongate body by way of a snap-fit connection.

The body of the depth-stop can include a spherical shape and the pair of spaced apart arms can extend from a proximal end thereof. In some embodiments, a longitudinal axis extending from the proximal end to the distal end of the depth-stop, substantially through the guide pin, can be substantially perpendicular to a longitudinal axis extending substantially parallel to the pair of spaced apart arms of the depth stop.

The elongate body can include a handle and a housing. The handle can have an inner throughbore extending therethrough and the housing can have an inner throughbore extending therethrough. The housing can be removably coupled to the handle such that the inner throughbore of the handle aligns with the inner throughbore of the housing. The recess portion of the elongate body can be formed on the housing. In some such embodiments, the housing can have a tubular body and the recessed portion can include a first cutaway in the tubular body and a second cutaway formed in the tubular body. The first cutaway and the second cutaway can be formed approximately 180 degrees apart from one another on the tubular body. The first and second cutaway can form a first and second planar portion in the tubular body of the housing. The pair of spaced apart arms of the depth stop can each have an inner surface that can mate with a snap-fit connection to one of the first and second planar portions in the tubular body of the housing.

In another embodiment of an instrument for reaming bone in accordance with the present disclosure, the instrument includes a handle, a reamer head with a distal-facing cutting surface to cut bone, a housing, and a drive shaft. The handle has a proximal end, a distal end, an inner throughbore extending therebetween, and a release collar. The release collar is slidably disposed along the distal end of the handle. The housing has an elongate shaft with a proximal end, a distal end, an inner throughbore extending therebetween, and a reamer attachment component formed at the distal end of the housing. The reamer attachment component removably couples the housing to the reamer head. The reamer attachment component has an opening with a longitudinal axis that extends at an oblique angle relative to the inner throughbore of the elongate shaft. The drive shaft has a proximal end that couples to a power source and a distal end. The drive shaft extends through the inner throughbore of the handle and the inner throughbore of the housing such that the distal end of the drive shaft is located within the opening of the reamer attachment component. The release collar receives the proximal end of the housing and selectively locks the housing relative to the handle in one of a plurality of positions. Each of the plurality of positions corresponds to a different rotational orientation of the housing around a longitudinal axis of the handle.

In some embodiments, the release collar can be movable between a first position in which rotational movement of the housing relative to the handle is locked and a second position in which the housing is rotatable relative to the handle. The release collar can be located closer to the proximal end of the handle in the second position that it is in the first position. In some embodiments, the release collar can include a compression element that can be compressed to move the release collar from the first position to the second position.

The plurality of positions of the housing relative to the handle can represent approximately 90-degree rotational increments of the housing around the longitudinal axis of the handle. The proximal end of the housing can have a plurality of first engagement features and the release collar can have a plurality of second engagement features. At least one of the plurality of first engagement features and the plurality of second engagement features can selectively engage the other in one of the plurality of positions. In some embodiments, the first engagement features can be female engagement features formed in the proximal end of the housing and the second engagement features can be male engagement features. In some embodiments, the reamer attachment component can extend at an angle relative to a central longitudinal axis of the elongate shaft.

In another embodiment of an instrument for reaming bone in accordance with the present disclosure, the instrument includes a handle, a housing, a reamer head, and a flexible drive shaft. The handle has a proximal end, a distal end, and a throughbore extending therebetween. The housing has a proximal end coupled to the handle, a distal end, and a throughbore extending therebetween. The reamer head has a distal-facing surface to cut bone and an engagement aperture and couples to the distal end of the housing. The flexible drive shaft has a proximal end that couples to a power source and a distal end that couples to the reamer head to drive the reamer head. The distal end of the drive shaft is able to be placed in a non-linear alignment relative to the proximal end of the drive shaft such that the drive shaft extends through the inner throughbore of the handle and the housing in a non-linear manner.

In some embodiments, the drive shaft is a solid drive shaft devoid of a cannulation extending through any significant portion of its length. A central longitudinal axis of the engagement aperture of the reamer head can axially align with a central longitudinal axis of the distal end of the drive shaft when the drive shaft is coupled to the reamer head. The distal end of the drive shaft can include an engagement feature that is complimentary to the engagement aperture of the reamer head. In some such embodiments, the engagement feature at the distal end of the flexible drive shaft can be a male hexagonal drive feature and the engagement aperture of the reamer head can be a female hexagonal aperture. The female hexagonal aperture can receive the male hexagonal drive feature such that rotation of the drive shaft can cause rotation of the reamer head. In some embodiments, the instrument can further include a depth stop having a body and a guide pin. The guide pin can extend distally from the body. The depth stop can couple to the housing such that at least a portion of the body and the guide pin are located distal of at least a portion of the distal cutting surface of the reamer head to prevent said portion of the distal cutting surface from cutting bone.

One embodiment of a method of assembling a surgical reamer in accordance with the present disclosure includes coupling a proximal end of a drive shaft to a distal end of a handle and coupling a proximal end of a housing attachment to the distal end of the handle such that the drive shaft extends through an inner throughbore of the housing attachment. The method further includes coupling a reamer head to a distal end of the housing and releasably locking the reamer head to the distal end of the housing such that a cutting surface of the reamer head extends distally from the housing.

In some embodiments, coupling the proximal end of the housing attachment to the distal end of the handle can include inserting the proximal end of the housing attachment into a release collar that is slidably disposed along the distal end of the handle and orienting the housing relative to the handle in one of a plurality of positions. Each of the plurality of positions can correspond to a different rotational orientation of the housing around a longitudinal axis of the handle. In some such embodiments, the plurality of positions can correspond to rotation orientations of the housing relative to the longitudinal axis of the handle at 90-degree intervals.

The method can further include assembling the drive shaft by coupling a disposable drive pin drive tip to a distal end of an elongate shaft. Coupling the reamer head to the distal end of the housing can further include placing a locking collar at the distal end of the housing in an unlocked position and inserting the reamer head into the distal end of the housing. In some such embodiments, releasably locking the reamer head to the distal end of the housing can further include placing the locking collar in a locked position. The method can include coupling a depth stop to a recessed portion formed in the housing such that at least a portion of the depth stop opposes the cutting surface of the reamer head. In at least some embodiments the method can include coupling at least one of a drill connection or an electrical connection to the handle to enable driving the drive shaft under power. The drill connection can include, for example, a Hudson connection.

Any of the features or variations described above can be applied to any particular aspect or embodiment of the present disclosure in a number of different combinations. The absence of explicit recitation of any particular combination is due solely to the avoidance of repetition in this summary. By way of non-limiting example, the first engagement features can be detents formed in the proximal end of the housing and the second engagement features can be ball bearings held within the release collar. The ball bearings can be received within the detents in the proximal end of the housing. Further, the present disclosure is also directed to use of the various embodiments of instruments for reaming bone disclosed herein. A person skilled in the art, in view of the present disclosures, will understand how to perform various surgical procedures using the various instruments disclosed herein or otherwise derivable from the present disclosures.

BRIEF DESCRIPTION OF DRAWINGS

This disclosure will be more fully understood from the following detailed description taken in conjunction with the accompanying drawings, in which.

DETAILED DESCRIPTION

Figure 1:
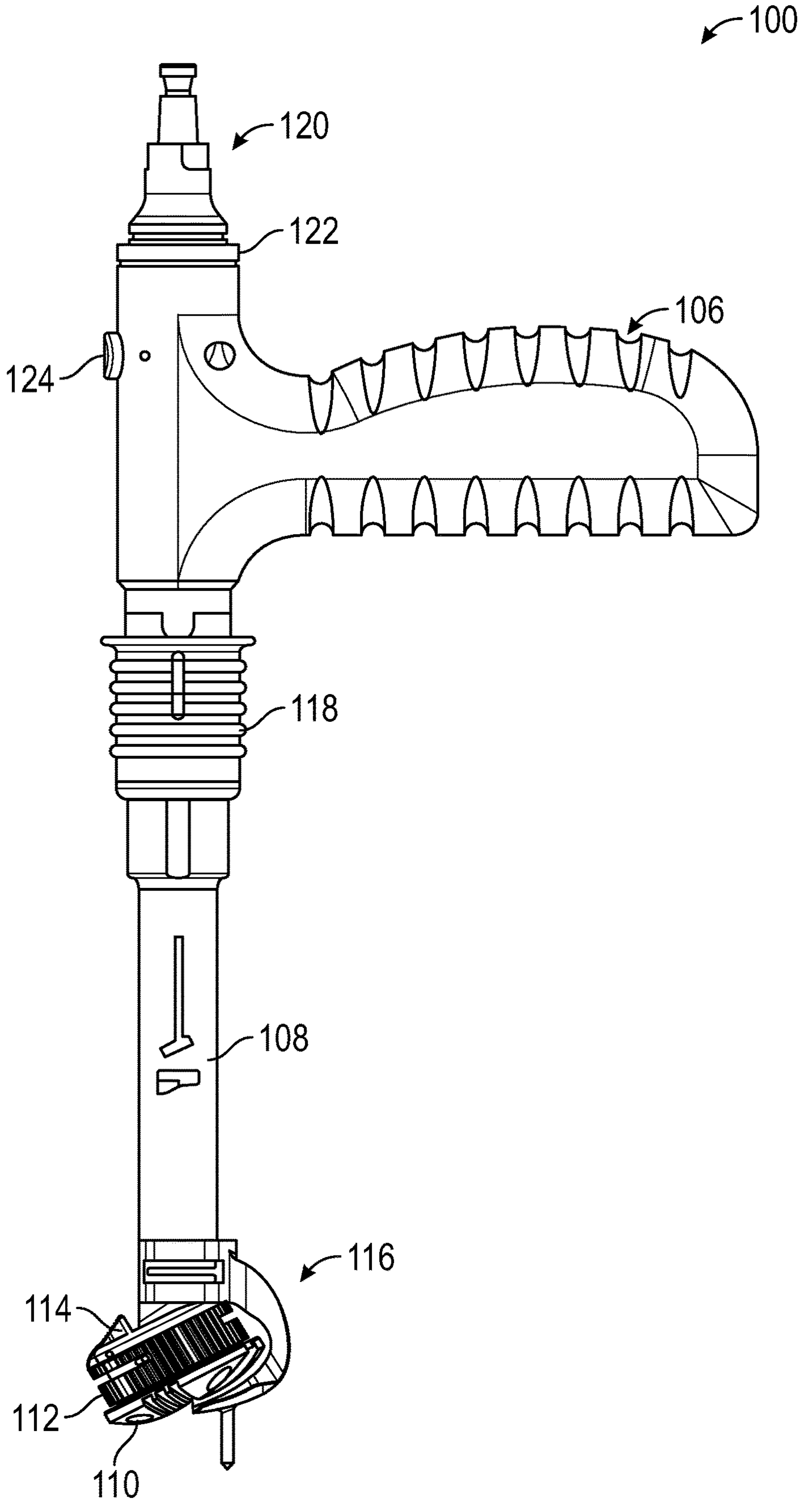
FIG. 1 is a side view of one embodiment of a reamer instrument with a half-wedge housing in accordance with the present disclosure.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure. Like-numbered components across embodiments generally have similar features unless otherwise stated or a person skilled in the art would appreciate differences based on the present disclosure and his/her knowledge. Accordingly, aspects and features of every embodiment may not be described with respect to each embodiment, but those aspects and features are applicable to the various embodiments unless statements or understandings are to the contrary.

The figures provided herein are not necessarily to scale, although a person skilled in the art will recognize instances where the figures are to scale and/or what a typical size is when the drawings are not to scale. While in some embodiments movement of one component is described with respect to another, a person skilled in the art will recognize that other movements are possible. To the extent features or steps are described herein as being a "first feature" or "first step," or a "second feature" or "second step," such numerical ordering is generally arbitrary, and thus such numbering can be interchangeable. Moreover, a person skilled in the art will appreciate that not all of the method steps disclosed herein are required, and, in view of the present disclosure, will understand how modifications can be made to each step, the order of the steps, the limitation of certain steps, etc. without departing from the spirit of the present disclosure while still achieve the desired goals. Additionally, a number of terms may be used throughout the disclosure interchangeably but will be understood by a person skilled in the art.

The present disclosure relates to systems, devices, and methods for preparing a bone surface to accept an implant. More particularly, embodiments of modular reamer instruments are disclosed herein that can be used to prepare a bone surface, such as a shoulder in the case of a glenoid deformity, to accept one of two (or more) wedged implants. In other words, the present disclosure provides systems, methods, and devices that can simplify a surgical procedure as it pertains to preparing a bone surface to reflect a desired geometry for receiving a particular implant. As discussed in detail herein, one of two housings-a half-wedge housing or a full-wedge housing—can be selected during assembly of a reamer instrument based on particular needs of a surgery and/or patient. In this manner, assembly and operation of the reamer instrument can be streamlined regardless of the geometry of the implant. A reamer instrument with the half-wedge housing can also include a depth stop that can be used to prepare a bone surface to accept a half-wedge implant, such as a half-wedge metaglene implant. A reamer instrument with the full-wedge housing can be used to prepare a bone surface to accept a full-wedge implant, such as a full-wedge metaglene implant, that has a distinct angulation from the half-wedge implant. Other embodiments of half-wedge and full-wedge housings beyond those disclosed herein, as well as other housings more generally, can be used in conjunction with the reamer instruments provided for herein and/or otherwise derivable from the present disclosures.

Figure 2:
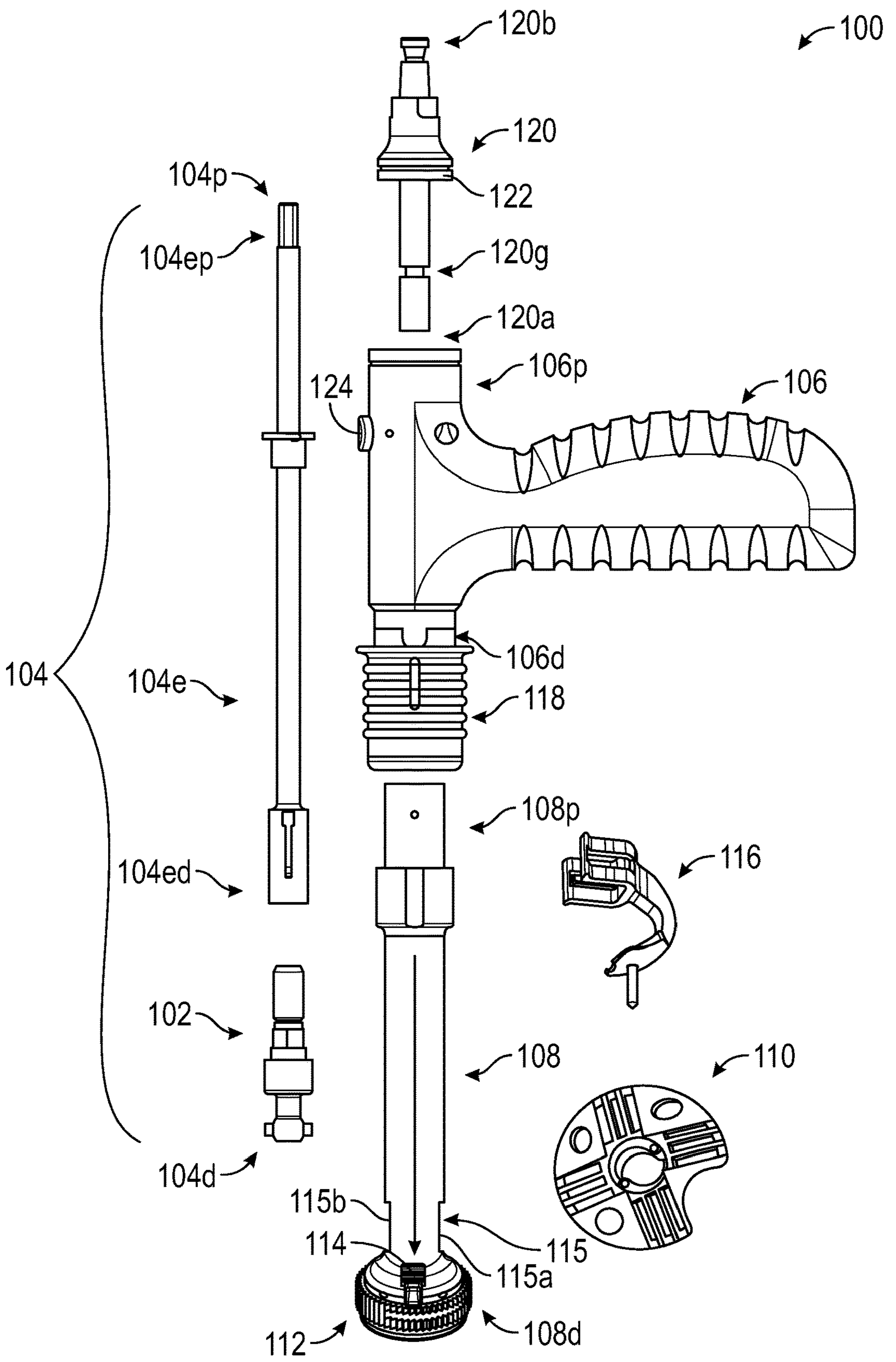
FIG. 2 is an exploded view of the reamer instrument of FIG. 1.

FIGS. 1 and 2 illustrate one embodiment of an augment reamer 100 of the present disclosure with components for use in preparing bone to accept an implant with a first geometry, referred to herein as a half-wedge metaglene implant or a half-wedge implant. FIG. 1 shows the augment reamer 100 (also referred to as a reamer herein) in an assembled configuration, while FIG. 2 shows the augment reamer 100 of FIG. 1 in an exploded view. With reference to FIGS. 1 and 2, the reamer 100 can include a drive shaft 104 coupled to a handle 106 and a power source (not shown). The drive shaft 104 can include a drive tip 102 and an elongate shaft 104*c*. In some embodiments, the drive tip 102 can be removably coupled to a distal end 104*de* of the elongate shaft such that the drive tip can be disposed of after a surgical procedure while the elongate shaft 104*e*, as well as other components of the reamer instrument 100, may be sterilized and reused. The drive shaft 104 can extend through a housing 108 such that a portion of the drive tip 102 can contact and drive a reamer head 110 coupled to a distal end 108*d* of the housing 108. In some embodiments, the drive tip 102 and the reamer head 110 can be single-use while the other components of the reamer 100 can be reusable. In this manner, the drive tip 102 and the reamer head 110 can be disposed of after a single surgical procedure, while the remaining components of the reamer 100 can be sterilized and reused in a subsequent operation.

Figure 15:
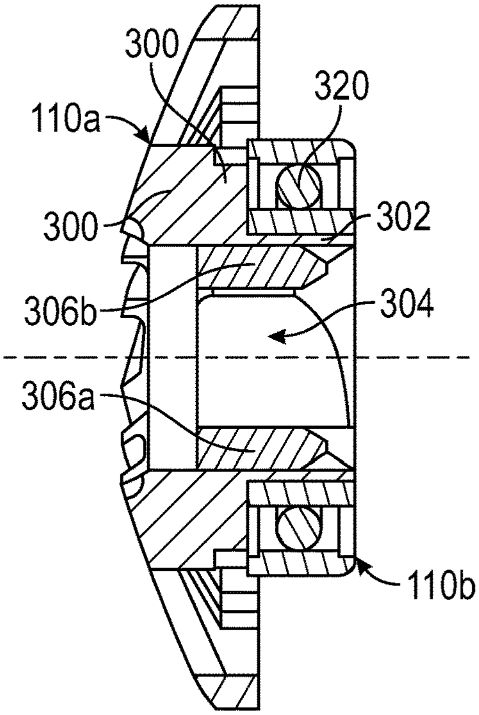
FIG. 15 is a cross-sectional view of the reamer head taken along the line A-A of FIG. 14.
Figure 16:
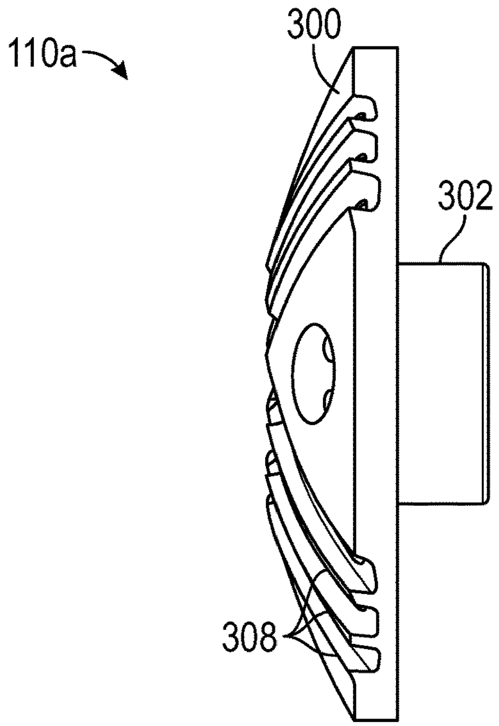
FIG. 16 is a side view of the reamer head of FIG. 14.
Figure 17:
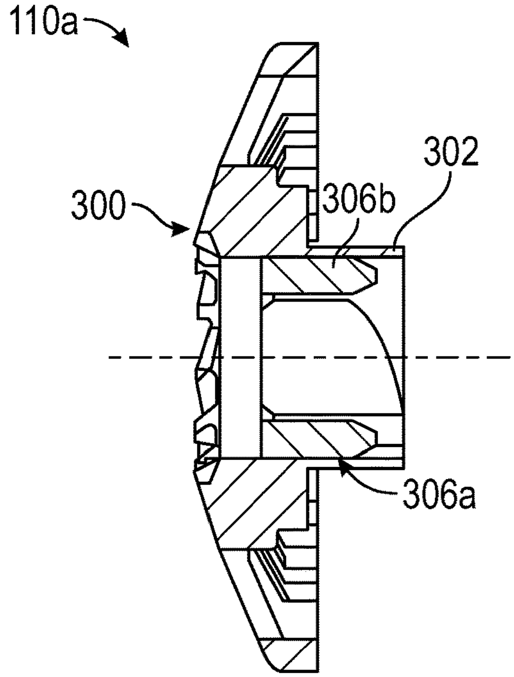
FIG. 17 is a cross-sectional view of the reamer head taken along the line A-A of FIG. 14.
Figure 18:
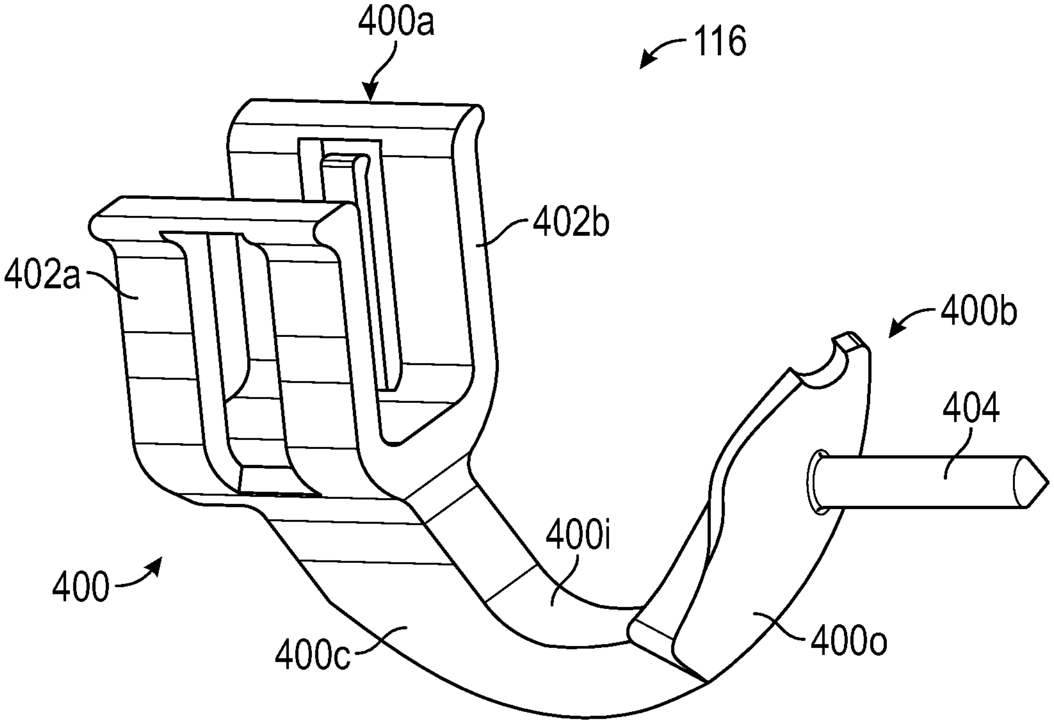
FIG. 18 is a perspective view of a depth stop of the instrument of FIG. 1.
Figure 19:
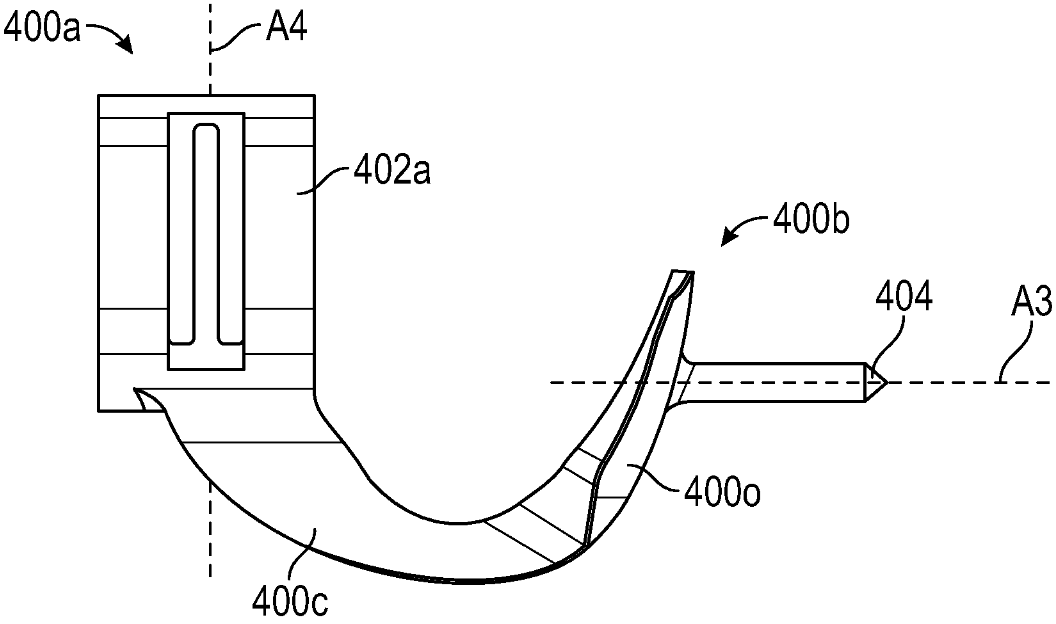
FIG. 19 is a side view of the depth stop of FIG. 18.
Figure 20:
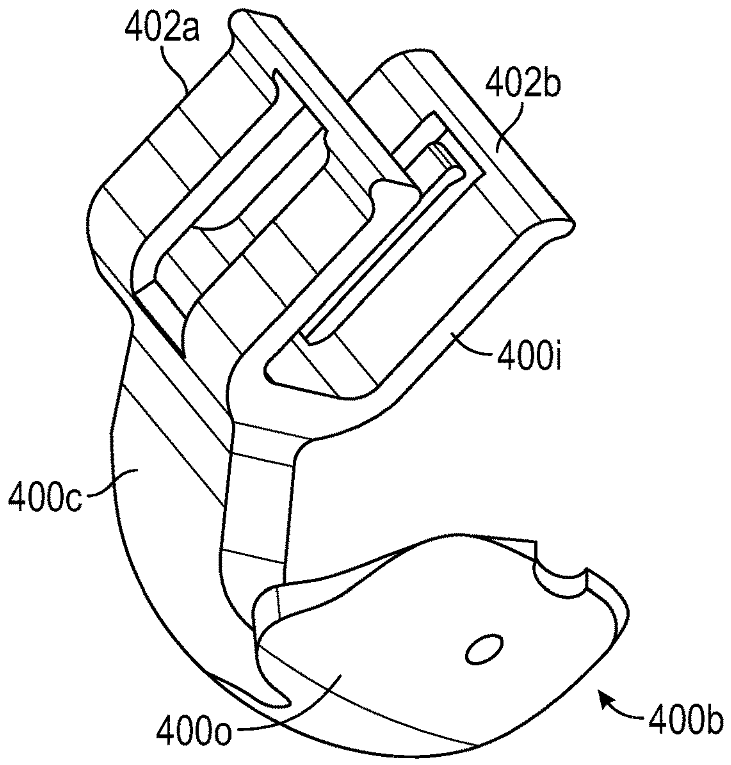
FIG. 20 is a perspective view of a depth stop body of the depth stop of FIG. 18.
Figure 21:
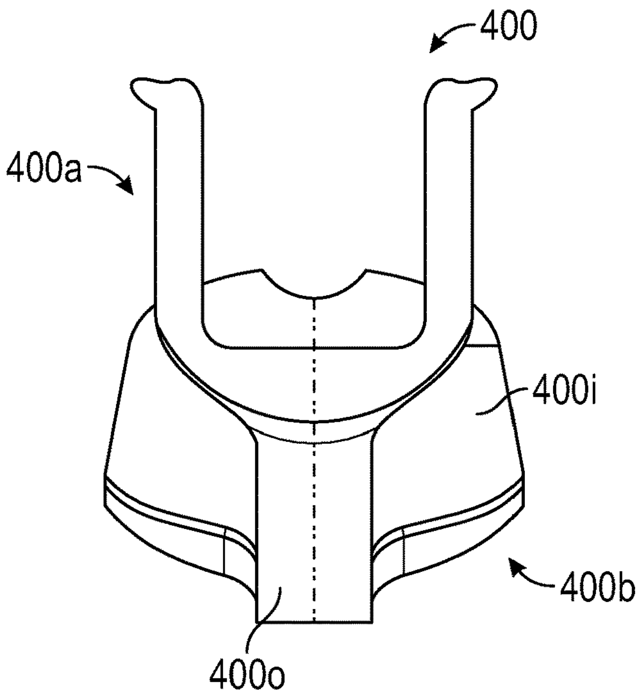
FIG. 21 is a back view of the depth stop of FIG. 18.

A locking collar 112 can be located at the distal end 108*d* of the housing 108 and can selectively couple and secure the reamer head 110 to the housing 108. For example, a locking lever 114 can be released to place the locking collar 112 in an unlocked position to permit rotation of the locking collar 112 relative to the housing 108. In the embodiment of FIGS. 1 and 2, the housing 108 can be a half-wedge housing that, as discussed in further detail below, can be used to drive the reamer head 110 to ream or cut bone at an angle that corresponds to a half-wedge metaglene implant. A depth stop 116 can be coupled to the half-wedge housing 108, e.g., in a pre-machined location on the housing, such that, during use, a portion of the depth stop 116 can extend between a portion of the reamer head 110 and the bone surface to prevent the reamer head 110 from cutting into bone at that location. For example, a depth stop attachment 115 can be pre-machined into the housing 108 such that, with the depth stop 116 coupled to the housing 108 at the depth stop attachment 115, the portion of the reamer head 110 that cuts or reams the bone surface during use results in angulation of the bone surface in a manner complementary to the angulation of the half-wedge implant. As discussed in detail below, in other instances, an alternative housing 108' can be used in place of the half-wedge housing 108 and/or without a depth stop 116 such that the reamer instrument 100 can prepare bone to receive an implant with an alternative angulation to that of the half-wedge implant, for example, a full-wedge implant. The alternative housing 108' (also referred to herein as the full-wedge housing) is discussed in detail below in connection with FIGS. 15-17.

A proximal end 108*p* of the housing 108 can be coupled to the handle 106. In some embodiments, the handle 106 can include a quick release collar 118 that can facilitate removable coupling of the drive shaft 104 and/or the housing 108 to a distal end 106*d* of the handle 106. A drill connection 120, or other electrical connection, can couple the reamer 100 to a power source (not shown) to selectively drive the drive shaft 104, which can thereby cause the drive tip 102 to rotate the reamer head 110 to ream or cut bone. For example, a first end 120*a* of the drill connection 120 can be inserted into or otherwise securely coupled to the proximal end 106*p* of the handle 106. A second end 120*b* of the drill connection 120 can be removably coupled to the power source. By way of non-limiting example, the drill connection 120 can be a Hudson connection. A washer 122 of the drill connection 120 can act as a bearing surface against the proximal end 106*p* of the handle 106 when the power source rotates the drive shaft 104, i.e., during a reaming procedure. In some embodiments, washer 122 can be integrated with the drill connection 120 and, while not removable from the drill connection, can float a small distance along the drill connection and can rotate freely. The washer 122 can be made of a PEEK material or other high-performance plastic material with similar properties. The drill connection 120 can be removed from the handle 106 for purposes of cleaning and/or storage. A button 124 on the handle 106 can be depressed to release the drill connection 120 and permit removal thereof from the handle. Alternative mechanisms to the button 124, such as a lever, switch, etc., may be used to selectively lock and unlock the drill connection 120 and the handle 106. Each of the components introduced above will be described in further detail below.

Figure 3:
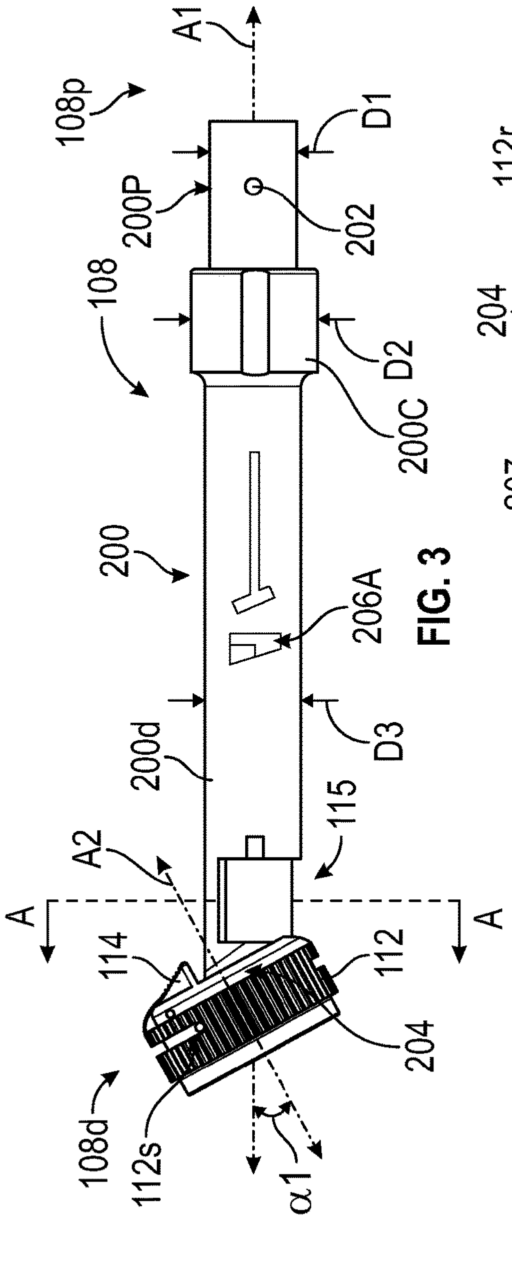
FIG. 3 is a side view of the half-wedge housing and a locking collar of the instrument of FIG. 1.
Figure 4:
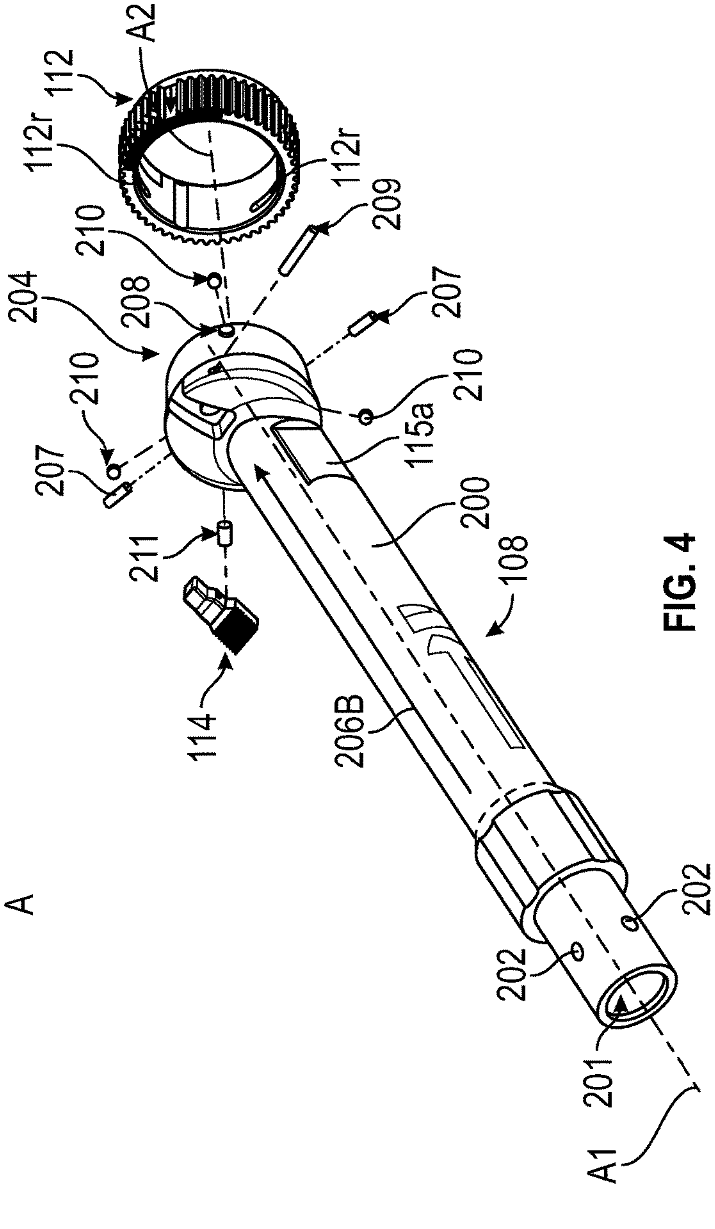
FIG. 4 is an exploded view of the half-wedge housing and the locking collar of FIG. 3.

FIGS. 3 and 4 illustrate the half-wedge housing 108 with the locking collar 112 and lever 114 at the distal end 108*d* thereof. The housing 108 can include an elongate body 200 with an inner lumen or throughbore 201 that can extend from a proximal end 200*p* of the elongate body to a distal end 200*d* of the elongate body 200 along a longitudinal axis A1. The elongate body 200 can a collar portion 200*c* located between the proximal and distal ends 200*p*, 200*d* of the elongate body and closer to the proximal end 200*p* than the distal end 200*d*. An outer diameter D1 of the proximal portion 200*p* can be smaller than an outer diameter D2 of the collar portion 200*c*. In some embodiments, the distal portion 200*d* of the elongate body 200 can have an outer diameter D3 that can be smaller than the outer diameter D2 of the collar portion 200*c* but greater than or equal to the outer diameter D1 of the proximal portion 200*p*. The proximal portion 200*p* of the elongate body 200, in other words the proximal end 108*p* of the housing 108, can be sized to be received within the distal end 106*d* of the handle 106. The proximal portion 200*p* of the elongate body 200 can include one or more detents 202 or other connection features that can facilitate selective coupling with the handle 106, as described in detail below. In the illustrated embodiments, the housing 108 can have four detents 202 spaced uniformly around a circumference of the housing, however a greater or fewer number of detents 202 can be uniformly or unevenly spaced around the housing.

The depth stop attachment location 115 can be formed in the elongate body 200 of the housing 108 at a location that can secure the depth stop 116 to the housing 108 in a manner that can allow the depth stop 116 to block at least a portion of the reamer head 110 from contacting a bone surface, i.e., can prevent the reamer head 110 from cutting into bone at a particular location. This designed coupling orientation between the depth stop 116 and the reamer head 110 can ensure that the reamer instrument 100 reams a bone surface into a known and predictable geometry. In some embodiments, the depth stop attachment 115 can be a recessed portion or cutaway portion formed in the elongate body 200 of the housing. For example, a pair of cutaways 115*a*, 115*b* can be machined into the distal end 200*d* of the elongate body 200. Each cutaway 115*a*, 115*b* can have a complementary geometry and size to a corresponding connection feature of the depth stop 116. For example, the depth stop can have first and second arms 400*a*, 400*b* that can each have a substantially rectangular planar face. The first and second cutaways 115*a*, 115*b* can have a complementary rectangular planar face into which the first and second arms 400*a*, 400*b* of the depth stop 116 can be inserted and retained therein, for example by way of a snap-fit connection. One skilled in the art will appreciate that alternative coupling features can be machined or otherwise present on the housing 108 such that the depth stop 116 can be securely coupled at a designed or known location (e.g., bolted on connection, threaded connection, etc.). In the illustrated embodiment, the first and second cutaways 115*a*, 115*b* can be formed approximately 180 degrees away from one another around the circumference of the elongate body 200.

A reamer attachment portion 204 can extend from the distal portion 200*d* of the elongate body 200. In the illustrated embodiment, the reamer attachment portion 204 can have a substantially cylindrical shape with a bore 203 formed therein. A central axis A2 of the reamer attachment portion 204, i.e., an axis that extends longitudinally through the bore 203 and intersects a top portion 204*a* of the reamer, can extend at an oblique angle $\alpha$1 relative to the longitudinal axis A1 of the elongate shaft 200. The angle $\alpha$1 at which the reamer attachment portion 204 extends can, at least in part, define an angle at which the reamer head 110 cuts or reams a bone surface during use. The angle $\alpha$1 can be selected, for example, to match a curvature of a surface of an implant intended to contact bone upon implantation. The reamer attachment portions 204, 204' of the half-wedge housing 108 and the full-wedge housing 108' (see FIG. 31) can extend at different angles $\alpha$1, $\alpha$1'. All other components of a reamer instrument of the present disclosure can remain the same for a surgery, irrespective of whether a metaglene implant is a half-wedge or a full-wedge. In this manner, a user can select which housing 108, 108' to use and couple to the handle 106 as required or preferred for a particular operation based, at least in part, on the geometry of the implant, the anatomy of the patient, and/or the preferences of the surgeon. The user(s) can then proceed with assembly and use of a reamer instrument of the present disclosure.

The housing 108 can have one or more visual indicators 206A, 206B that can signal to a user that the housing 108 is for preparing a bone surface to receive a half-wedge implant. For example, a first visual indicator 206A can be a schematic rendering of a half-wedge implant and can represent a direction of the angular cut that will be made by a reamer head 110 attached to the housing 108. By way of further example, a second visual 206B can additionally or alternatively be present on an outer surface of the housing 108 and can be an arrow that can extend longitudinally along a length of the elongate body 200 that can indicate to the user a maximum angle location and a position and/or orientation where maximum bone removal will occur by a reamer head 110. Other visual indicators can be provided in addition to or in lieu of the indicators 206A, 206B.

Figure 5:
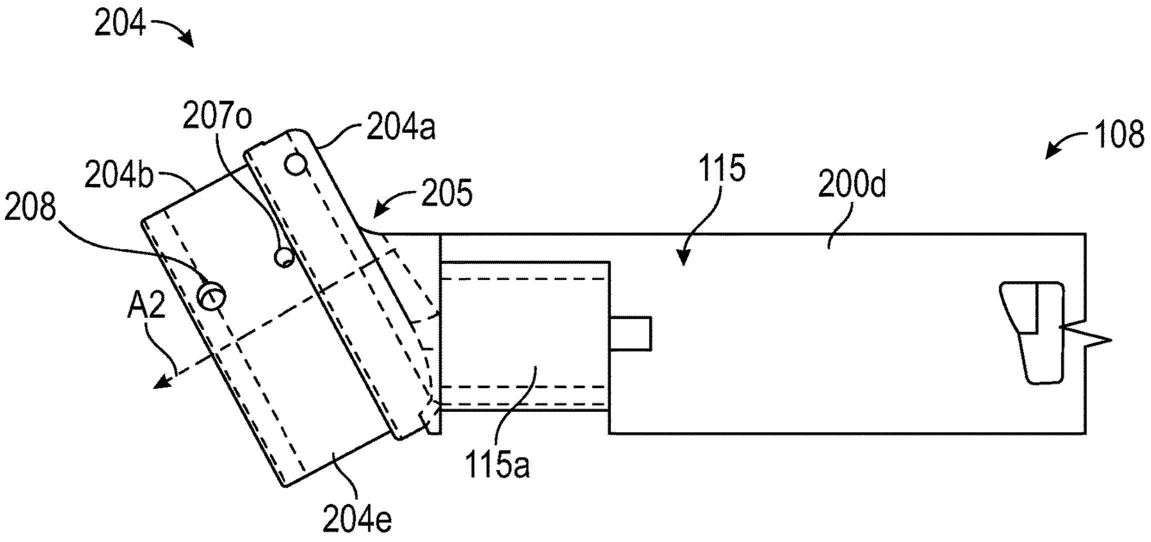
FIG. 5 is an enlarged view of a distal portion of the half-wedge housing of the instrument of FIG. 1.
Figure 6:
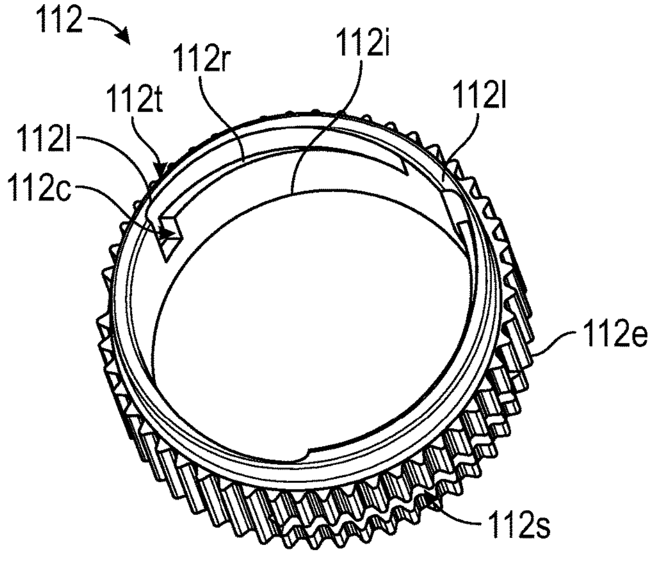
FIG. 6 is a perspective view of the locking collar of FIG. 3.
Figure 7:
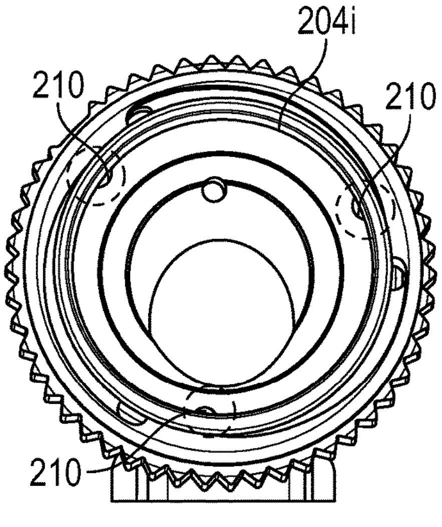
FIG. 7 is a bottom-up view of the distal end of the half-wedge housing and the locking collar of FIG. 3.

FIGS. 4 and 5 provided further details related to the reamer attachment 204. A top portion 204*a* of the reamer attachment 204 can extend at an oblique angle from the distal end 200*d* of the elongate body 200. A fillet 205 can be formed between the distal end 200*d* of the elongate body 200 and the top portion 204*a* to transition from the elongate body to the obliquely angled reamer attachment 204. A hollow cylindrical body 204*b* can extend distally from the top portion 204*a* and can serve as a connection point for the locking collar 112. One or more pins or dowels 207 can retain the locking collar 112 to the reamer attachment 204. Each pin 207 can extend from a dowel opening 2070 in the cylindrical body 204*b*. The locking collar 112 can be located on the cylindrical body 204*b* such that the dowel openings 2070 and the dowels 207 extending therefrom can each be received within one of a plurality of circumferential slot 112*s* formed in the locking collar 112. The cylindrical body 204*b* can have a plurality of through holes 208, each of which can receive a ball bearing 210 therein. The ball bearing 210 can be received within the through hole 208 such that a portion of the detent ball extends beyond an internal surface 204*i* (see FIG. 7) and an external surface

204*e* of the cylindrical body 204*b*. While three through holes 208 and detent balls 210 are shown in the illustrated embodiment, a greater or fewer number of through holes 208 and ball bearings 210 can be present in the reamer attachment 204.

The locking collar 112 can be a positive locking collar and can secure the reamer head to the housing 108 with a tight fit for stability of the reamer head 110. This secure connection can, among other things, provide for reproducible and reliable bone preparation, as well as a reduction in safety concerns while operating the reamer 100. More particularly, the locking collar 112 can be sized to fit around the external wall 204*e* of the cylindrical body 204*b* of the reamer attachment 204 and can be rotated to secure the reamer head 110 to the housing 108. The locking collar 112 can have a track 112*t* formed therein such that an internal surface 112*i* of the locking collar can have one or more ramp portions 112*r*. The ball bearings 210 of the reamer attachment 204 can align and be received within the track 112*t* of the locking collar 112. Each ball bearing 210 can slide along one of the ramp portions 112*r* of the locking collar 112 with rotation of the locking collar about the reamer attachment 204. As the locking collar 112 is rotated in a first direction, each ball bearing 210 can move along its respective ramp portion 112*r* towards a locking channel 112*c*. Each ramp portion 112*r* can extend along a portion of a circumference of the inner surface 112*i* of the locking collar 112. The locking channel 112*c* can extend distally from the ramp portion 112*r* with a rounded lip 1121 that can urge the ball bearing 210 radially inward. An external surface 112*e* of the locking collar can include grip features, such as ridges or teeth, which can assist a user in rotating the locking collar and/or can serve as a ratcheting feature with the locking lever 114.

Figure 8:
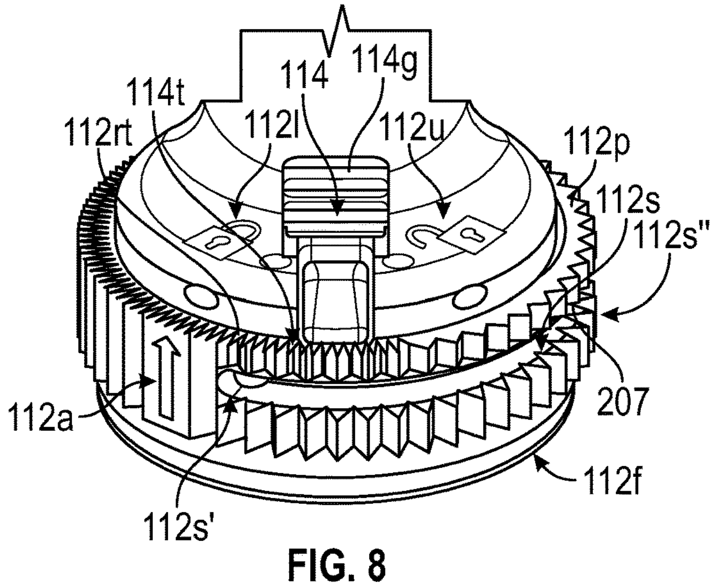
FIG. 8 is a top-down view of the distal end of the half-wedge housing and the locking collar of FIG. 3.
Figure 9:
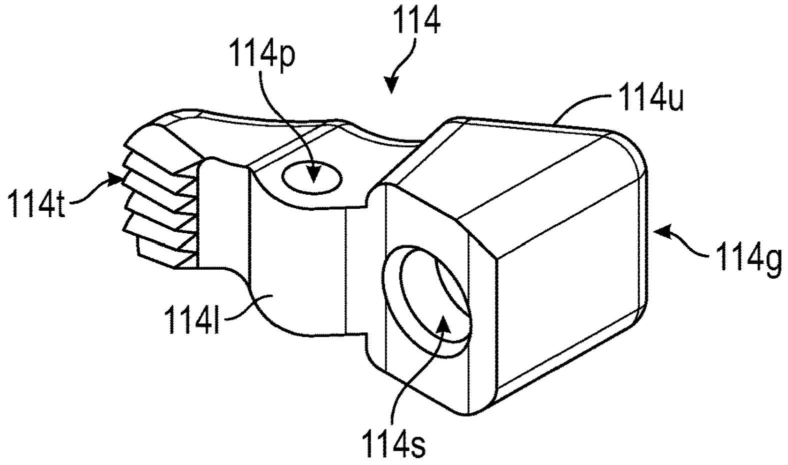
FIG. 9 is a bottom-up perspective view of a locking lever of the instrument of FIG. 1.
Figure 10:
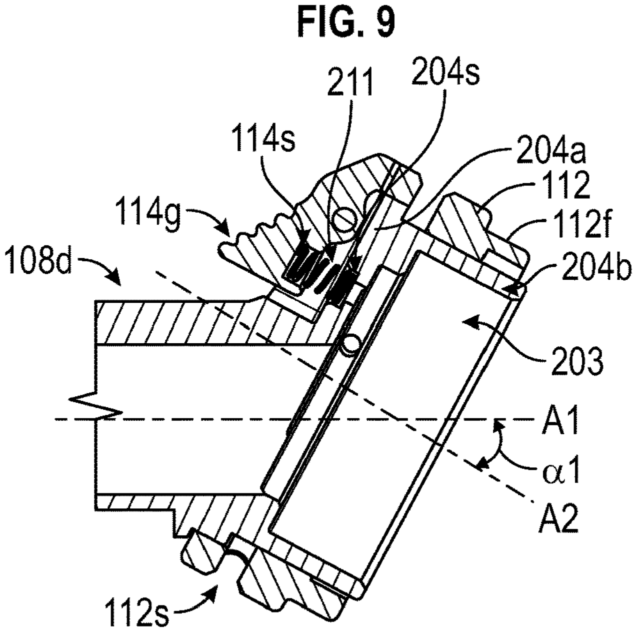
FIG. 10 is a cross-sectional view of the distal end of the half-wedge housing and the locking collar shown in FIG. 8.

FIG. 8 shows the locking collar 112 and locking lever 114 retained on the housing 108 and, more particularly, the reamer attachment 204. FIG. 9 shows the locking lever 114 in greater detail. FIG. 10 is a cross-sectional view of the distal end of the housing 108, with the locking collar 112 and the locking lever 114 secured to the reamer attachment 204. The locking lever can have an upper face 114*u*, a lower face 1141, a grip 114*g*, a pin opening 114*p*, a spring opening 114*s*, and teeth 114*t*. With additional reference to FIG. 4, the locking lever 114 can be partially seated within a recess 204*r* of the reamer attachment 204. The locking lever 114 can be pivotably coupled to the reamer attachment 204 via a pin 209 (see FIG. 4) that can extend across the recess 204*r* through the pin-receiving opening 1140 in the locking lever 114 and a spring 211. A first end of the spring 211 can be located within the spring opening 114*s* of the locking lever 114 and can cross the recess 204*r* to a second end of the spring located within a bore 204*s* of the reamer attachment 204. In a resting or non-actuated position, the lower face 1141 can contact the reamer attachment 204 and the teeth 114*t* can engage with ratcheting features 112*rt*, such as teeth or ridges, that can be formed on a proximal-facing surface 112*p* of the locking collar 112. The locking lever 114 can be pivoted away from the locking collar 112, e.g., by depressing the grip 114*g* of the locking lever towards the top 204*a* of the reamer attachment 204, such that the teeth 114*t* of the locking lever disengage from the locking collar 112. The locking lever 114 can effectively hold the locking collar 112 in place relative to the reamer attachment 204 such that rotation of the locking collar 112 relative to the reamer attachment can occur only when the teeth 114*t* of the locking lever are disengaged from the collar. The positive locking design can ensure that there is no unintended displacement of the reamer cutting head 110 relative to the housing 108, e.g., during a reaming procedure. The ratcheting teeth design of the locking collar to the locking lever can provide a user tactile and audible confirmation of securement between the two components.

Several visual indicators can be included on one or more of the reamer attachment 204 and the locking collar 112 that can assist a user in assembly of the reamer instrument 100. For example, a flange 112*f* with a reduced diameter can form a distal end of the locking collar 112. The flange 112*f* can have a smooth exterior surface and can couple with a portion of the reamer head 110. The flange 112*f* can have a laser line or other etching on at least a partial portion of a circumference of the flange. When the reamer head 110 is fully seated or inserted within the reamer attachment 204, the reamer head 110 can at least partially obstruct view of the otherwise visible laser line or etchings. The reamer head 204 can have indicators 1121, 112*u* visibly formed or marked thereon that can represent an unlocked and a locked position of the locking collar 112, respectively. The locking collar 112 can have an arrow indicator 112*a* that can be formed or marked on the external surface 112*e* of the locking collar so as to align with the locked and unlocked indicators 1121, 112*u* of the reamer head 204 when the locking collar 112 is in the corresponding position. Other visual indicators can be provided in addition to or in lieu of the indicators 112*a*, 1121, 112*u*.

Figure 11A:
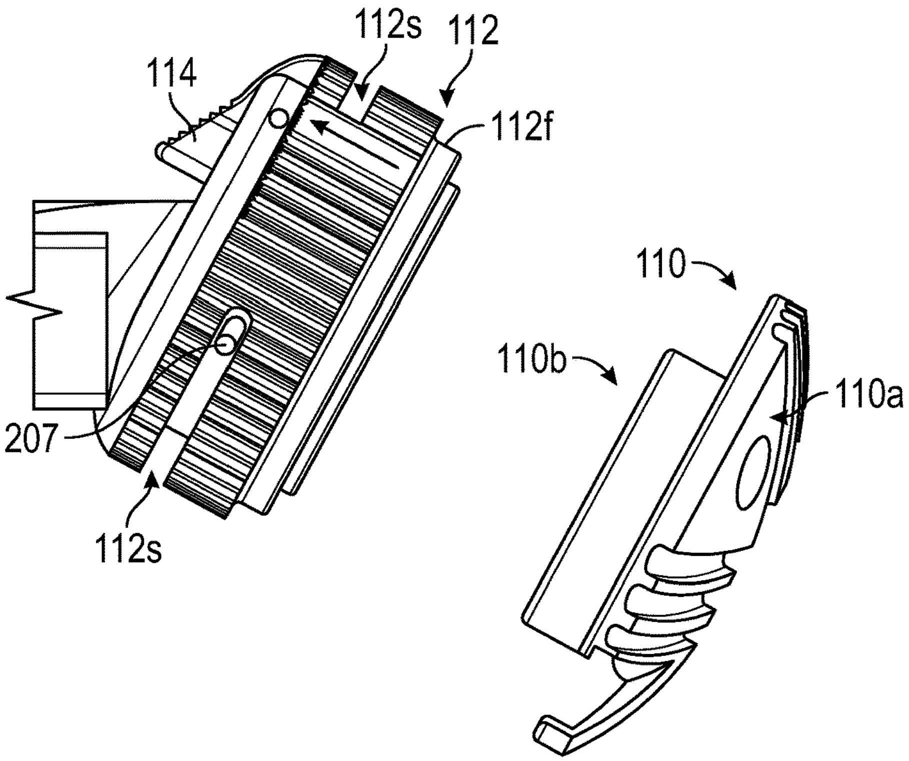
FIG. 11A is an exploded view of the distal end of the housing and a reamer head of the instrument of FIG. 1.
Figure 11B:
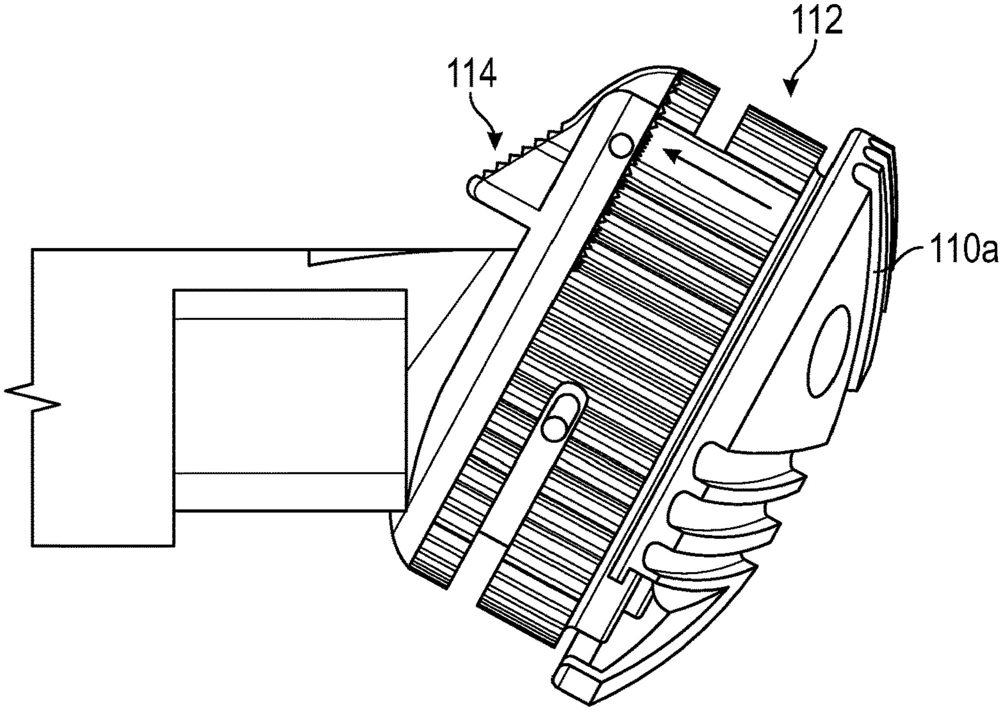
FIG. 11B is an enlarged view of the distal end of the housing assembled with the reamer head of FIG. 11A.

FIG. 11A is a side-view of the distal end of the housing 108*d* with the locking collar 112 and the locking lever 114 secured to the reamer attachment 204 and the reamer head 110 positioned for assembly onto the housing. FIG. 11B shows the assembled components of FIG. 11A. The reamer head 110 can have a cutter or blade head assembly 110*a* and an outer bearing 110*b*. The outer bearing 110*b* can be a shielded ball bearing that does not require lubrication. The reamer head 110 can be removably coupled to the distal end 108*d* of the housing 108. More particularly, the outer bearing 110*b* can be received within the opening of the hollow cylindrical body 204*b* of the reamer attachment 204. The locking collar 112 can be rotated while the locking lever 114 is depressed to secure the outer bearing 110*b*, and accordingly the reamer head 110, to the housing 108. As discussed above, rotating the locking collar 112 to the locked position can cause the bearing balls 210 to move radially inward, which can exert a radially inward force on the outer bearing 110*b* of the reamer head 110. This force can lockably secure the reamer head 110 to the housing 108 in a secured manner until the locking lever 114 is depressed and the locking collar rotated away from the locked position. With the reamer head 110 secured and locked to the housing 108, the blade head 110*a* can form a distal face of the reamer 100 and, as discussed in detail below, can be driven by the drive tip to ream or cut bonc. The reamer head 110 and blade head 110*a* can be oriented along the axis A2 of the reamer attachment 204. The blade head 110*a* can extend at the same angle α1 relative to the central longitudinal axis A1 of the housing 108 as the reamer attachment 204.

Figure 12:
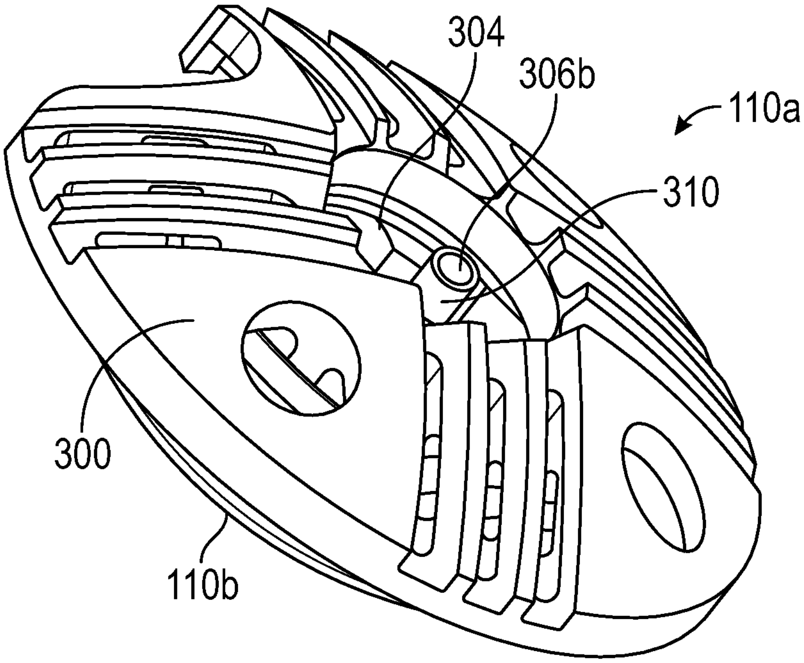
FIG. 12 is a top-down perspective view of a blade head assembly of the reamer head of FIG. 11A.
Figure 13:
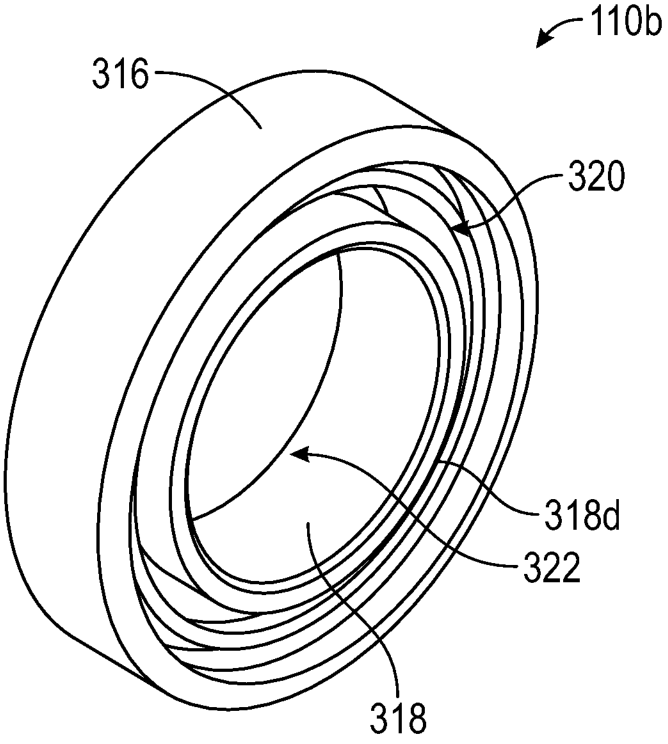
FIG. 13 is a bottom-up perspective view of an outer bearing of the reamer head of FIG. 11A.
Figure 14:
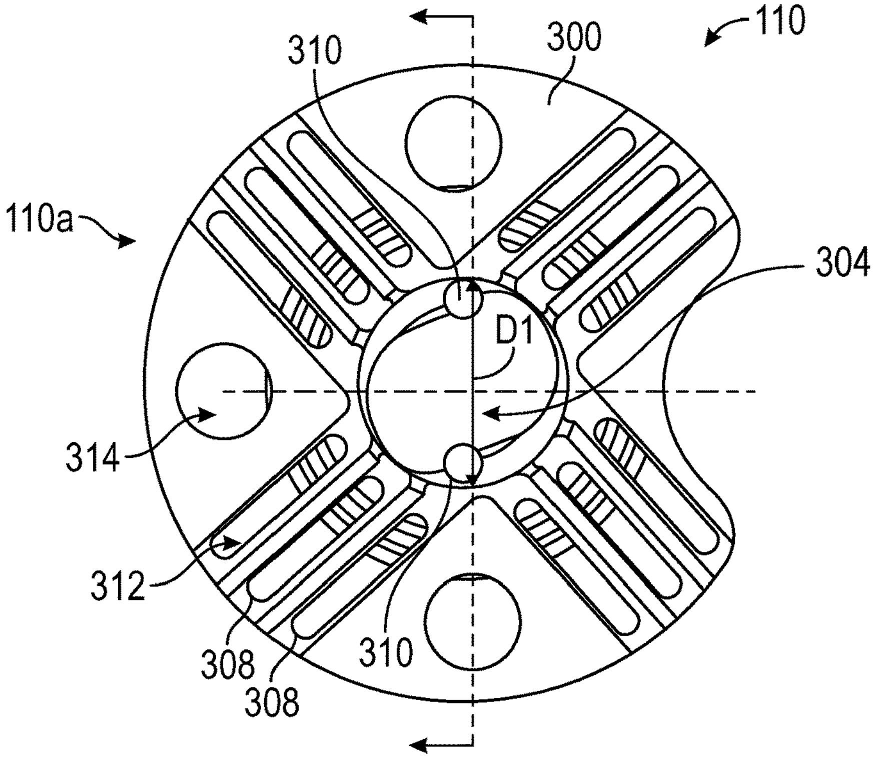
FIG. 14 is a front view of the reamer head of FIG. 11A.

One embodiment of the reamer head 110 will now be described in greater detail with reference to FIGS. 12-17. As noted above, the reamer head 110 can have a cutter or blade head assembly 110*a* and an outer bearing 110*b*. The blade head assembly can have a rounded or spherical blade top 300 and a pin housing 302 that can extend distally from an underside of the top. The pin housing 302 can have a generally cylindrical exterior with an opening, lumen, or throughbore 304 extending therethrough. The throughbore 304 (also referred to herein as an engagement aperture) can extend through the pin housing 302 and through the blade head assembly 110*a*. The throughbore 304 can have a non-cylindrical shape and/or oblong or aperture and can receive a plurality of pins 306*a*, 306*b*, which can also be referred to as engagement posts or pins 306*a*, 306*b*. As discussed in detail below, the pins 306*a*, 306*b* of the reamer head 110 can be in contact with drive pins 522*a*, 522*b* (see, e.g., FIG. 25) of the drive tip 102 such that rotation of the drive tip can cause rotation of the reamer head 110 to ream a bone surface. More particularly, the blade head assembly 110*a* can include a plurality of teeth or blades 308 that, when rotated, can ream or cut into a bone surface. The throughbore 304 can have an oblong or elongated oval shape with walls that circumferentially taper to form one or more pockets or partially cylindrical recesses 310 to receive a driven pin. For example, in one embodiment, a pocket 310 can be formed along a perimeter of the throughbore 304 at either end of a minor diameter D1 of the throughbore 304. For example, as can be seen in FIGS. 12 and 14, two pin receptacles 310 can be formed on opposite sides of the throughbore 304 at a minor diameter D1 of the throughbore. A pin 306*a*, 306*b* can be welded or otherwise secured within the pocket 310 such that the pin is fixedly received or placed within the pin housing 302. The pins 306*a*, 306*b* can extend longitudinally within the throughbore 304, i.e., in a direction substantially parallel to a longitudinal axis of the throughbore. The illustrated non-cylindrical, oblong shape of the throughbore 304 allows for the drive tip 102 (not shown in FIGS. 12-17) to freely rotate and/or translate without galling the blade head assembly 110*a*. The illustrated shape of the throughbore 304 also helps prevent jamming when the head 110*a* of the reamer 100 reverses direction.

As noted above, the blade head assembly 110*a*, sometimes referred to as a blade head or cutter head, can include a plurality of teeth or blades 308 that, when rotated, can ream or cut into a bone surface. By way of non-limiting example, the blade head 110*a* can have four sets of teeth 308 with three teeth per set. The teeth sets can be formed substantially equidistant around a circumference of the blade head 110*a*. Alternative placement and/or number of teeth 308 and/or sets of teeth fall within the scope of the present disclosure. A surface or profile of the blade head 110*a* can match a spherical radius of an implant to be implanted into the bone to be reamed. In this manner, the reamer head 110 can ream or cut a bone surface to an appropriate geometry to accept the implant. The blades 308 can be biased in a first direction such that the blade head 110*a* cuts bone only upon rotation in the first direction. This safety measure can prevent accidental reaming of the bone that may result in formation of an unintended bone surface geometry. Rotation of the cutter head 110*a* in a second direction opposite the first can result in rotation of the blades 308 over or near a bone surface without cutting or reaming into the bone. For example, rotation of the reamer head 110 in the clockwise direction from a user's perspective while looking into a joint being operated on, i.e., into a bone surface being prepared, can drive the leading edge of the blades 308 to cut into bone, while rotation in the counter-clockwise direction will not prepare or cut the bone. One or more slots 312 can extend through the blade head 110*a* between blades 308. The slots 312 can permit passage of bone or other debris through the blade head 110*a* and away from the reaming site. One or more holes 314 can extend through the cutter head 110*a* and be located remote of the blades 308. Like the slots 312, the holes 314 can minimize bone packing and facilitate removal of bone debris during a surgical procedure. The slots and holes 302, 304 can facilitate continuous reaming while minimizing stoppage time for cleaning or debris removal during a procedure. Other sizes, shapes, configurations, and locations of slots 312 and holes 314, sometimes more generally referred to as debris-relief openings, are possible without departing from the spirit of the present disclosure.

The pin housing 302 can fit securely within the outer bearing 110*b* such that the blade head 110*a* can rotate relative to and within the outer bearing 110*b*. More particularly, the outer bearing 110*b* can have an outer housing 316, an inner housing 318, a roller bearing 320 placed between the outer housing and the inner housing, and a lumen or throughbore 322 extending through the inner housing. Each of the outer housing 316, the inner housing 318, and the roller bearing 320 can be cylindrical with an outer diameter D2 of the inner housing being less than an inner diameter D3 of the roller bearing 320, which can be less than an inner diameter D4 of the outer housing 316. The inner diameter D1 of the inner housing 318 can be slightly larger than an outer diameter D5 of the pin housing 302 of the blade assembly 110*a*. The outer bearing 110*b* can then be pressed or otherwise placed around the pin housing 302 (also referred to as a bearing journal of the blade assembly 110*a*) such that a distal end 318*d* of the inner housing 318 can be flush with a shoulder 320 of the blade assembly 110*a*. The shoulder 320 can be formed at a transition between the larger-diameter top 300 and the smaller-diameter pin housing 302. Returning to FIGS. 11A and 11B, the outer housing 316 of the outer bearing 110*b* can be sized to securely fit within the cylindrical opening of the reamer attachment 204. For example, an outer diameter of the outer housing 316 can be equal to or slightly smaller than an inner diameter of the cylindrical opening of the reamer attachment 204. In this manner, the outer bearing 110*b* with the blade assembly 110*a* secured thereto can be inserted into the reamer attachment 204 such that the reamer head 110 can be rotatably and securely received therein. The outer housing 316 can remain stationary within the reamer attachment 204 while the blade assembly 110*a* and the inner housing 318 of the outer bearing 110*b* can rotate when driven by the drive shaft 104 and drive tip 102.

FIGS. 18-21 illustrate the depth stop 116 of the half-wedge reamer instrument 100 in greater detail. As noted above, the depth stop 116 or stop foot can be attached to the half-wedge housing 108 to achieve an intended geometry of a bone surface. The depth stop 116 can have a body 400 with an engagement end 400*a*, a stop guard end 400*b*, an inner surface 400*i*, an outer surface 4000. A curved arm 400*c* can extend between the engagement end 400*a* and the stop guard end 400*b* of the depth stop 116. The engagement end 400*a* can securely couple the depth stop 116 to the half-wedge housing 108 at the recessed portion or attachment location 115 of the housing. In some embodiments, the engagement end 400*a* can have a pair of spaced apart arms 402*a*, 402*b* that can mate with the recessed portion 115 of the housing 108, e.g., with a snap-fit connection. It will be appreciated that alternative mechanism and/or methods of coupling the depth stop 116 to the housing 108 are possible and fall within the scope of the present disclosure. The inner surface 400*i* of the depth stop 116 can be described as the surface of the depth-stop that faces towards the housing 108 when the depth stop 116 is coupled to the housing. The outer surface 4000 can be described as the surface of the depth-stop that faces away from the housing 108 when the depth stop 116 is coupled to the housing.

With the depth stop 116 coupled to the housing 108, at least a portion of the stop guard end 400*b* can be axially-aligned with a portion of the reamer head 110. More particularly, at least a portion of the inner surface 400*i* of the depth stop 116 at the stop guard end 400*b* can oppose or face the blade top 300 of the reamer head 110. A portion of the reamer attachment 204 and reamer head 110 can be placed between the engagement end 400*a* and the stop guard end 400*b* of the depth stop in a way that permits free rotation of the reamer head 110 without contacting the depth stop 116. In this manner, at least a portion of the depth stop 116 can extend between the reamer head 110 and a bone surface to prevent blades 308 of the reamer head 110 from reaming or cutting bone. Rather, the outer surface 4000 of the depth stop 116 at the stop guard end 400*b* can contact the bone surface. To this end, the stop guard end 400*b* of the depth stop 116 can have a curved or spherical shape, sometimes referred to as arcuate, that can match the shape of an implant to be received by the bone surface. Accordingly, reaming the bone with the half-wedge housing 108 and depth stop 116 can reliably prepare the bone surface to a known geometry for receiving the implant. A guide pin 404 can extend distally from the outer surface 4000 of the stop guard end 400*b*. In use, the guide pin 404 can be inserted into or mate with a hole formed in the bone surface to hold the depth stop 116 secure and steady relative to the bone surface. For example, in some embodiments the guide pin 404 can have a diameter of about 2.4 mm and can be inserted into a similarly sized pre-drilled hole in the bone surface. A longitudinal axis A3 of the guide pin 404 can extend substantially parallel to the longitudinal axis A1 of the housing 108 when the depth stop 116 is coupled to the housing. The longitudinal axis A3 of the guide pin 404 can extend substantially perpendicular to a longitudinal axis A4 of the arms 402*a*, 402*b* of the depth stop engagement end 400*a*. A person skilled in the art will appreciate other sizes, shapes, and configurations of a depth stop that can be used in conjunction with the reamer instrument 100, or other reamer instruments disclosed herein or otherwise derivable from the present disclosures, without departing from the spirit of the present disclosure. Such sizes, shapes, and configurations can depend, at least in part, on configurations and designs of other components of the reamer instrument (e.g., the half-wedge or other shaped housing, the reamer head, etc.), anatomies of the patient, and preferences of the surgeon, among other factors.

Figure 22:
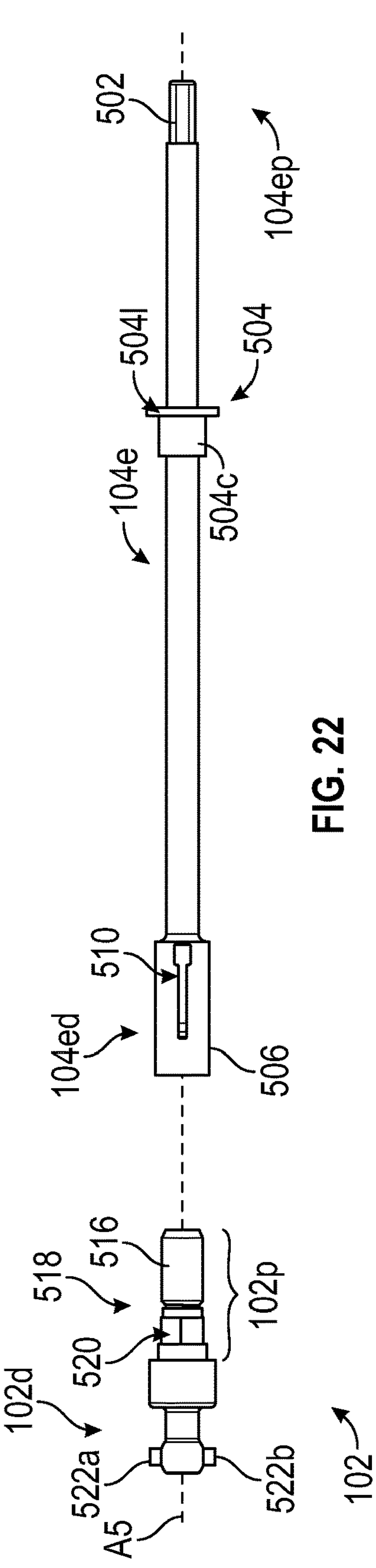
FIG. 22 is an exploded view of a drive shaft of the instrument of FIG. 1, the drive shaft having a drive tip and an elongate shaft.
Figure 23B:
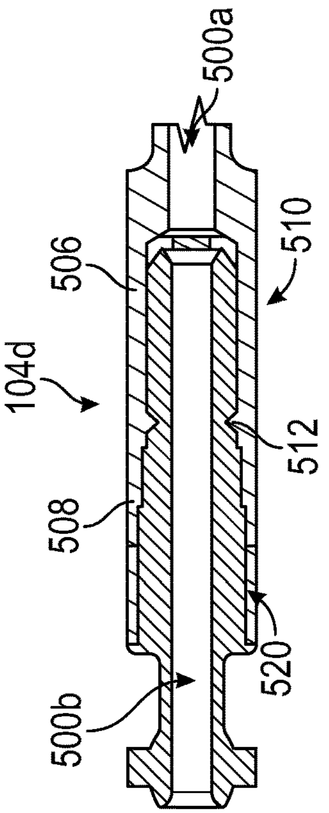
FIG. 23B is a cross-sectional view of the enlarged view of the distal end of the drive shaft shown in FIG. 23A.
Figure 23A:
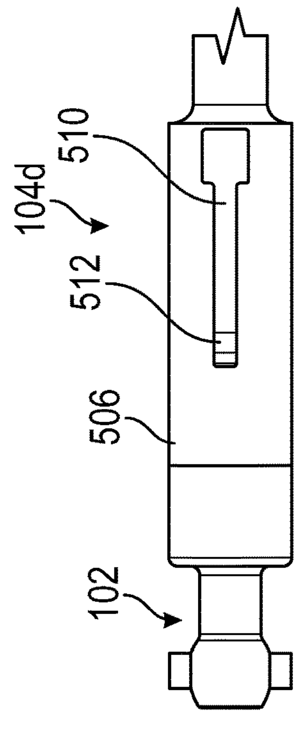
FIG. 23A is an enlarged view of a distal end of the drive shaft of FIG. 22.
Figure 24:
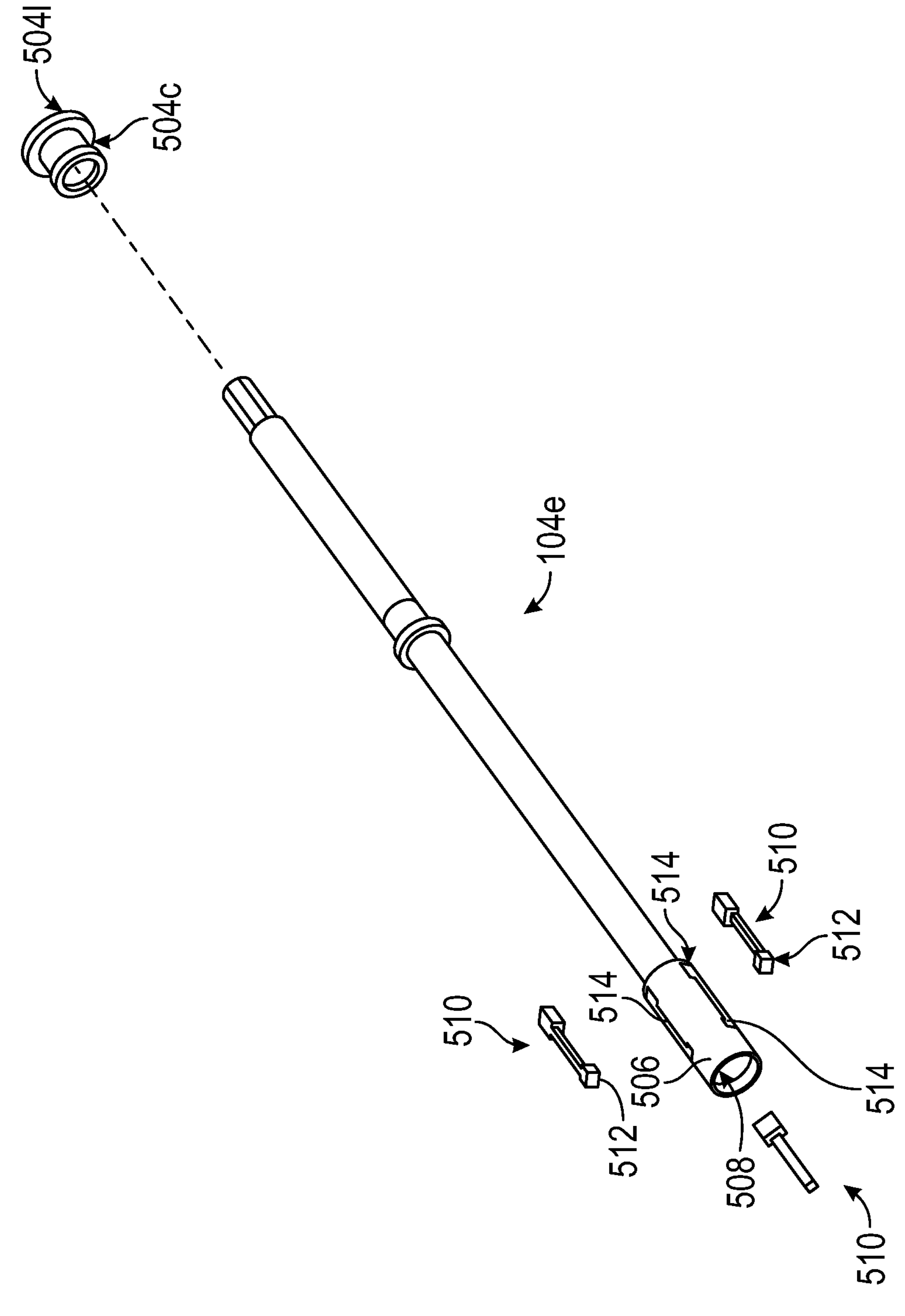
FIG. 24 is an exploded view of the elongate shaft of the drive shaft of FIG. 22.

One embodiment of the drive shaft 104 is illustrated in greater detail in FIGS. 22-24. As noted above, the drive tip 102 can be coupled to the distal end 102*ed* of the elongate shaft 104*c* to form the drive shaft 104. The drive shaft 104 can extend through the throughbore 201 of the housing 108, with at least a portion of the drive tip 102 extending into the reamer attachment 204 and contacting a portion of the reamer head 110 such that rotation of the drive tip 102 can cause rotation of the reamer head 110 to cut into bone. The drive shaft 104 can have a generally elongate body having a proximal end 104*p* and a distal end 104*d* with a lumen or throughbore 500*a* extending therethrough. The proximal end 104*p* of the drive shaft 104 can have a power connector 502 that can couple to a power source (not shown), such as a motor, a drill more generally, or other power source(s) known to those skilled in the art. For example, the power connector 502 can be formed at the proximal-most end of the drive shaft 104 as a hex-feature or other male connector feature that can be received within a complementary connection of the power source such that operation of the power source can cause the drive shaft 104 to rotate. In the assembled instrument 100, the power connector 502 can be inserted into a distal end of the drill connection 120 within the handle 106. In this manner, the drive shaft 104 can be coupled to the drill connection 120 and can be driven to rotate by a power source, e.g., a drill, coupled to the drill connection 120.

A collar 504 can be formed or otherwise disposed on the drive shaft 104 distal to the power connector 502. The collar 504 can be sized to be received within a proximal portion of the housing throughbore 201. For example, the collar 504 can include a lip 5041 and a body 504*c*. A diameter of the body 504*c* can be equal to or smaller than a diameter of a proximal portion of the housing throughbore 201 such that the body can be received within the throughbore 201. The lip 5041, on the other hand, can have a diameter greater than the diameter of the proximal portion of the housing throughbore 201. Accordingly, the lip 5041 can abut the proximal portion of the housing 108 without extending or fully extending into the housing throughbore 201.

The distal end 104*ed* of the elongate shaft 104 can have a cylindrical barrel 506 that can securely receive a proximal end 102*p* of the drive tip 102 such that the drive tip can be driven, i.e., rotate, with the elongate shaft. The cylindrical barrel 506 can have an internal hex feature 508 at a distal end thereof that can couple with an external hex feature 520 of the drive tip 102. One or more spring fingers 510 can be coupled to the cylindrical barrel 506. A lever catch 512 of the spring finger 510 can extend through an opening 514 of the cylindrical barrel 506 and into the inner throughbore 500*a* of the drive shaft 104.

The drive tip 102 can have a proximal end 102*p*, a distal end 102*d*, and an inner lumen or throughbore 500*b* extending therethrough. The proximal end 102*p* can be inserted into and received within the cylindrical barrel 506 of the drive shaft 104. The proximal end 102*p* of the drive tip 102 can include a cylindrical portion 516, a notch or groove 518, and a hex connection feature 520. The notch 518 of the drive tip 102 can be formed between the cylindrical portion 516 and the hex connection feature 520 and can have a reduced diameter relative to adjacent portions of the drive tip. The distal end 102*d* of the drive tip can have first and second drive pins 522*a*, 522*b* that can contact posts 306*a*, 306*b*, respectively, of the reamer head 110 when the reamer instrument 100 is fully assembled. Just as the posts 306*a*, 306*b* can be described as engagement pins or posts, so too can the first and second drive pins 522*a*, 522*b*. The drive pins 522*a*, 522*b* can extend substantially perpendicular to a longitudinal axis A5 of the drive tip 102. Variations on the illustrated embodiment of drive pins 522*a*, 522*b* fall within the scope of the present disclosure. For example a greater or fewer number of drive pins 522 can extend from the drive tip 102, and/or from different locations. By way of further non-limiting example, additionally, or alternatively, the drive pins 522 can extend at an oblique angle relative to the longitudinal axis A5 of the drive tip 102.

Figure 25:
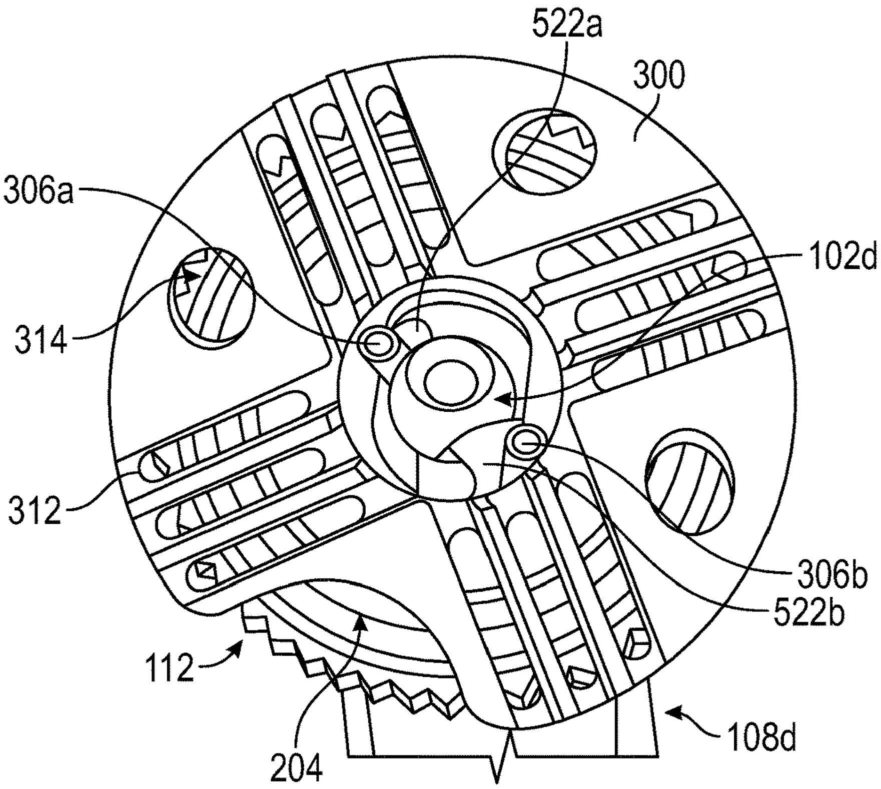
FIG. 25 is an enlarged bottom-up view of the distal end of the instrument of FIG. 1 with a coupling between the drive tip of FIG. 22 and the reamer head of FIG. 11A visible.
Figure 26:
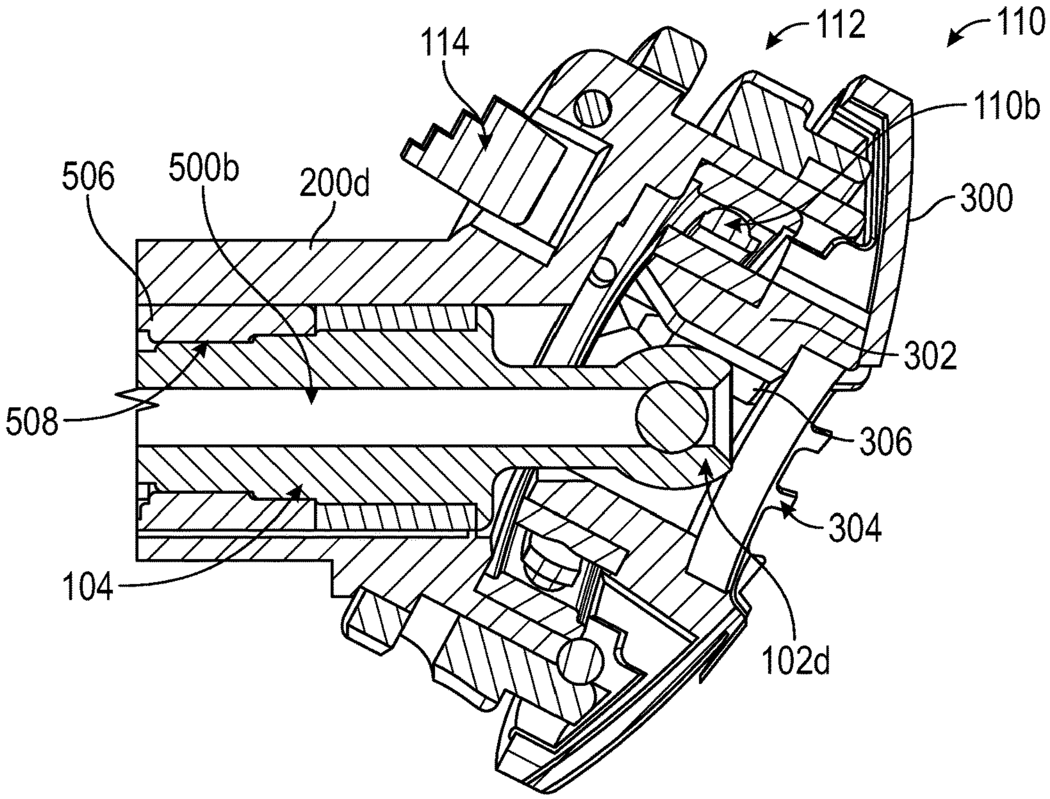
FIG. 26 is a cross-section view showing in cross-section the reamer head of FIG. 25, the locking collar of FIG. 3, the drive tip of FIG. 22, and a housing reamer attachment of the instrument of FIG. 1.

As can be seen in FIG. 23B, which provides for a cross-sectional view of the distal end of the drive shaft 104*d* with the drive tip 102 coupled thereto, the notch 518 can align with the lever catch 512 of the one or more spring fingers 510 such that the lever catch 512 can extend through the window 514 of the cylindrical barrel 506 and into the notch 518 of the drive tip 102. The spring fingers 510 can axially retain the drive tip 102 within the drive shaft 104 and can assist in transferring driving torque from the drive shaft 104 to the drive tip 102. The inner throughbore 500*b* of the drive tip 102 can be co-axial with the inner throughbore 500*a* of the drive shaft 104. In this manner, the assembled drive tip 102 and drive shaft 104 can be inserted over a guide wire (not shown). The drive tip 102 can extend distally from the distal end 104*d* of the drive shaft 104 such that drive pins 522*a*, 522*b* are located distal to the distal end 200*d* of the elongate body 200 of the housing 108 (see FIG. 26) in the assembled reamer instrument 100. FIGS. 25 and 26 show the distal end 108*d* of the housing 108 with the locking collar 112 and reamer head 110 coupled to the reamer attachment 204 and the drive shaft 104 and drive tip 102 inserted through the housing 108. The first drive pin 522*a* of the drive tip 102 can abut the first engagement post 306*a* of the blade head 110 and the second drive pin 522*b* of the drive tip 102 can abut the second engagement post 306*b* of the blade head 110*a*. Rotation of the drive tip 102, and thus drive pins 522*a*, 522*b*, in a first direction can cause rotation of the blade head 110*a* in the first direction as a result of contact between the drive pins 522*a*, 522*b* and their respective engagement posts 306*a*, 306*b*. Rotation in a second direction, opposite the first direction, however, can cause the drive pins 522*a*, 522*b* to rotate or move away from their respective engagement posts 306*a*, 306*b* such that the blade head 110*a* does not rotate.

Figure 27:
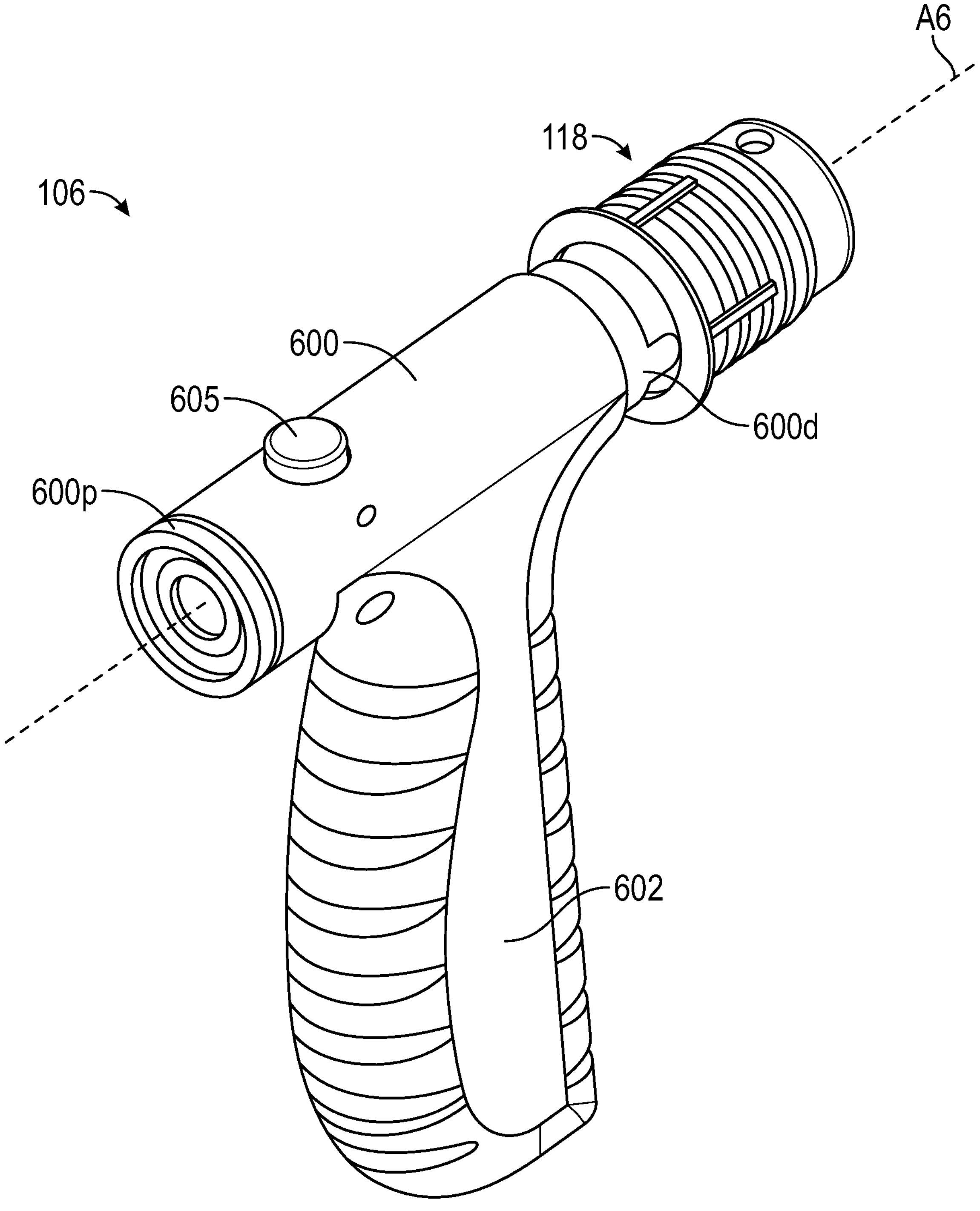
FIG. 27 is a perspective view of a handle, including a release collar, of the instrument of FIG. 1.
Figure 28:
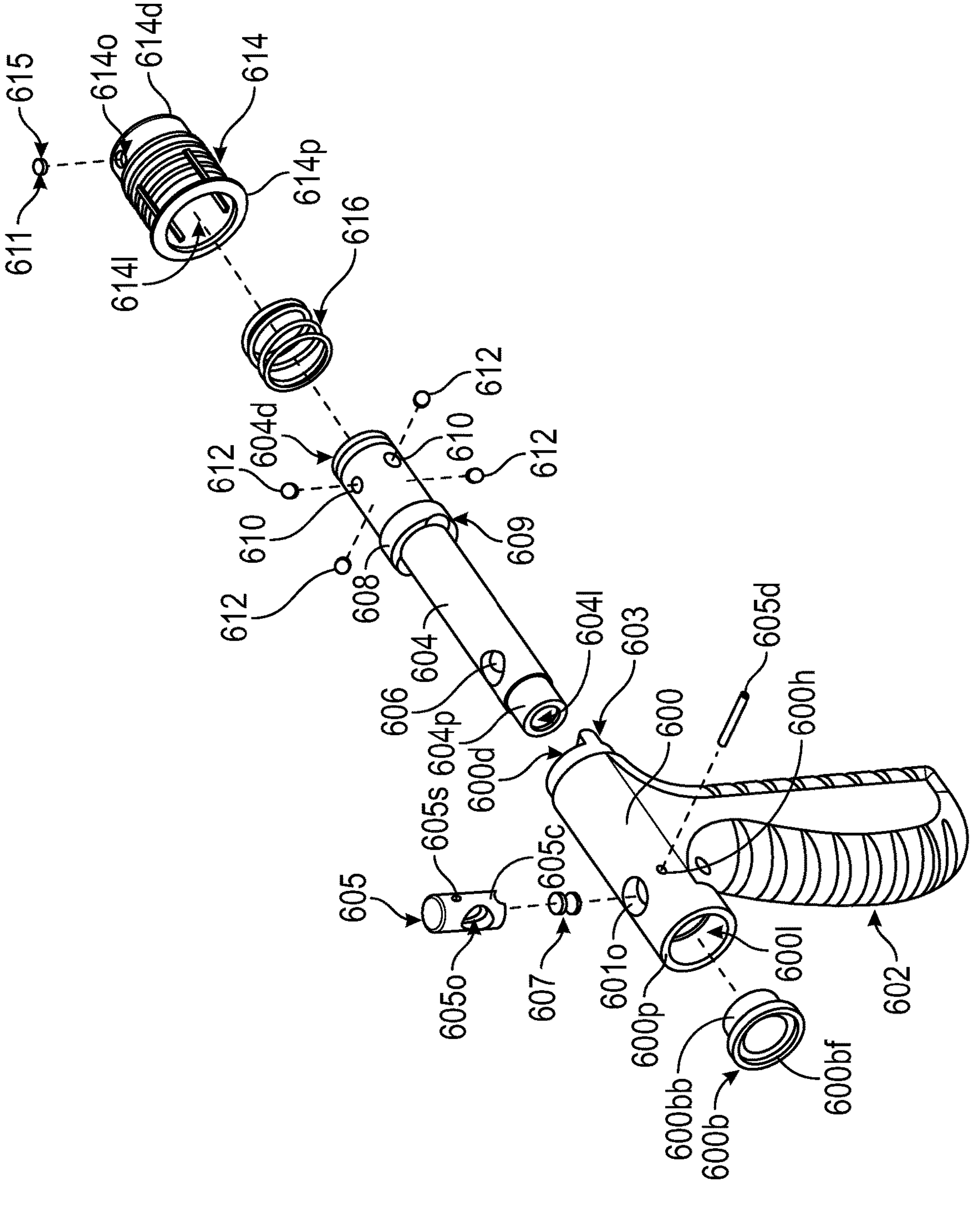
FIG. 28 is an exploded view of the handle, including the release collar, of FIG. 27.

One embodiment of the handle 106 and quick release collar 118 of the reamer instrument 100 is illustrated in FIGS. 27-30. FIGS. 27 and 28 illustrate one embodiment of the handle 106 and quick release collar 118 in an assembled view and an exploded view, respectively. The handle 106 can have a modular design and can include a tubular body portion 600 and an intermediate handle portion 604, as well as the release collar 118. Each of these components can have a lumen or throughbore extending therethrough such that, when assembled, each of the lumens or throughbores is co-axial along a central longitudinal axis A6 of the handle. The quick release collar 118 can facilitate releasable coupling and selective rotational positioning of the housing 108*p* to the handle 106. The drive shaft 104 of the reamer instrument 100 can extend through the handle 106 and through the housing 108 coupled to the handle.

The tubular body portion 600 that can extend from a proximal end 600*p* to a distal end 600*d* with a lumen or throughbore 6001 extending therethrough. A bushing 600*b* can be inserted into the throughbore 6001 and can extend proximally from the tubular body portion 600. The bushing 600*b* can receive a proximal end 604*p* of the intermediate handle portion 604 within a bore formed in a body 600*bb* of the bushing 600*b*. The bushing 600*b* can also receive a portion of the drill connection 120. More particularly, the first end 120*a* of the drill connection 120 can be inserted through the bushing 600 and into the throughbore of the handle 106. A flange 600*bf* can be formed at a proximal end of the bushing body 600*bb* and can be sized to securely receive the washer 122 of the drill connection 120 (see FIG. 29). An opening 601 can extend through at least one wall of the tubular body portion 600 to intersect with the throughbore 6001. As discussed in detail below, the opening 601 can be part of a release mechanism to assist in disassembly of the instrument 100. A protrusion or lug 603 can extend distally from the distal end 600*d* of the tubular body portion 600. A grip 602 can extend laterally from the tubular portion 600. The grip 602 can be held by a user during operation of the reamer instrument 100 and can include one or more ergonomic features, such as ridges or a rounded shape.

The intermediate handle portion 604 of the handle 106 can be a generally tubular or elongate body with a proximal end 604*p*, a distal end 604*d*, and a lumen or throughbore 604*l* extending therebetween. The proximal end 604*p* of the intermediate portion 604 can be inserted into the throughbore 6001 of the tubular body 600 such that the intermediate handle 604 can extend through, and distally from, the tubular body 600. An open bore 606 can extend radially through the intermediate portion 604 and across the throughbore 604*l*. More particularly, a first opening 606*a* and a second opening 606*b* can extend through the wall of the intermediate portion 604 at locations opposite one another across a diameter of the throughbore 604*l* (see FIG. 29). The bore 606 can be placed such that the bore 606 can align with the opening 601*o* of the tubular body 600 when the intermediate portion 604 is received within the tubular body.

A release button 605 can be received within and extend through the opening 601 of the tubular body 600 and the bore 606 of the intermediate portion 604. With additional reference to FIG. 29, the release button 605 can have a substantially cylindrical body 605*b* with a proximal end 605*bp* that can extend proximally out of the opening 601*o* of the tubular body 600 and a distal end 605*bd* that can be at least partially received within a bore 601*b* formed in the tubular body 600 opposite the opening 6010. An opening 6050 can extend through the release button body 605*b*. A protrusion or notch 605*n* can extend proximally into the opening 6050. The notch 605*n* can have a width equal to or substantially equal to a width of a groove 120*g* in the drill connection 120. A longitudinal axis of the opening 6050 can extend perpendicular to an axis extending from the proximal end 605*bp* to the distal end 605*bd* of the release button body 605*b*. A counterbore 605*c* can be formed in the distal end 605*bd* of the release button body 605*b*. A spring 607 can be placed within the counterbore 605*c* such that the spring can extend distally from the distal end 605*bd* of the body.

Figure 29:
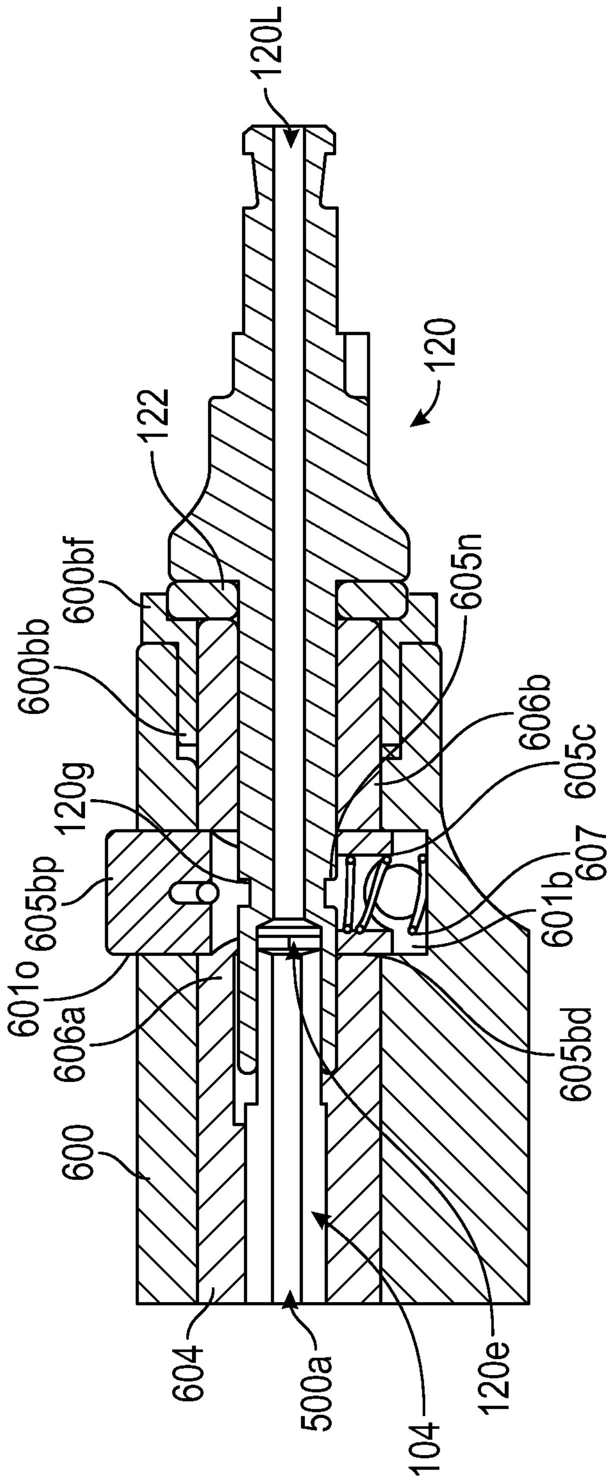
FIG. 29 is a cross-sectional view of a drill connection coupled to a proximal end of the handle of FIG. 27.

The release button 605 and spring 607 can be assembled with the handle 106, e.g., as shown in FIG. 29, such that the proximal end 605*bp* of the button body 605*b* can extend proximally out of the opening 601*o* of the tubular body 600, the button body 605 can intersect and extend across the throughbore 604*l* of the intermediate portion 604, and the distal end of the button body 605*bd* and the spring 607 can be received within the bore 601*b* of the tubular body 600. The spring 607 can bias the button body 605*b* proximally such that the notch 605*n* can extend into the throughbore 604*l* of the intermediate portion 604. The notch 605*n* can engage with the groove 120*g* of the drill connection 120 which can restrict relative movement between the drill connection 120 and the handle 106. The release button 605 can be depressed which can overcome the bias of the spring 607 and compress the spring 607 within the bore 601*b* of the tubular body. The body 605*b* can move distally such that the opening 6050 can align with the inner throughbore 604*l* of the intermediate portion 604. With the button 605 depressed, the notch 605*n* can be placed distally out of the inner throughbore 604*l* which can permit relative axial movement between the drill connection 120 and the handle 106, e.g. for assembly or disassembly of the reamer 100. Axial movement of the release button 605 can be restricted by a dowel 605*d* that can extend through a dowel-hole 605*h* in the tubular body 600 into a slot 605*s* formed in the proximal end 605*p* of the release button body 605*b*. The slot 605*s* can be formed proximally of the opening 6050.

The distal end 604*d* of the intermediate portion 604 can receive the release collar 118. To this end, a flange 608 can be formed on or otherwise secured to the intermediate portion 604 with a distal-facing surface of the flange 608 creating a shoulder to the distal end 604*d* of the intermediate portion. A portion of the throughbore 604*l* extending proximally of the flange 608 can have a diameter equal to or slightly greater than an outer diameter of a proximal portion of the drive shaft 104, i.e., a portion of the drive shaft 104 that extends proximally of the drive shaft collar 404. A portion of the throughbore 604*l* extending distally of the flange 608 can have an enlarged diameter that can be equal to or slightly greater than an outer diameter of the proximal portion of the housing 108. In this manner, the drive shaft 104 and the housing 108 can be at least partially received within the throughbore 604*l* of the handle 106. The flange 608 can include a recess or a notch 609 extending from a proximal surface of the flange towards the distal surface, without extending through the distal surface. The notch 609 can receive the extension 603 of the tubular body 600 when the intermediate portion 604 is assembled with the tubular body. It will be appreciated that the extension 603 on the tubular body 600 can be any first mating or coupling feature and the notch 609 on the flange 608 can be any second mating or coupling feature complementary to the first mating or coupling feature. One or more openings 610 located distally of the flange 608 can extend radially through the intermediate portion 604 to the throughbore 604*l*. A ball bearing 612 can be placed at least partially into each opening 610. As discussed in detail below, the ball bearing(s) 612 can facilitate selective locking of the housing 108 to the handle 106 by way of the release collar 118. More particularly, in a locked position the ball bearings 612 can be urged by the locking collar 118 through the respective opening 610 in the intermediate handle portion 604 and into the detent 202 of the housing 108.

Figure 30B:
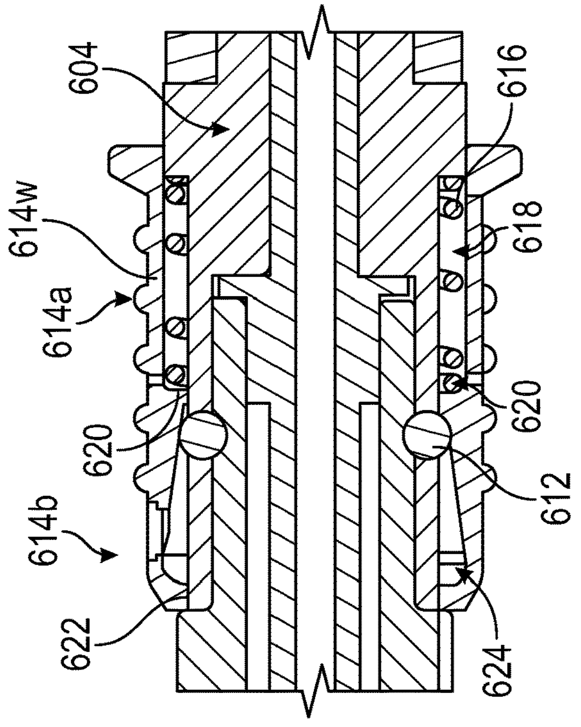
FIG. 30B is a cross-sectional view of the distal end of the handle with the quick release collar of FIG. 30A in cross-section in a retracted or unlocked position.
Figure 30A:
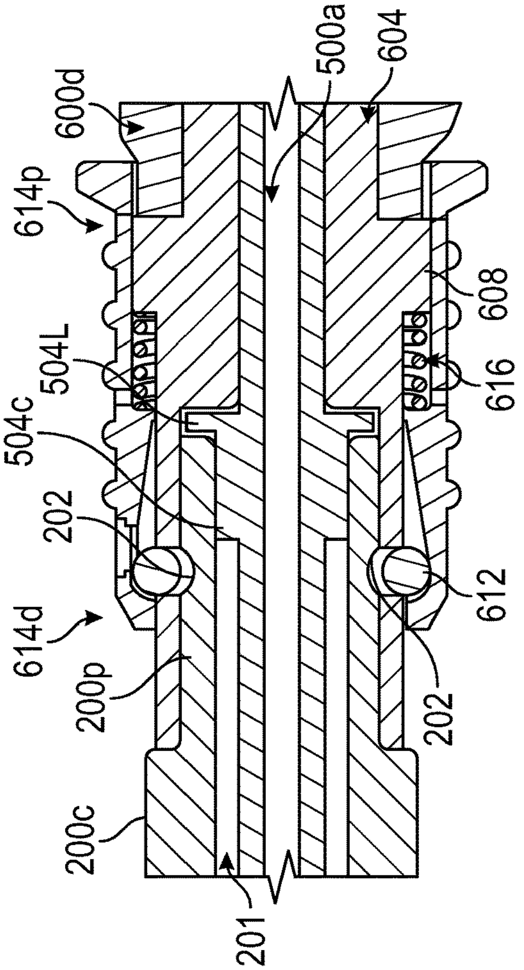
FIG. 30A is a cross-sectional view of the distal end of the handle of FIG. 27 with a quick release in a resting or locked position.

Construction of the release collar 118 is more fully understood with further reference to FIGS. 30A and 30B. FIGS. 30A and 30B are cross-sectional views of the assembled reamer instrument 100 of FIG. 1 with the release collar 118 in a retracted or unlocked position and a resting or locked position, respectively. The release collar 118 can have a body 614 with a lumen or throughbore 6141 extending therethrough and a spring 616. The throughbore 6141 can be sized to receive the distal portion 604*d* of the intermediate handle 604 and the spring 616. The body 614 can be generally U-shaped with a curved or rounded distal end 614*d*. An opening 6140 can be formed in the distal end 614*d* of the body 614. The opening 6140 can be sized to allow insertion of a ball bearing 612 therethrough. During assembly of the handle 106, the ball bearings 612 can be passed through the opening 6140 of the locking collar 118 and into the openings 610 of the intermediate handle 604. Once the ball bearings 612 have all been placed within their respective openings 610 in the intermediate handle 604, a plug 611 (see FIG. 28) can be used to seal or close the opening 6140 in the release collar body 615.

A first portion 614*a* of the body 614 can have a first bore 618. An internal lip 620 of the body 614 can define a distal end of the first portion 614*a*. The spring 616 can be seated in the first bore 618 of the first portion 614*a*. A wall 614*w* of the body 614 can have a constant thickness along an axial length over the proximal portion 614*a* of the body. In other words, the first bore 618 can have a substantially constant diameter that can be sized to receive the spring 616 and the distal portion 604*d* of the intermediate handle 604. The distal portion 604*d* of the intermediate handle portion 604 can extend through the first bore 618 and the spring 616. A proximal end 614*p* of the body 614 can have a flange or lip 622 that can assist a user in handling the body 614.

A second portion 614*b* of the body 614 can be formed distal to the first portion 614*a*. The throughbore 6141 can extend continuously through the first and second portions 614*a*, 614*b* of the body such that the intermediate handle 604 can extend axially through the release collar 118. In some embodiments, the distal end 604*d* of the intermediate handle 604 can be substantially flush with the distal end 614*d* of the release collar body 614. In the second portion 614*b* of the release collar body 614, an inner surface of the wall 614*w* can taper outwards from the inner lip 620 towards the distal end 614*d* of the body 614 to a distal end of the second bore 614*b*. Accordingly, a diameter of the inner throughbore 6141 can increase from a minimum diameter at the inner lip 620 to a maximum diameter at the distal end of the second portion 614*b*. A distal inner lip 622 can form the distal end of the second portion 614*b*. A groove 624 at the maximum diameter at the distal end of the second portion 614*b* can retain the one or more ball bearings 612 within the handle 106 when the release collar 118 is in the unlocked position (see FIG. 30A). The minimum diameter of the release collar inner throughbore 6141 can be equal to or slightly greater than an outer diameter of the distal end 604*d* of the intermediate housing portion 604.

Operation of the release collar 118 is made clearer by FIGS. 30A and 30B, and is also described in further detail below. FIGS. 30A and 30B are cross-sectional views of the assembled reamer instrument 100 taken in the vicinity of the release collar 118. As shown, the proximal portion of the elongate body 200 of the housing can be received within the throughbore 604*l* of the distal portion 604*d* of the intermediate handle 604. The detents 202 of the housing 200 can be aligned with the openings 610 of the intermediate handle 604. The drive shaft 104 can extend through the throughbores 6001, 604*l*, 201 of the handle 106 (the tubular body portion 600 and the intermediate portion 604) and the elongate body 200 of the housing 108. FIG. 30A shows the release collar 118 in an unlocked position with the spring 616 compressed within the first portion 614*a* between the flange 608 of the intermediate handle portion 604 and the inner lip 620 of the release collar body 614, i.e., the distal end of the first portion 614*a*. In the unlocked or retracted position of the release collar 118, the ball bearings 612 within the openings 610 of the intermediate handle 604 can be seated in the groove 624 at the distal end of the second portion 614*b* of the release collar body. The ball bearings 612 can thus extend only partially through the intermediate handle 604 and without entering into the intermediate handle throughbore 604*l*. Accordingly, the ball bearings 612 can remain external to the detents 202 of the housing 108. As such, the housing 108 can move relative to the handle in an axial and/or rotational manner. In other words, with the release collar 118 in the retracted position, the housing 108 can be inserted proximally into or distally removed from the throughbore 604*l* of the intermediate handle portion 604 and/or can be rotated within the throughbore 604*l* to rotate the housing 108 relative to the handle 106 about the longitudinal axis A6 of the handle 106.

FIG. 30B shows the release collar 118 in the locked position. The spring 616, in its resting position, can bias the release collar body 614 to a position in which the inner wall of the second portion 614*b* can force and hold the ball bearings 612 into the openings 610 of the intermediate handle 604 such that the ball bearings 612 are located within the detents 202 of the housing 108. In this manner, the ball bearings 612 can prevent relative movement between the housing 108 and the handle 106 in both the axial and rotational directions. The inner lip 620 of the release collar can be located proximally of the ball bearings 612. The tapered inner wall 614*w* of the release collar body 614 can urge the ball bearings 612 radially inward, towards the central longitudinal axis A6 of the handle 106, and thus towards and into the detents 202 of the housing 108.

The reamer instrument illustrated in FIG. 1 can be used to prepare a bone surface to receive an implant with a first geometry, e.g., a half-wedge implant. In such an embodiment the reamer 100 can include the half-wedge housing 108 and the depth-stop 116. Reamer instruments in accordance with the present disclosure, however, can also be used to prepare a bone surface to receive an implant with a second geometry, e.g., a full-wedge implant. In such instances, the half-wedge housing 108 can be replaced with a full-wedge housing 108' and can be used without the depth stop 116. One embodiment of the full-wedge housing 108' is illustrated and described with respect to FIGS. 31-33A. Except as indicated below, or otherwise understood by a person skilled in the art in view of the present disclosures, the structure, operation, and use of the full-wedge housing 108' is similar or identical to that of the half-wedge housing 108. Moreover, a locking collar 112' and locking lever 114' used in connection with the full-wedge housing 108' can be similar or identical to the locking collar 112 and locking lever 114 described herein in connection with the half-wedge housing 108'. Accordingly, description of the structure, operation, and use of such features, and other features, may be omitted herein for the sake of brevity.

Figure 31:
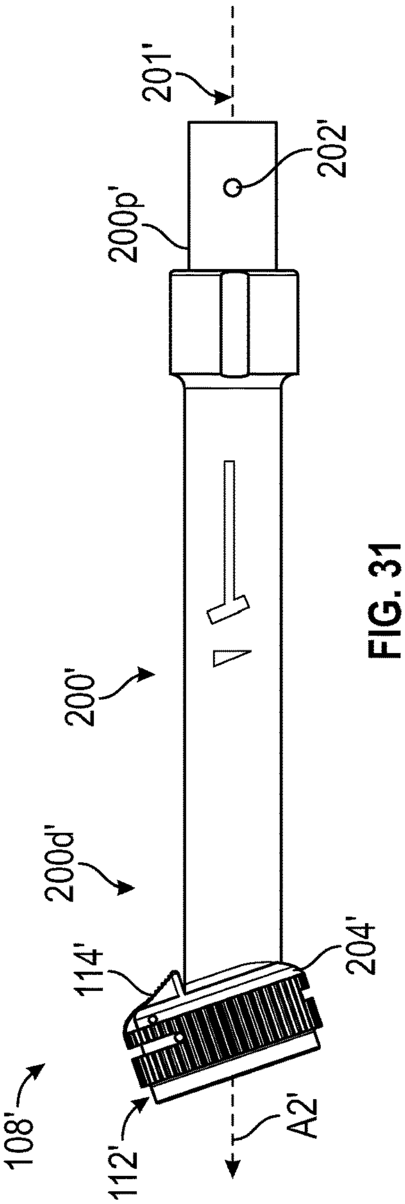
FIG. 31 is a side view of one embodiment of a full-wedge housing and locking collar that can be assembled as part of reamer instruments of the present disclosure.
Figure 32:
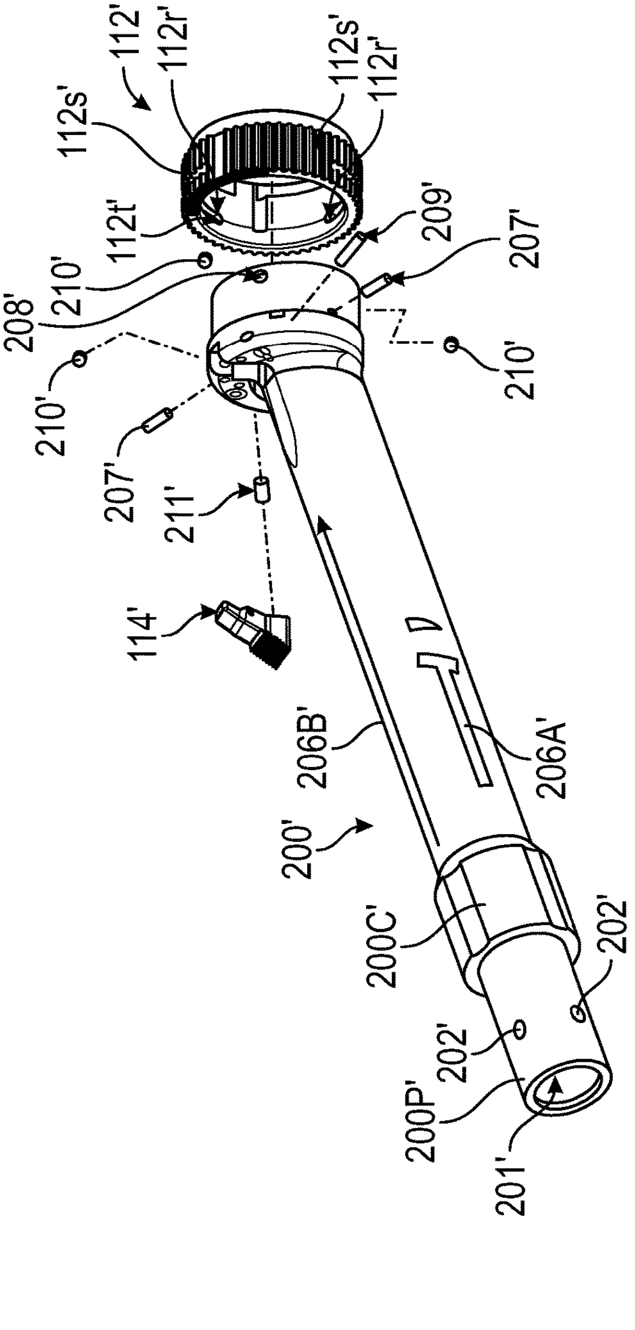
FIG. 32 is an exploded view of the full-wedge housing and the locking collar shown in FIG. 31.

FIG. 31 illustrates the full-wedge housing 108' with the locking collar 112' and locking lever 114' assembled to a distal end 108*d*' thereof. FIG. 32 shows an exploded view of the components in FIG. 31. The housing 108' can include an elongate shaft 200' extending from a proximal end 200*p*' to a distal end 200*d*', with a collar 200*c*' located closer to the proximal end 200*p*' than the distal end 200*d*'. A lumen or throughbore 201' can extend from the proximal end 200*p*' to the distal end 200*d*' of the elongate shaft 200'. The proximal end of the elongate shaft 200' can couple to the handle 106 in the same manner as described herein with reference to the half-wedge housing 108 and the half-wedge housing elongate shaft 200. To this end, the one or more detents 202' can be formed around a circumference of the proximal end 200*p*' of the elongate shaft. The detents 202' can be sized to receive ball bearings 612 of the handle 106.

Figure 33A:
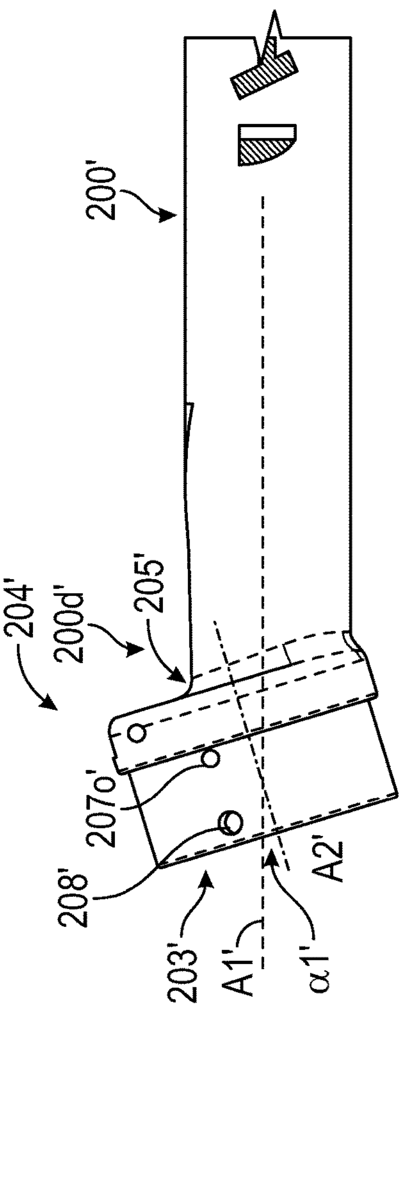
FIG. 33A is an enlarged side view of a distal end of the full-wedge housing of FIG. 31.
Figure 33C:
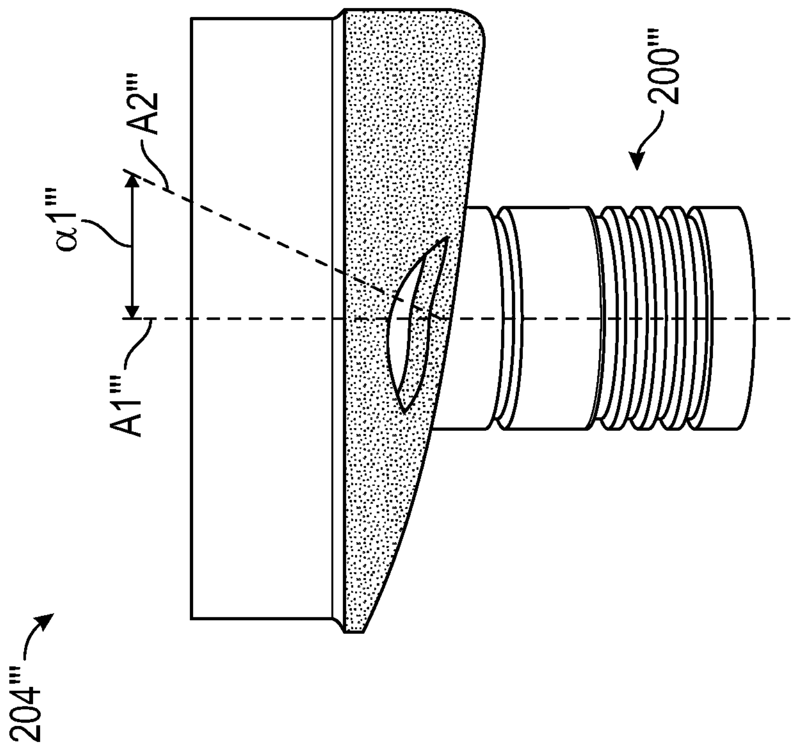
FIG. 33C is a side view of one exemplary embodiment of a half-wedge attachment portion.
Figure 33B:
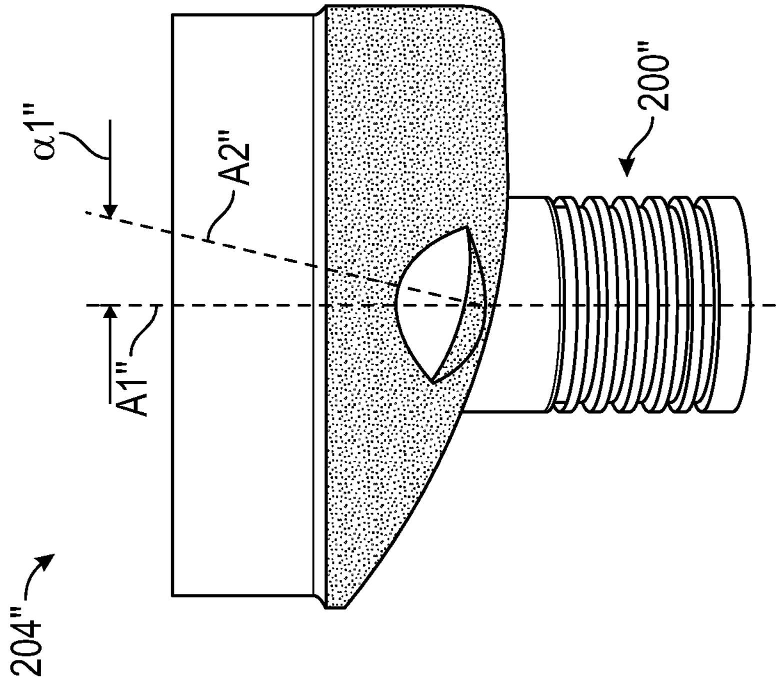
FIG. 33B is a side view of one exemplary embodiment of a full-wedge reamer attachment portion.

A reamer attachment 204' can extend from the distal portion 200*d*' of the elongate body 200'. FIG. 33A is an enlarged view of a distal of the elongate body 200*d*' and the reamer attachment 204'. FIGS. 33B and 33C illustrate two exemplary reamer attachments-full-wedge reamer attachment portion 204" and half-wedge reamer attachment portion 204", respectively-provided at least in part to illustrate example angles formed between reamer attachments or reamer attachment portions and an elongate shaft, 200" and 200", also respectively. To the extent portions of the reamer attachment portions 204", 204" and/or shafts 200", 200" are not labeled or illustrated, a person skilled in the art will understand the various features that can be included therein in view of the present disclosures and knowledge of the skilled person. For example, the illustrated reamer attachments 204" and 204'" can more generally be part of full-wedge housings and half-wedge housings, respectively, including but not limited to the housings 108' and 108, also respectively.

As shown in FIG. 33A, the reamer attachment portion 204' can have a bore 203' formed therein with a central longitudinal axis A2' that can extend at an oblique angle α1' relative to a central longitudinal axis A1' of the elongate shaft 200'. As noted above, the reamer attachment 204' of the full-wedge housing 108' can extend at a different oblique angle α1' than the reamer attachment 204 of the half-wedge housing 108. In some embodiments, the reamer attachment 204' of the full-wedge housing 108' can extend at a smaller or more acute angle α1' than the reamer attachment 204 of the half-wedge housing. This can align a reamer head 110 (not shown) when assembled to the full-wedge housing 108' to ream a bone surface with a proper geometry to accept a full-wedge implant. By way of non-limiting example, the reamer attachment 204' of the full-wedge housing 108' can extend at an angle α1' approximately in the range of about 15 degrees (the 15 degree angle also being illustrated by an oblique angle α1" formed by a central longitudinal axis A1" of the elongate shaft 200" and a central longitudinal axis A2" of the reamer attachment 204" in FIG. 33B) to about 17 degrees, while the reamer head 204 of the half-wedge housing 108 can extend at an angle α1 approximately in the range of about 22 degrees (the 22 degree angle also being illustrated by an oblique angle α1" formed by a central longitudinal axis A1" of the elongate shaft 200'" and a central longitudinal axis A2" of the reamer attachment 204" in FIG. 33C) to about 29 degrees. Other angular measurements are possible. A person skilled in the art will appreciate these narrow angle ranges are merely exemplary and that larger angle angles are possible. For example, greater angle values can be achieved if cutter features eliminate interference, but a person skilled in the art will appreciate a trade-off exists between how much bone is left behind for a user to manually remove. A filet 205' can be formed between the distal end 200*d*' of the elongate body 200' and a top portion 204' of the reamer attachment 204'. This can transition the housing 108' from the elongate body 200' to the obliquely angled reamer attachment 204'. A radius of the filet 205' can differ from a radius of the filet 205 of the half-wedge housing 108, which can result in the differing angles at which the reamer attachment 204', 204 can extend from the elongate body 200', 200. One or more visual indicators, 206A', 206B' can be placed on the housing 108' to signal to a user that the housing 108' is appropriate for preparation of a bone surface to receive a full-wedge implant.

A hollow cylindrical body 204*b*' can extend distally from the top portion 204*a*'. A locking collar 112' can be located around the hollow cylindrical body 204*b*' and coupled to the reamer attachment 204' as described herein in connection with the half-wedge housing 108. The locking collar 112' and locking lever 114' can have similar construction and operation to the locking collar 112 and the locking lever 114 as described herein in connection with the half-wedge housing 108. Briefly, one or more dowels 207' can extend from the cylindrical body 204*b*' of the reamer attachment 204' and can each be received within a slot 112*s*' of the locking collar 112'. Ball bearings 210' can be received within through holes 208' in the cylindrical body 204*b*'. The ball bearings 210' can align with a track 112*t*' of the locking collar 112' and can slide or move along ramps 112*r*' of the track 112*t*' with rotation of the locking collar 112' to selectively lock or unlock a reamer head 110' (not shown) from the reamer attachment 204'.

Figure 38:
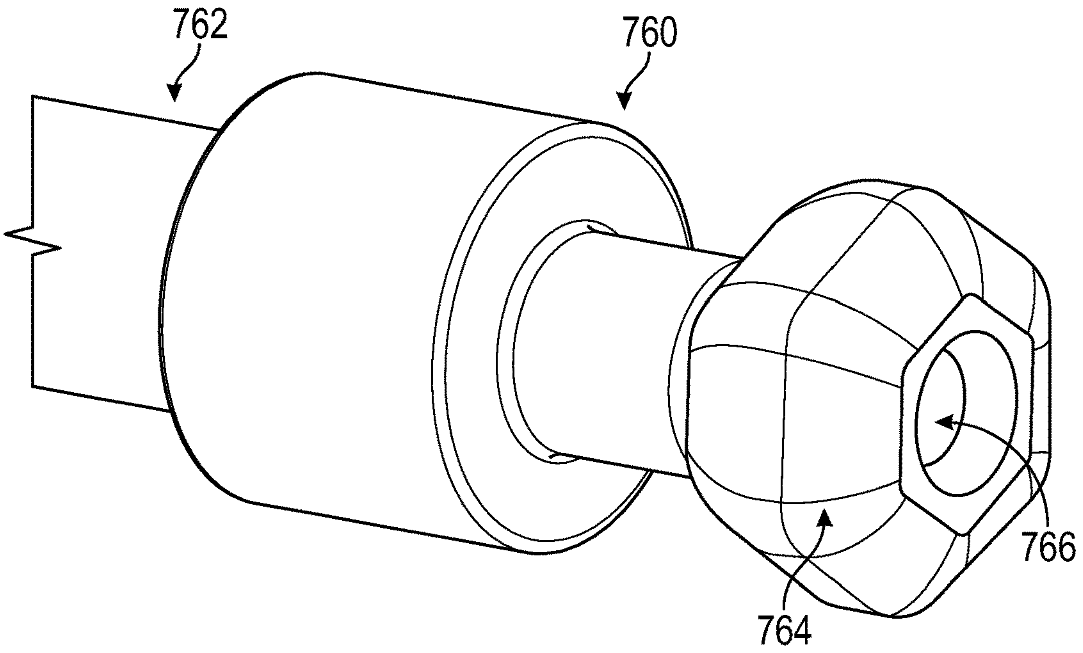
FIG. 38 is a perspective view of another embodiment of a drive tip in accordance with the present disclosure.
Figure 39:
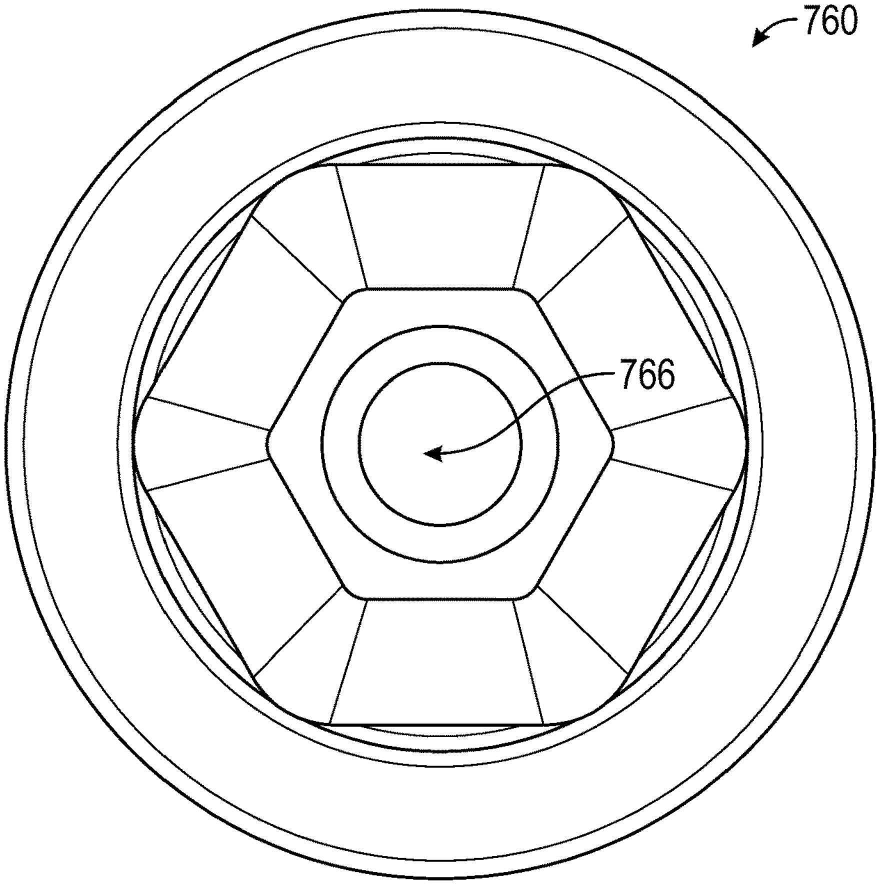
FIG. 39 is a front-view of the drive tip of FIG. 38.

FIGS. 34-37 illustrate alternative embodiments of reamer heads 700, 720, 740 of the present disclosure that can be used to prepare bone to receive an implant. FIGS. 38 and 39 illustrate an alternative embodiment of a drive tip 760 that can drive the reamer heads 700, 720, 740 of FIGS. 34-37. As discussed in detail below, the reamer heads 700, 720, 740 can each have a female hex feature. The drive tip 760 can have a male hex shaft that can couple with the female hex feature of the reamer heads 700, 720, 740 to transfer rotational torque to the reamer head. These configurations of reamer heads and drive tips are non-limiting embodiments of configurations for reamer heads and drive tips.

Figure 34:
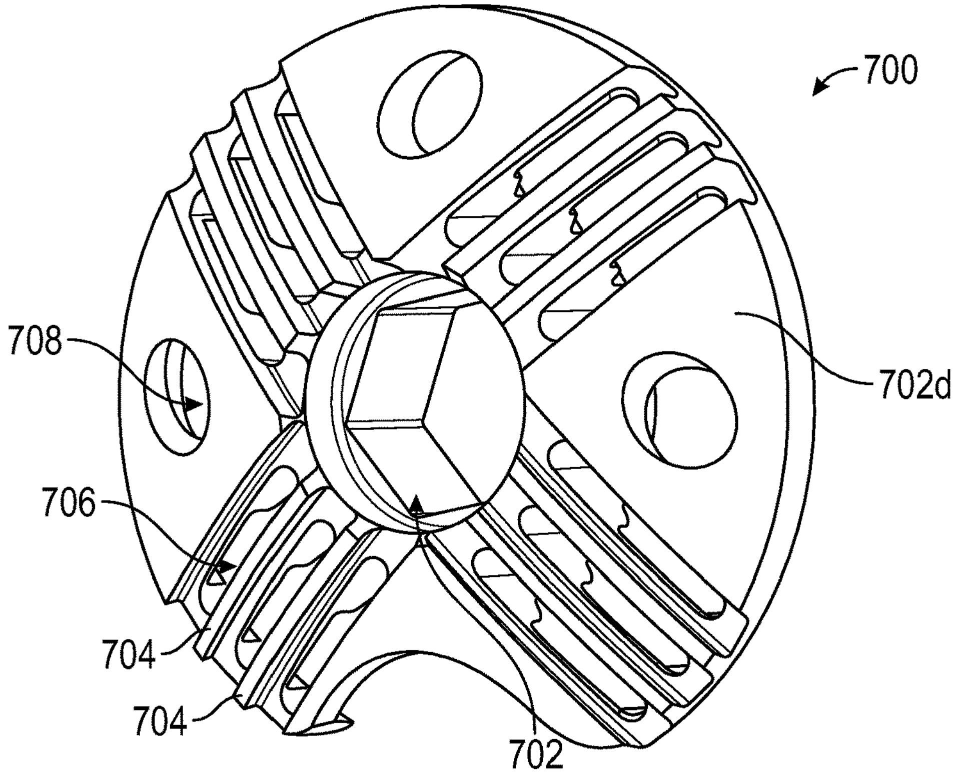
FIG. 34 is a perspective front-view of another embodiment of a reamer head in accordance with the present disclosure.
Figure 35:
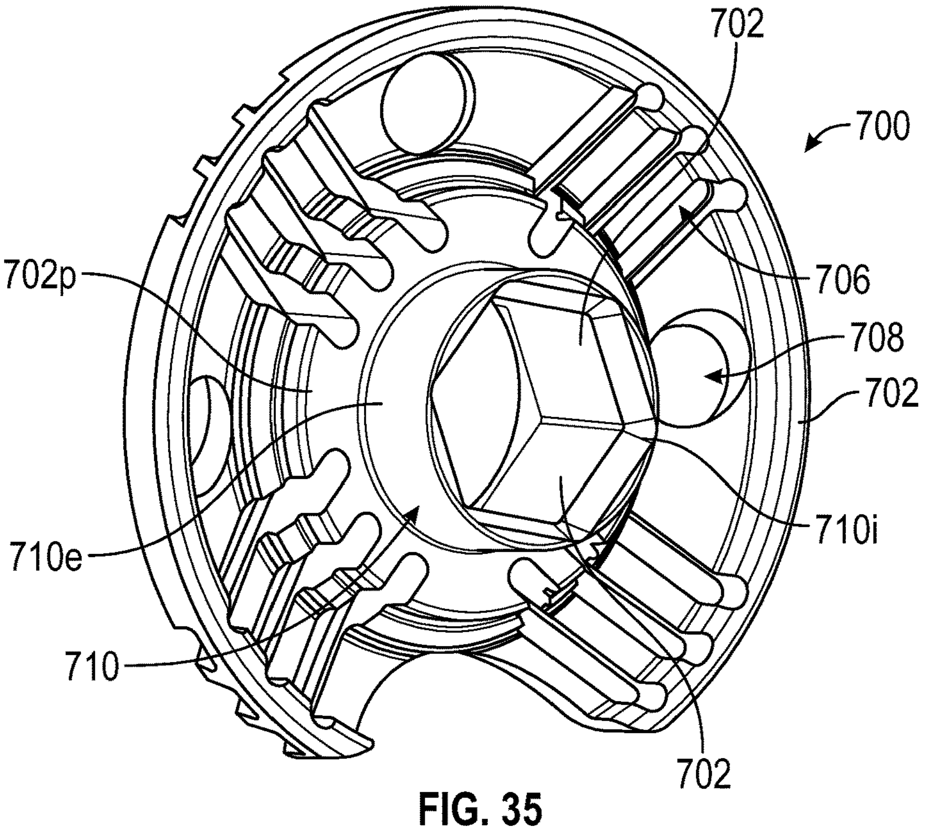
FIG. 35 is a perspective back-view of the reamer head of FIG. 34.

FIGS. 34 and 35 show one embodiment of a reamer head 700 with a female hex drive feature 702. The reamer head 700 can have a top cutting head 702 with a plurality of blades 704. In this manner, a distal facing surface 702*d* of the cutting head 702 can ream or cut bone. A profile of the distal facing surface 702*d* can match a spherical radius of an implant to be received by a bone surface to be reamed. Each blade 704 can be biased such that the blade only cuts into a bone surface with its sharp edge upon rotation in a first direction, e.g., clockwise. Rotation of the reamer head 700 in a second direction, opposite the first direction, can cause each blade 704 to contact a bone surface only with a blunt edge. One or more slots 706 and/or one or more holes 708, i.e., debris-relief openings, can extend through the cutting head 702. Each of the one or more slots 706 can be adjacent to at least one blade 704. The female hex drive feature 702 can be formed in a hollow body 710 that can extend proximally from a proximal facing surface, i.e., a non-cutting surface, of the cutting head 702. An external surface 710*e* of the body 710 can be a cylindrical or substantially cylindrical shape. An internal surface 710*i* of the body 710 can have a hexagonal or substantially hexagonal shape and can form the female hex drive feature 702. The female hex drive feature 702 can also be referred to as an engagement aperture and can be a throughbore formed through the reamer head 700. A central longitudinal axis B1 can extend longitudinally through the engagement aperture 702.

Figure 36:
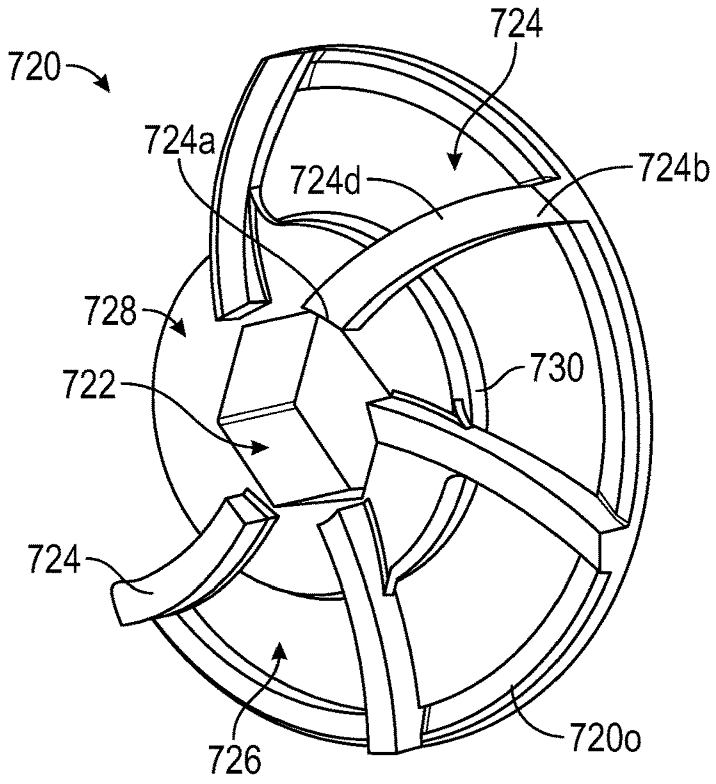
FIG. 36 is a perspective front-view of another embodiment of a reamer head in accordance with the present disclosure.

FIG. 36 illustrates another embodiment of a reamer head 720 with a female hex drive feature 722. The reamer head 720 can have a plurality of blades 724 with openings or slots 726, i.e., debris-relief openings, formed therebetween. Each blade 724 can extend from a first end 724*a* formed on a central body 728 to a second end 724*b* formed on an outer rim 7200. The outer rim 7200 can extend in a circular path between the second ends 724*b* of adjacent blades 724. In the illustrated embodiment, the reamer head 720 has five blades 724 that can be spaced apart about a circumference of a partial circle. The central body 728 can have a cylindrical or generally cylindrical shape and can extend proximally relative to a distal-facing cutting surface 724*d* of the blades 724. The female hex drive feature 722 can be formed through the central body 728. More particularly, a hexagonally shaped lumen or throughbore can extend through the central body 728 such that an internal wall of the central body can have a hexagonal or substantially hexagonal shape. A central longitudinal axis B1' can extend longitudinally through the throughbore of the central body 728, i.e., through the female hex drive feature 722. A snap ring 730 can be seated in a shoulder or groove 732 (see FIG. 40) formed in the central body 728. As discussed in detail below, the snap ring 730 can aid in coupling the reamer head 720 to a reamer attachment of a reamer instrument.

Figure 37:
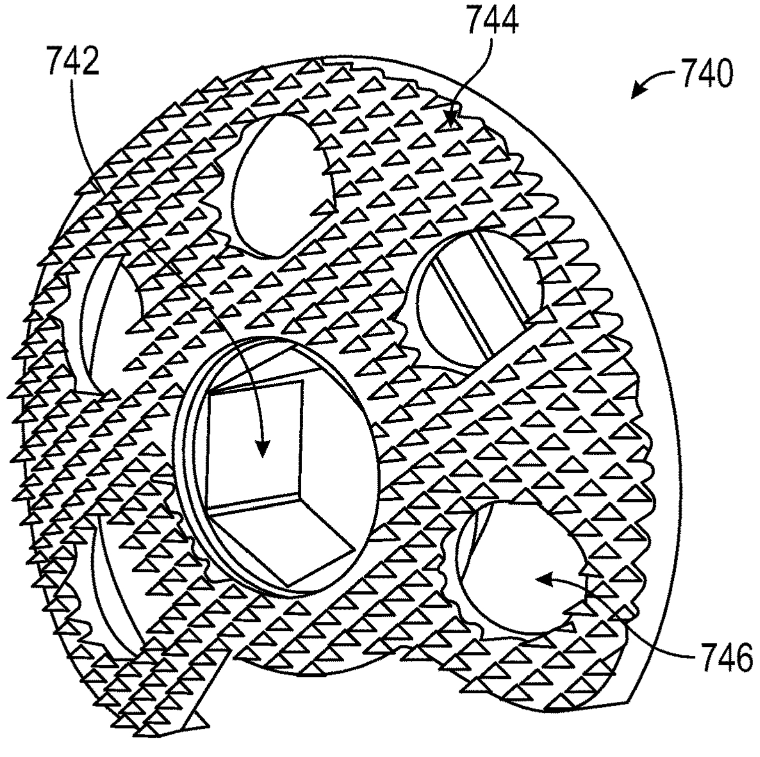
FIG. 37 is a perspective front-view of another embodiment of a reamer head in accordance with the present disclosure.

FIG. 37 illustrates another embodiment of a reamer head 740 with a female hex drive feature 742. The reamer head 740 can have a cutting head or top 742 that can remove bone material, e.g., for filing. In the illustrated embodiment, the cutting head 742 can have a plurality of sharp elements, such as ridges or points 744, that can extend from a distal-facing cutting surface 742*d* of the cutting head 742. The sharp elements can cover or substantially cover the entirety of the distal-facing cutting surface. A plurality of holes 746, i.e., debris-relief openings, can extend through the cutting head 742. The holes 746 can reduce a weight of the reamer head 740 and can also allow bone or other debris to move away from a working surface by passing through the holes 746. The female hex drive feature 742 can be formed through a central body that can extend proximally from a proximal-facing surface of the cutting head 742. A lumen or through-bore in the shape of a hexagon can extend through the central body such that an inner wall of the central body can have a hexagonal or substantially hexagonal shape. The central body and female hex drive feature 742 can be similar to the central body 710 and female hex drive feature 702 described above in connection with FIGS. 35 and 36.

FIGS. 38 and 39 illustrate one embodiment of a drive tip 760 that can drive any of the reamer heads 700, 720, 740 described in connection with FIGS. 34-37. The drive tip can have a barrel portion 762 with a hexagonal drive feature 764 formed at a distal end of the shaft. The hexagonal drive feature 764 and barrel portion 762 can be cannulated, i.e., can have a lumen or throughbore 766 extending there-through. The drive tip 760 can be coupled to a distal end of an elongate shaft to form a full drive shaft, e.g., by connection or coupling features as described herein with respect to drive tip 102 and elongate shaft 104*e*. In this manner, the drive tip 760 can be a single-use component while the elongate shaft can be reusable. In other embodiments, the drive tip 760 can be integrally formed with an elongate shaft to form a full drive shaft.

Figure 40:
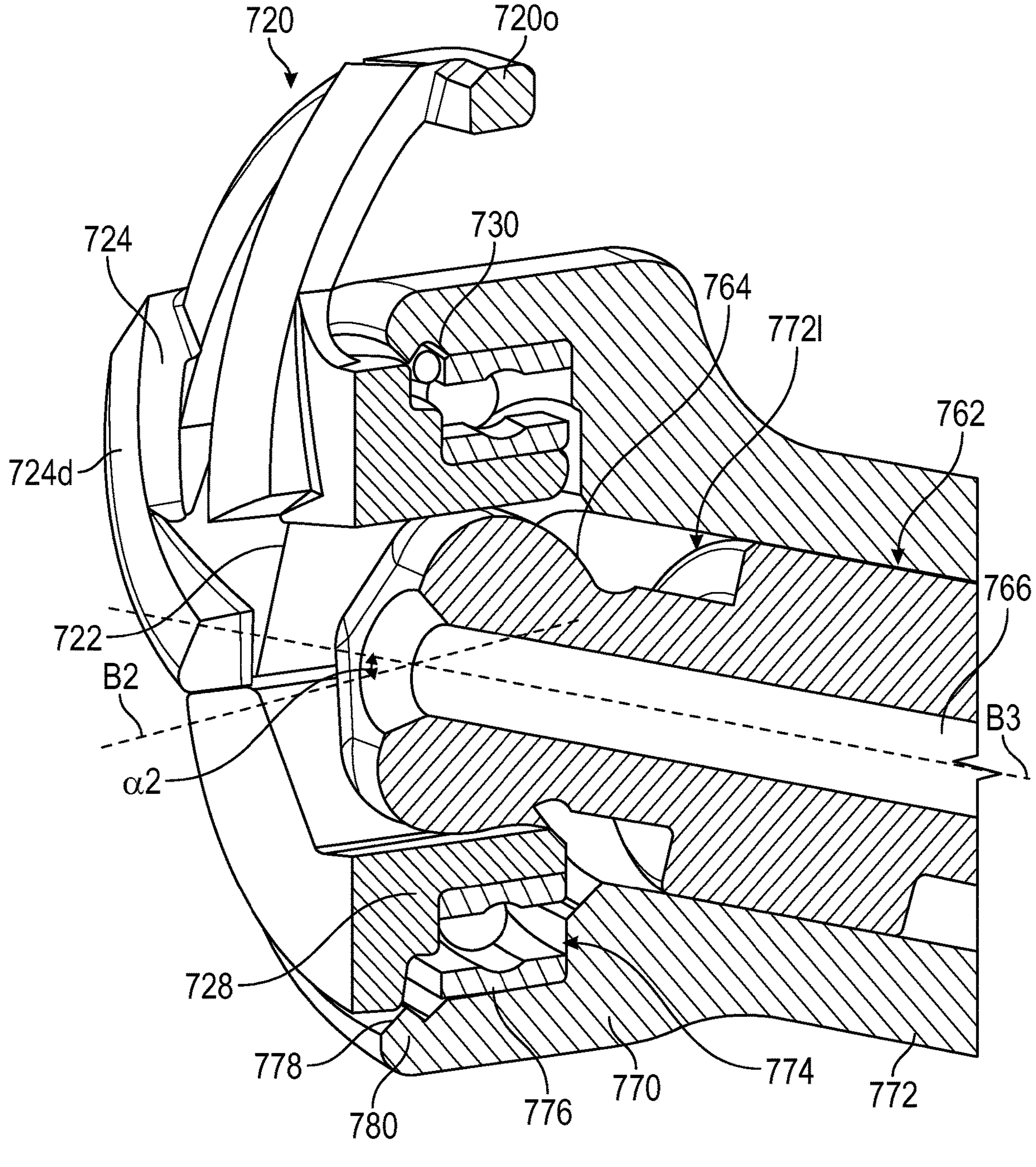
FIG. 40 is a cross-sectional view of a distal end of another reamer instrument in accordance with the present disclosure, the reamer instrument including the drive tip of FIG. 38 and the reamer head of FIG. 36.

FIG. 40 is a cross-sectional view of the reamer head 720 of FIG. 37 coupled to a reamer attachment 770 at a distal end 772*d* of a housing elongate body 772. The elongate body 772 can be part of a reamer instrument that can be used to ream or prepare a bone surface for receiving an implant. One skilled in the art will appreciate how the construction, assembly, and use of the components illustrated in FIG. 40 and described herein can be assembled and used with various other components of reamer instruments of the present disclosure, e.g., a handle 106, drill connection 120, and elongate shaft 200, 200' of a housing. The same is true for other embodiments of heads, tips, and other components provided for herein and/or otherwise derivable from the present disclosures. The reamer attachment 770 can extend at an oblique angle α2 from a distal end 772*d* of an elongate shaft. More particularly, the reamer attachment 770 can have a cylindrical body 770*b* with a bore 774 formed therein. A central longitudinal axis B2 of the cylindrical body bore 774 can extend at an oblique angle α2 relative to a central longitudinal axis B3 of the elongate shaft 772. A cylindrical roller bearing 776 can be received within the bore 774. The cylindrical roller bearing 776 can have a central opening into which the central body 728 of the reamer head 720 can be received.

The central body 728 can be inserted into the bore 774 such that the blades 724 and outer rim 7200 can extend distally from the reamer attachment 770. A lip 778 can form a distal opening of the bore 774, which can have a diameter slightly less than a resting diameter of the reamer head snap ring 730. When the reamer head 730 is inserted into the reamer attachment 770, the snap ring 730 can radially compress to allow passage of the snap ring 730 into the bore 774. A groove 780 can be formed proximally of the lip 778. The groove 780 can have a diameter equal to or greater than the snap ring 730. Accordingly, when the snap ring 730 axially aligns with the groove 780, the snap ring can radially expand to its resting diameter and be retained within the groove 780. This can retain the reamer head 720 securely within the bore 774 of the reamer attachment 770 such that the female hex drive feature 722 extends co-axially with the central longitudinal axis B2 of the bore 774.

The drive tip 760 can extend through the throughbore 7721 of the housing 772 such that the drive tip 764 can extend into the bore 774 of the reamer attachment 770 and can be received within the female hex drive feature 722 of the reamer head 720. The drive tip 760 can mate with the female hex drive feature at the same oblique angle α2 that can extend between the longitudinal axis B2 of the bore 744 and the longitudinal axis B3 of the housing 772. Accordingly, the hexagonal drive tip 764 can contact the hexagonal walls that form the female hex drive feature 722 at an oblique angle at multiple points of contact. This interference can transfer rotational torque of the drive tip 764 to the reamer head 720, which can cause the reamer head 720 to rotate relative to the reamer attachment 770 to cut into a bone surface.

FIGS. 41-54 illustrate one embodiment of a method of assembling a reamer instrument, e.g., the reamer instrument 100 illustrated in FIG. 1, in accordance with the present disclosure.

Figure 41:
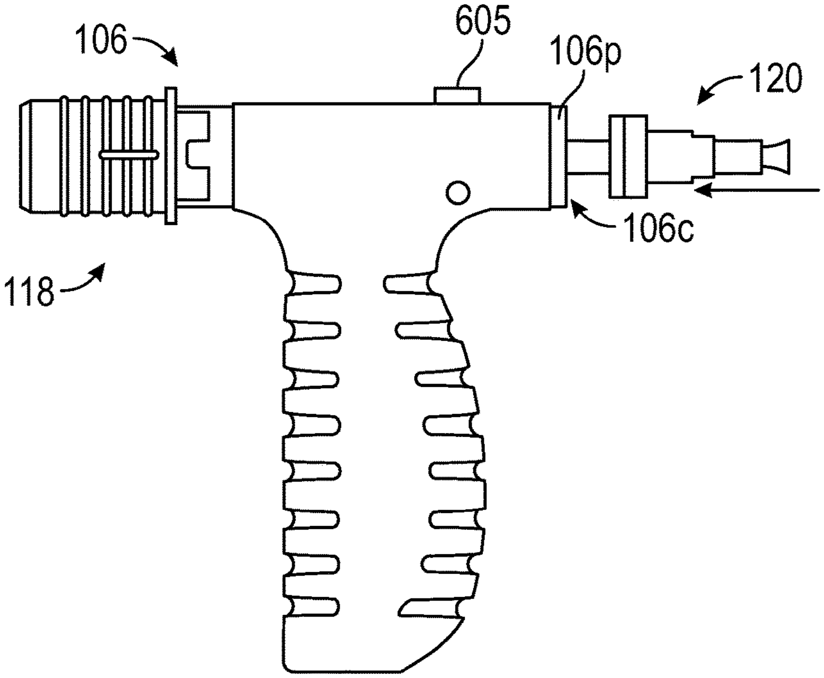
FIGS. 41-47 are sequential view illustrating one embodiment of assembling the reamer instrument of FIG. 1.

The drill connection 120, e.g., a Hudson connector, can be inserted into the proximal end 106*p* of the handle 106 (see FIG. 41). The first end 120*a* of the drill connection 120 can be inserted into the handle of the throughbore 1061 through the handle bushing 600*b*. The drill connection 120 can be fully inserted when the washer 122 is seated within the bushing flange 600*bf* and the notch 605*n* of the release button 605 engages with the groove 120*g* of the drill connection 120 (see, e.g., FIG. 29). The release button 605 can axially restrict movement of the drill connection 120 within the handle 106 while permitting relative rotation therebetween.

Figure 42:
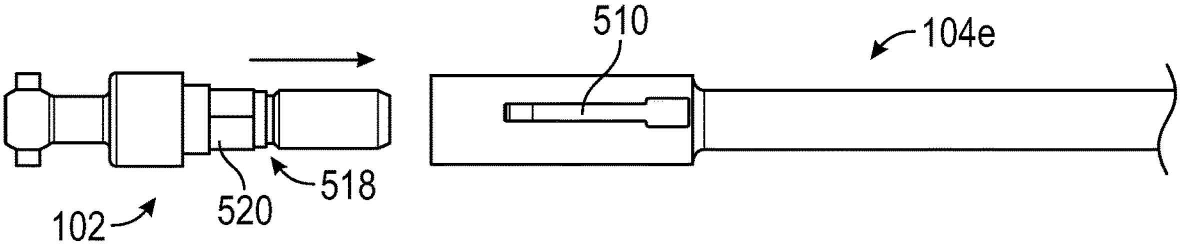

The drive shaft 104 can be assembled by securely coupling the distal pin drive tip 102 to the elongate shaft 104*c*. As shown in FIG. 42, in some embodiments, this can be accomplished by aligning the distal pin drive tip 102 with the distal end of the elongate shaft 104*ed*. The drive tip 102 and the elongate shaft 104 can be moved towards one another until the drive tip 102 is securely engaged with the distal end of the elongate shaft 104*ed*. The proximal end of the drive tip 102*p* can be inserted into the elongate shaft 104 such that the external hex feature 520 of the drive tip 102 couples with the internal hex feature 508 of the elongate body 104*c*. Tactile and/or audial feedback can be provided upon engagement of the drive tip 102 and elongate shaft 104*e*, which can alert the user that the drive tip 102 is securely received within the elongate shaft 104*c*. For example, an audible click or snap can be heard when the fingers 510 of the elongate shaft 104*e* engage with the groove 518 of the drive tip (see, e.g., FIG. 23B). With the drive shaft 104 assembled, the inner lumen, throughbore, or cannulation 500*b* of the drive tip 102 can align and be co-axial with the inner lumen, throughbore, or cannulation 500*a* of the elongate shaft 104*c*. Accordingly, the drive shaft 104 can have a cannula or inner lumen 500 that can extend the entire length of the drive shaft, from the proximal end of the elongate shaft 104*ep* to the distal end of the drive tip 102*d*, without obstruction. One skilled in the art will appreciate that while the drive shaft 104 described herein can have a two-piece construction, i.e., the disposable drive tip 102 and the reusable elongate shaft 104*e*, in other embodiments the drive shaft 104 can have a greater or fewer number of components. For example, the drive shaft 104 can be a single piece drive shaft.

The proximal end 104*p* of the drive shaft 104 can be coupled to the handle 106. Further, the proximal end 104*p* of the drive shaft 104 can be inserted proximally into the distal end 106*d* of the handle 106, i.e., through the inner throughbore 604*l* of the intermediate handle portion 604. The quick-release collar 118 can be pulled or translated proximally to move the release collar 118 into the retracted position (see, e.g., FIG. 30A). With the release collar 118 in its resting or locked position (see, e.g., FIG. 30B), the handle ball bearings 612 can extend through the distal end 604*d* of the intermediate handle portion 604 and into the throughbore 604*l* by an amount such that a diameter of the throughbore 604*l* can be less than a diameter of the collar lip 5041 on the elongate body 104*c* of the drive shaft 104. Accordingly, coupling or uncoupling of the drive shaft 104 to the handle 106 can be prevented when the release collar 118 is in the locked position.

With the release collar 118 in the retracted position, the drive shaft 104 can be inserted proximally through the throughbore 1061 of the handle until the proximal end 104*p* of the drive shaft 104 until it bottoms out, i.e., can no longer be moved proximally within, the handle 106. This can occur when the proximal end 104*p* of the drive shaft 104 is fully received within the enlarged bore 120*e* at the first end 120*a* of the drill connection 120 (see, e.g., FIG. 29). The release collar 118 can be released, which can return the release collar 118 to the locked or resting position and can prevent the drive shaft 104 from being removed from the handle 106. The throughbore 1201 of the drill connection 120 can align with the inner throughbore 500 of the drive shaft 104 such that a continuous lumen, throughbore, or cannulation extends from the second end 120*b* of the drill connection 120 to the distal end 120*d* of the drive shaft 104. While commonly the proximal end 104*p* of the drive shaft 104 can be assembled into the handle 106 following coupling of the drive tip 102 to the elongate shaft 104*e*, one skilled in the art will appreciate that the elongate shaft 104*e* can be assembled to the handle 106 as described above and the drive tip 102 can be subsequently coupled to the elongate shaft 104*e* to assemble the complete drive shaft 104.

Figure 43:
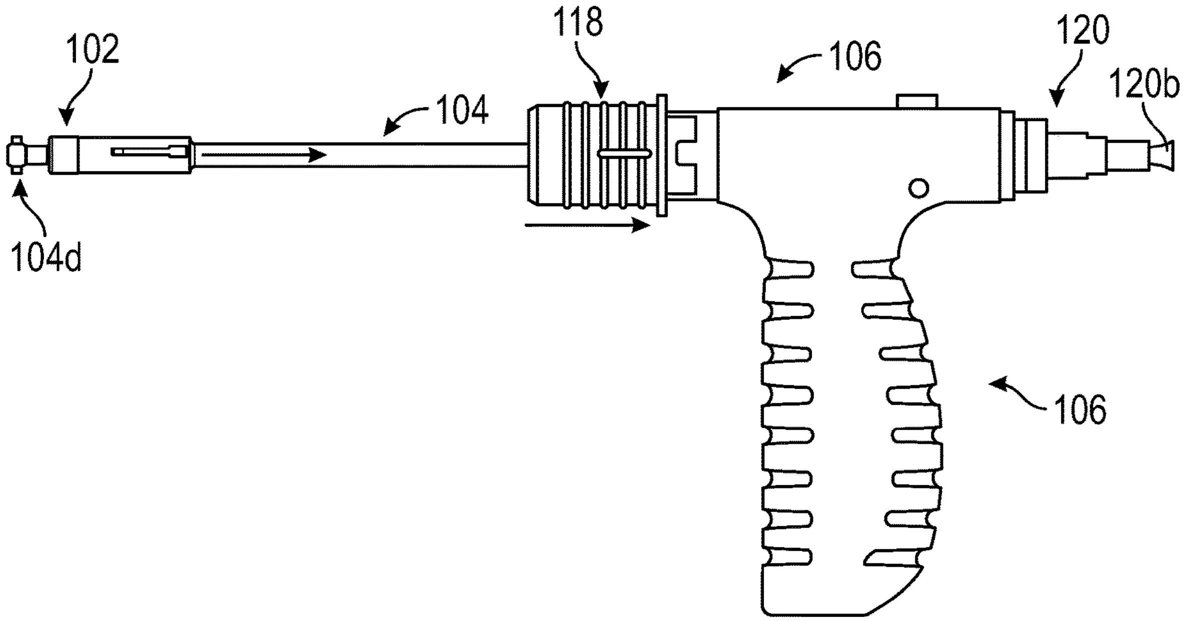
Figure 44:
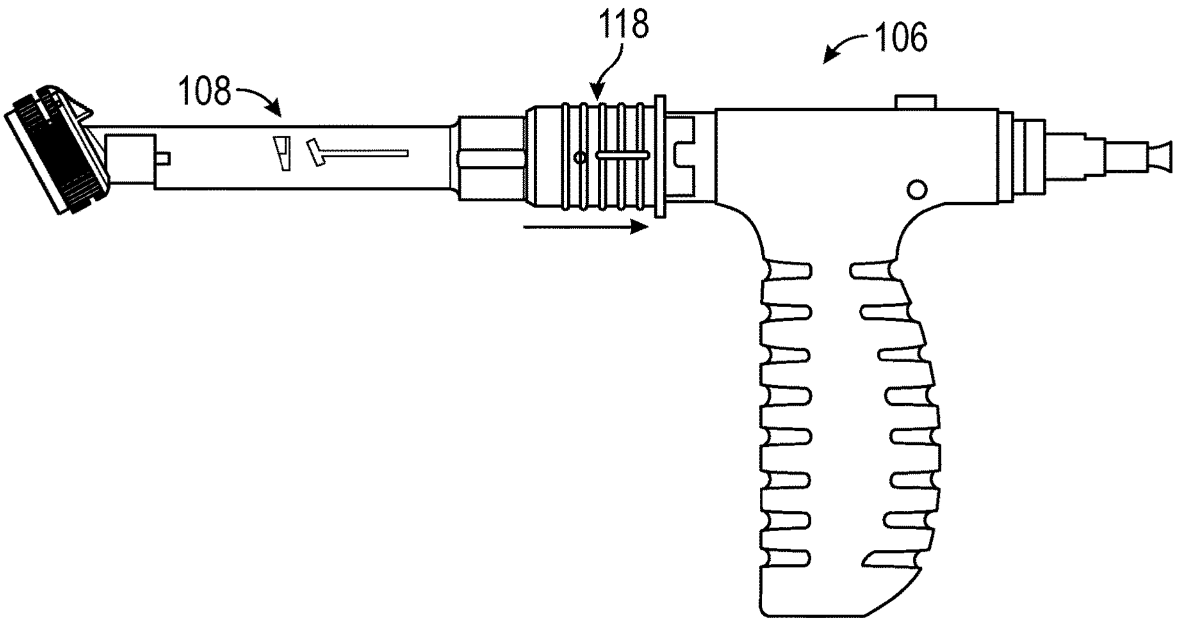
Figure 45:
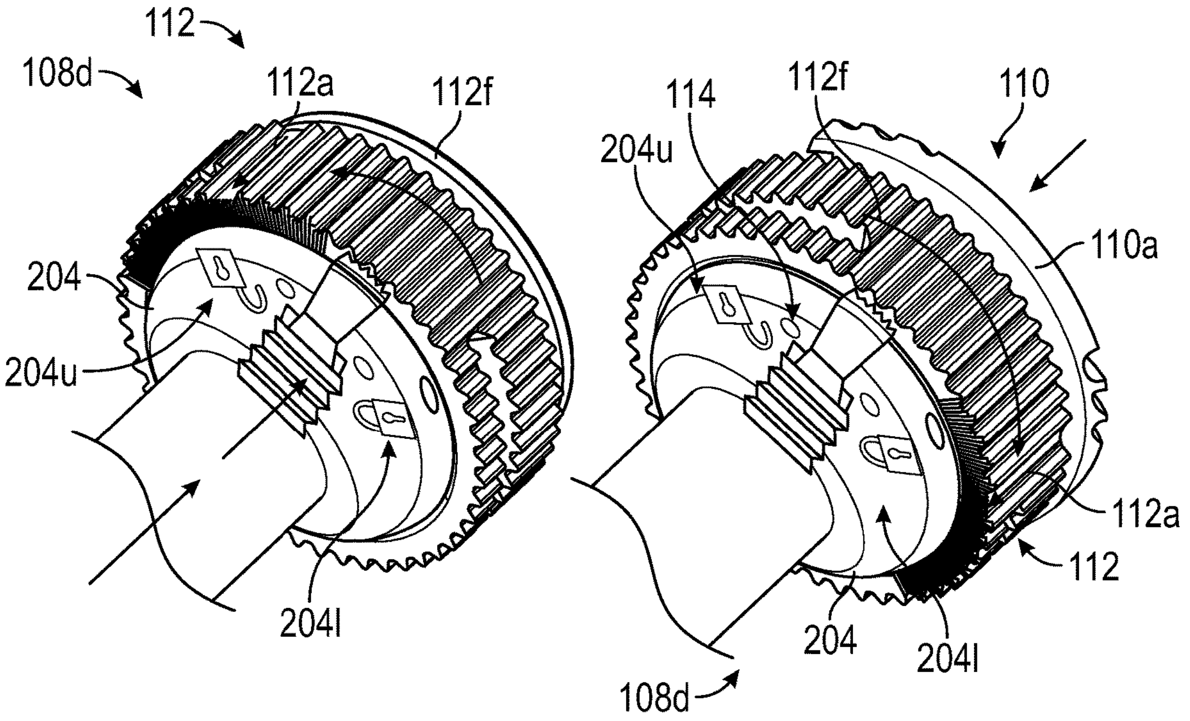

The half-wedge or full-wedge housing 108, 108' can be slid over the drive shaft and coupled to the handle 106. It will be appreciated that either the half-wedge or the full-wedge housing will be selected for assembly of the reamer instrument based, at least in part, on the needs of the particular surgery and/or preferences of the surgeon. FIG. 43 illustrates one embodiment of coupling the half-wedge housing 108 to the handle 106, while FIG. 50 (discussed in detail below) illustrates one embodiment of coupling the full-wedge housing 108' to the handle 106.

As shown in FIG. 43, the housing 108 can be slid over the drive shaft 104, such that the drive shaft 104 can extend through the throughbore 201 of the housing 108, and couple to the distal end 106*d* of the handle 106. Insertion of the proximal end 108*p* of the housing 108 into the distal end 106*d* of the handle 106 can be enabled by retracting the quick-release collar 118 proximally to place the collar in the unlocked position (see, e.g., FIG. 30A). The proximal end 108*p* of the housing 108 can be inserted into the distal end 106*d* of the handle 106 and, more particularly, can be inserted into the distal end of the throughbore 604*l* of the intermediate portion of the handle until the housing 108 can no longer be moved proximally. With the housing 108 in the fully inserted position, the collar 504*c* of the drive shaft 104 can be received within the throughbore 201 of the housing 108 and the housing detents 202 can be axially aligned with the openings 610 of the intermediate handle portion 604. The drive shaft 104 can extend through the housing 108 such that the drive tip 102 can extend into the bore 203 of the reamer attachment portion 204 of the housing 108. The quick release collar 118 can be returned to its resting or locked position, e.g., by releasing the collar body 614 from the retracted position which can restrict axial and/or rotational movement between the housing 108 and the handle 106.

The housing 108 can be coupled to the handle 106 in one of a plurality of positions to achieve a desired orientation, as selected or determined by a user based on, for example, defect location, whether operating on the left or right side of the patient, dominant hand of the user, etc. For example, the plurality of positions can be in 90 degree increments such that the housing 108 can be coupled to the handle in one of four orientations. One skilled in the art will appreciate that a greater or fewer number of possible positions and/or a different increment between the positions falls within the scope of the present disclosure. With the housing 108 fully inserted into the handle 106 and the quick-release collar 118 in the retracted position, the housing 108 can be rotated such that the housing detents 202 can align with an opening 610 in in the intermediate handle portion 604 adjacent to an initial opening 610 with which a housing detent 202 aligned when inserted into the handle 106. In other words, the housing 108 can be rotated relative to the longitudinal axis of the reamer instrument to re-align the housing detents 202 with the openings 610 in the handle and the ball bearings 612 received therein. Adjusting the number and/or spacing of the housing detents 202 and/or openings 610 with ball bearings 612 can adjust the number and orientation of possible positioning of the housing 108 relative to the handle 106. The quick release collar 118 can be released to its resting position once a desired orientation between the housing 108 and the handle 106 is achieved.

The locking collar 112 located at the distal end of the housing 108*d*, more particularly, around the reamer attachment 204, can be placed in the unlocked position to receive the reamer head 110. To this end, the locking lever 114 can be depressed, which can disengage the locking lever teeth 114*t* from the external surface 112*e* of the locking collar. The grip 114*g* of the locking lever 114 can be pushed towards the top 204*a* of the reamer attachment 204 such that the teeth 114*t* of the locking lever 114 pivot away from the locking collar 112 and can disengage from the ridges on the external surface 112*e* thereof. The locking collar 112 can be rotated in a first direction, e.g., counter-clockwise, to the unlocked position. As described herein, the unlocked position of the locking collar 112 can move the ball bearings 210 radially outwards, which can allow insertion of the head 110 within the locking collar 112. The rotational position of the locking collar 112 relative to the reamer attachment 204 in the unlocked position can be indicated to a user when the indicator arrow 112*a* of the locking collar 112 is brought into alignment with an unlocked symbol, such as the open lock 204*u*, on the top 204*a* of the reamer attachment 204. In the unlocked position, each dowel pin 207 can be located at a first end 112*s*' of the respective slot 112*s* in the locking collar 112.

The reamer head 110 can be inserted proximally into the distal end of the housing 108. More particularly, the outer bearing 110*b* of the reamer head 110 can be moved proximally into the bore 203 formed in the reamer attachment 204. The reamer head 110 can be inserted proximally into the housing 108 until the reamer head 110 is fully seated, with the cutting head 110*a* of the reamer head extending distally from the housing 108. As can be seen in FIGS. 25 and 26, the drive tip 102 can extend into the engagement aperture 304 of the reamer head 110 when the reamer head 110 is fully seated within the housing 108. The drive pins 522*a*, 522*b* can each contact an engagement post 306*a*, 306*b* of the reamer head 110 such that rotation of the drive tip 102 in a first direction can cause rotation of the reamer head 110 in the first direction.

A user can visually confirm full seating of the reamer head, for example, when the laser line on the locking collar flange 1121 is obstructed by the cutting head 110*a*. With the reamer head 110 fully seated, the locking collar can be rotated in a second direction opposite the first direction, e.g., clockwise, which can cause the ball bearings 210 to slide along the ramps 112*r* in the locking collar and move radially inwards. This, in turn, can exert a radial compression force on the outer bearing 110*b* of the reamer head 110 and secure the reamer head 110 within the reamer attachment 204 of the housing 108. Rotation of the locking collar 112 in the second direction to the locked position can occur without depression of the locking lever 114. Audible and/or haptic feedback can be provided to the user while rotating the locking collar in the second direction such that the user can hear and feel when the locking collar is in the locked position. For example, the user can hear clicks and feel a ratcheting sensation while rotating the locking collar 112 in the second direction until the ratcheting is complete, which can indicate that the locking collar is in the locked position and the reamer head securely locked to the housing. Visually, a user can identify when the locking collar 112 is in the locked position when the locking collar arrow indicator 112*a* aligns with the locked indicator 1121 on the reamer attachment 204. Each dowel pin 207 can be located at a second end 112*s*" when the locking collar is in the locked position (see, e.g., FIG. 8).

Figure 46:
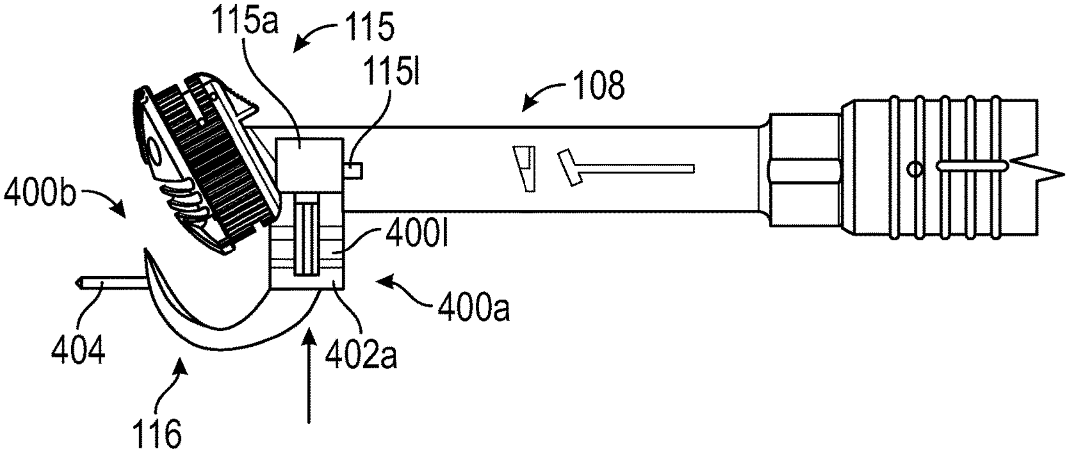

FIG. 46 illustrates attachment of the depth stop 116 to the housing 108. In at least some instances, the depth stop 116 can be coupled to the housing 116 after the reamer head is secured to the distal end of the housing. The depth stop 116 can be attached to the housing at the pre-machined location 115 that can properly position the depth stop 116 with respect to the reamer head 110 such that a bone surface can be prepared with a desired and intended geometry, i.e., to the geometry to accept a half-wedge metaglene implant. When properly positioned, the longitudinal axis of the depth stop guide pin 404 can extend substantially parallel to the longitudinal axis of the elongate body 200 of the housing 108. The depth stop 116 can be positioned at the pre-machined location 115 on the housing 108 such that the arms 402*a*, 402*b* of the depth stop 116 can be aligned with the recessed flats 115*a*, 115*b* on either side of the housing 108 at the pre-machined location 115. The depth stop 116 can be moved towards the housing 108 and each arm 402*a*, 402*b* can be received within a recessed flat 115*a*, 115*b*, e.g., with a snap-fit connection, and the stop guard end 400*b* of the depth stop 400 can extend distally of the reamer attachment 204 and the reamer head 110. Visual indicators on the housing 108 and the depth stop 116 can indicate to the user that the depth stop 116 is properly and fully coupled to the housing 108. For example, horizontal lines 4001 can extend across one or both arms 402*a*, 402*b* of the depth stop 116. These lines 4001 can be axially aligned with a horizontal line 1151 that can extend proximally from the pre-machined location 115 on one or both sides of the housing (only one side of the housing is visible in FIG. 46) when the depth stop 116 is fully seated within the pre-machined location 115 of the housing 108. The depth stop 116 can be designed for easy attachment, for example, with a single hand and can provide a mating fit with the housing 108 that can restrict movement between the depth stop 116 and the housing 108.

Figure 47:
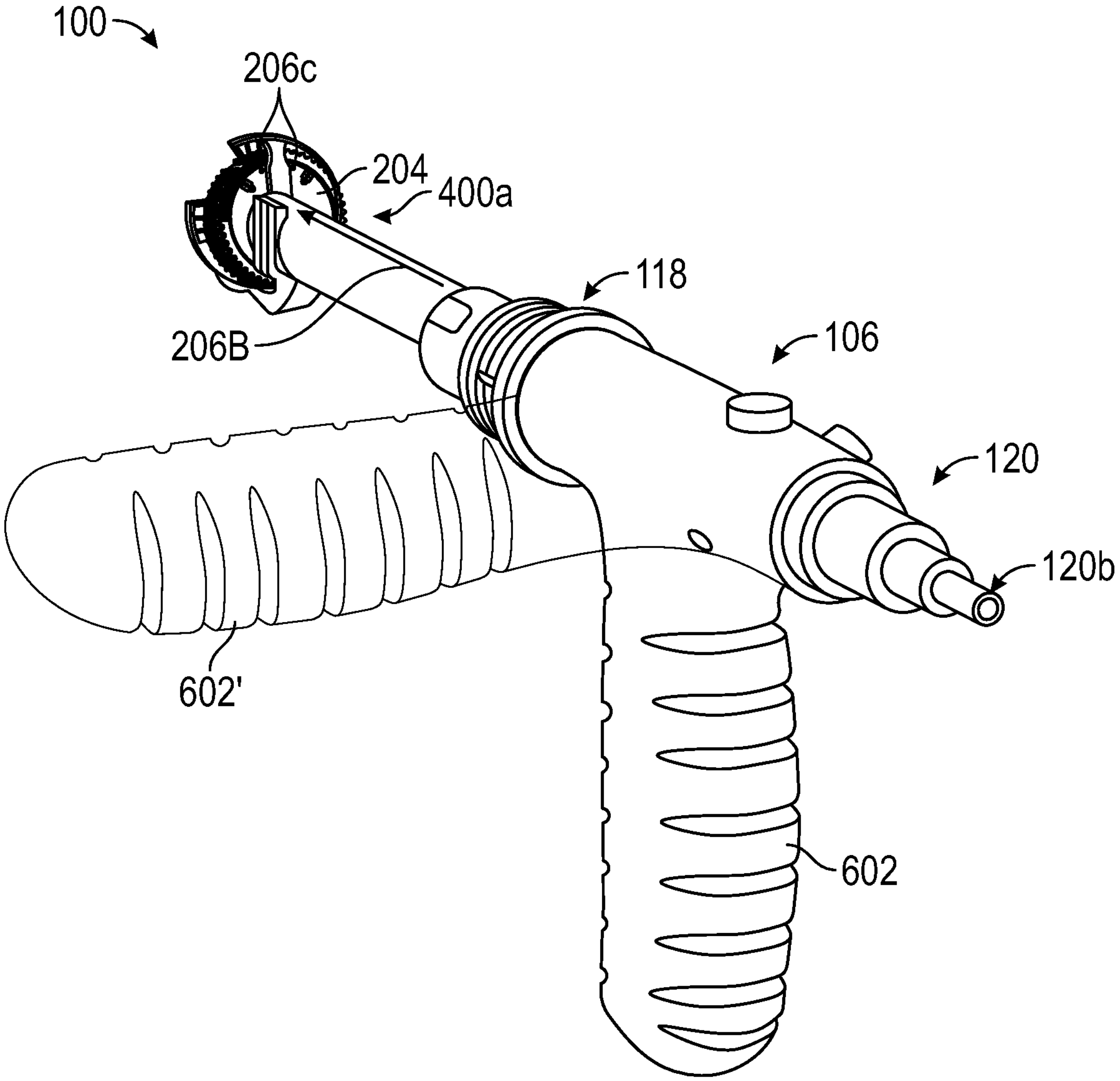
Figure 48:
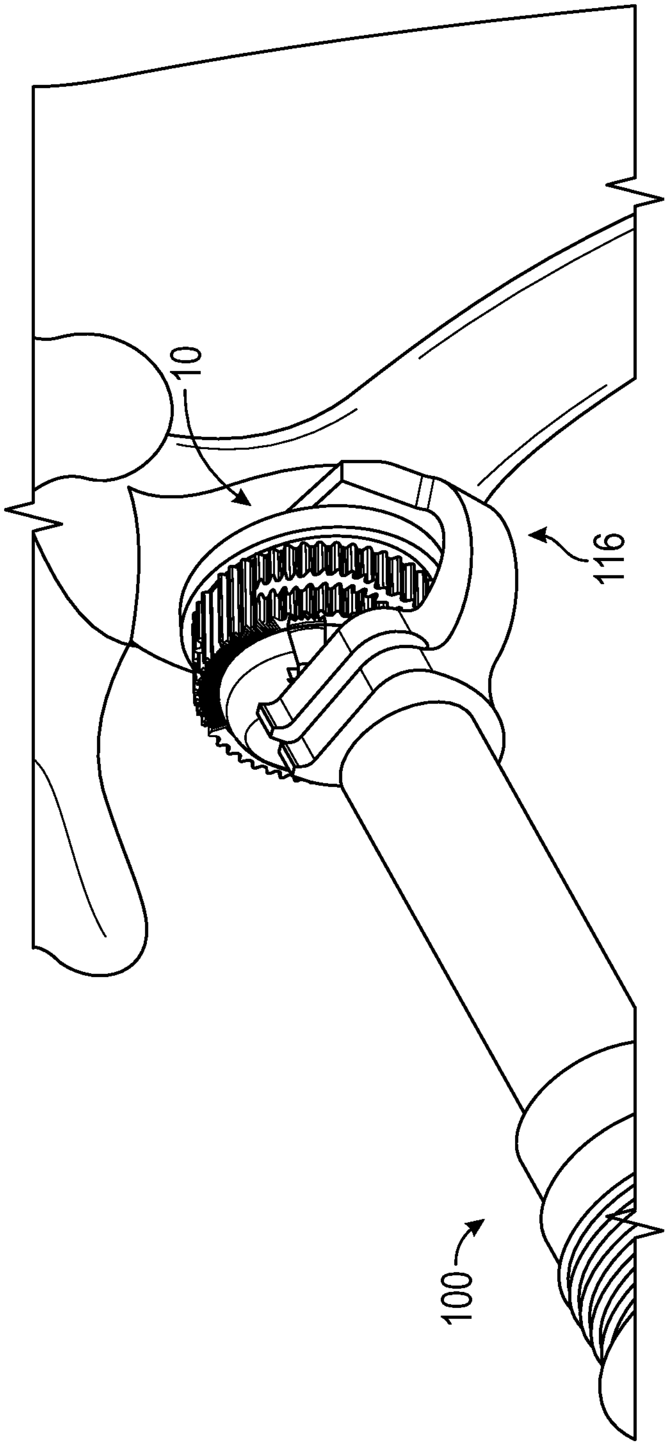
FIG. 48 illustrates one embodiment of an action of locating the reamer instrument of FIG. 1 at a bone surface to be reamed.
Figure 49:
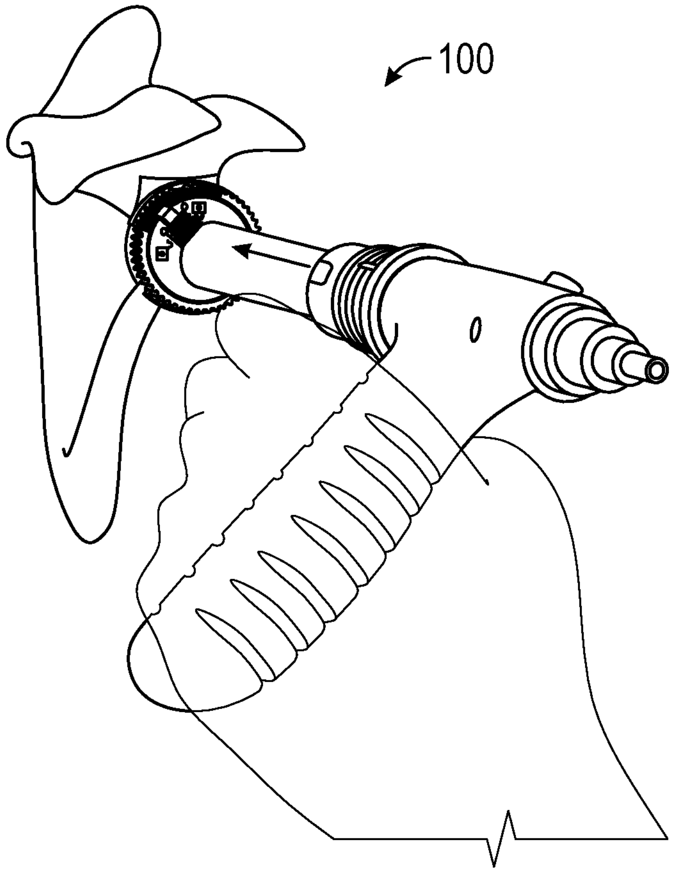
FIG. 49 illustrates one embodiment of an action of reaming bone with the reamer instrument of FIG. 1.

The drill connection 120 can be connected to a power source (not shown), for example by connecting the second end 120*b* of the drill connection 120 to the source. As discussed above, the handle 106 can be moved between one or more positions relative to the housing 106. If needed, the orientation of the handle 106 and the housing 108 can be adjusted prior to applying power to the instrument 100 to cut into bone. For example, as shown in FIG. 47, the handle 106 can be in a first position with the grip 602 in a first position, a 6 o'clock position in FIG. 47. The release collar 118 can be retracted to the unlocked position and the handle 106 can be rotated approximately 90-degrees relative to the housing 108 to a second position, for example a 9 o'clock position in FIG. 47 illustrated by the grip in phantom at 602'. The release collar 118 can be returned to its resting position and can lock the handle 106 relative to the housing 108 prior to supplying power to the drive shaft 104. Other positional adjustments are also possible, not just based on 90-degree increments. The present disclosure contemplates and can permit more variable adjustment, i.e., less than 90-degree increments with more than four positions across a 360-degree rotation circumference.

The assembled reamer instrument 100 connected to the power source, i.e., a drill, can be inserted over a central guide pin previously placed at the site of the bone surface to be prepared to receive an implant, i.e., the glenoid. The guide pin 404 of the depth stop 116 can be positioned in a pilot hole previously prepared in the bone surface 10 to be reamed (see FIG. 49). The drill can be held steady and the handle 106 of the reamer instrument 100 can be rotated to position the instrument in a desired orientation to prepare the bone surface. Markings on the reamer instrument 100 can aid in achieving proper orientation. For example, the arrow **206*b* can extend along an outer surface of the housing 108 and can indicate the area of maximum wedge preparation. The arrow 206*b* can point to two dots 206*c* on the top 204*a* of the housing reamer attachment 204, which can correspond to two dots on a face of an implant and a sizer (not shown) to be used during the procedure. The schematic marking 206*a* on the housing 108 can indicate the orientation of the reamer head 110 and the type of cut to be performed. The power source can drive the reamer instrument 100 at a low speed prior to the reamer head 110 engaging the bone surface 10 (see FIG. 49). The user can hold the grip 602 of the handle 106 while power is supplied to the reamer instrument 100 to drive the drive shaft 104 and, accordingly, rotate the reamer head 110 to ream or cut the bone surface 10. Holding the grip 602 can provide counter-torque to the drill and can maintain proper alignment of the reamer head 110 relative to the bone surface 10. The bone surface 10 can be adequately prepared to receive a half-wedge implant when the outer surface 4000 of the depth stop guard end 400*b* contacts the bone surface 10. The reamer instrument 100 can be moved away from the bone surface 10** by sliding the reamer instrument proximally off the central guide pin (not shown).

One skilled in the art will appreciate the steps necessary to disassemble the reamer instrument 100 in view of the embodiment of a method of assembly described herein. Briefly, the reamer instrument 100 can be disconnected from the power source, e.g., by removing the second end **120*b* of the drill connection 120 from the power source. The release button 605 can be depressed into the tubular body 600 of the handle. With the release button 605 depressed, the notch 605*n* can move distally and disengage from the groove 120*g* in the drill connection 120. The drill connection can be removed proximally from the proximal end of the handle 106. The release collar 118 can be retracted to the unlocked position. The housing 108 and drive shaft 104 can be removed distally from the handle 106. As discussed herein, in some embodiments, the drive tip 102 and reamer head 110 can be disposable single-use components of the reamer instrument 100. The remaining components of the reamer instrument 100** can be sterilized and safely packaged for repeated use.

While the steps of assembly, use, and disassembly described above were largely in connection with use of the half-wedge housing 108 for preparing the bone surface 10 to receive an implant with a first geometry, e.g., a half-wedge metaglene implant, one skilled in the art will appreciate how these steps can be applicable to and performed with the full-wedge housing 108', as well as other housing variations provided for herein or otherwise derivable from the present disclosures. Accordingly, description of such steps and procedures is omitted here for the sake of brevity.

Figure 50:
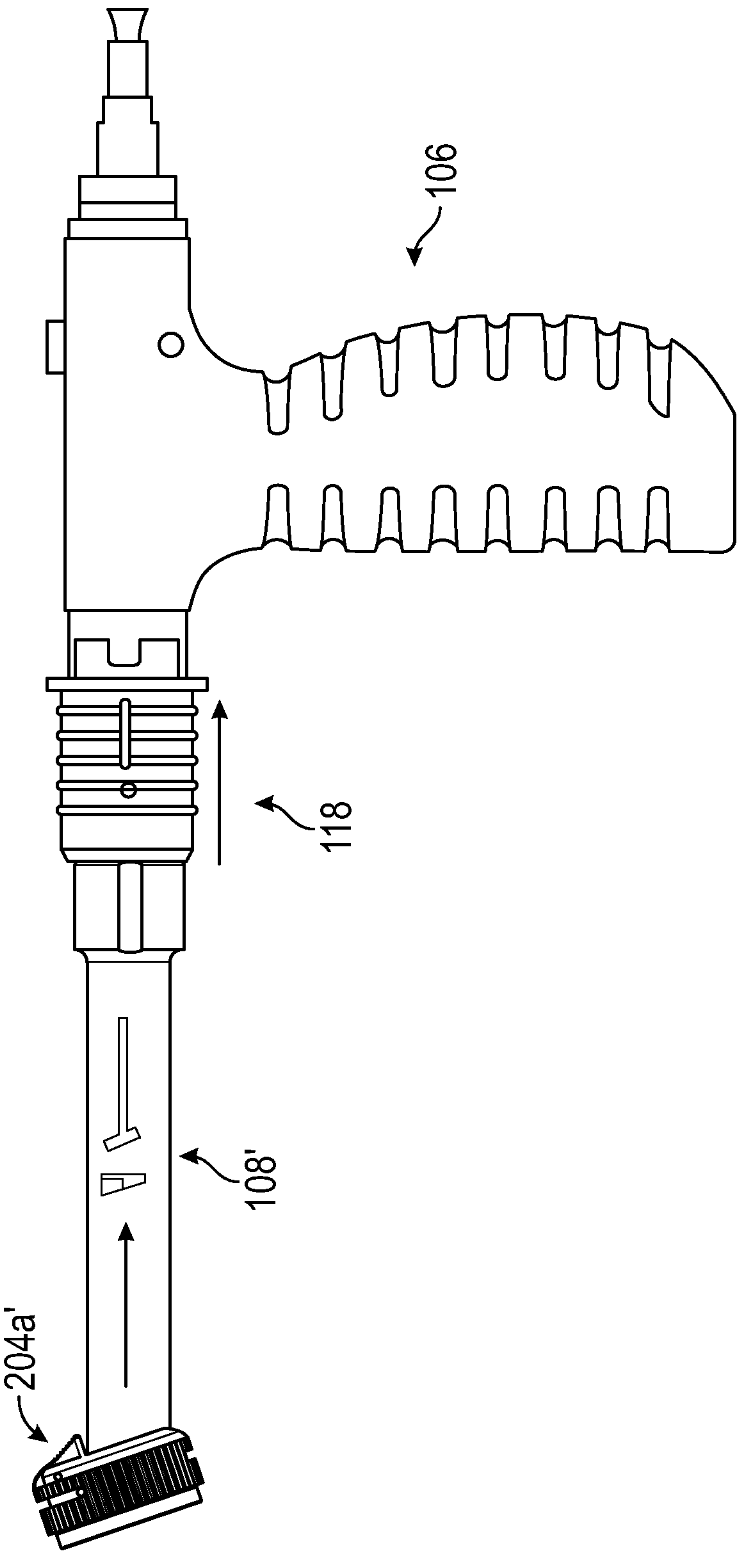
FIG. 50 illustrates one embodiment of an action of assembling the full-wedge housing of FIG. 31 to a reamer instrument in accordance with the present disclosure.
Figure 51:
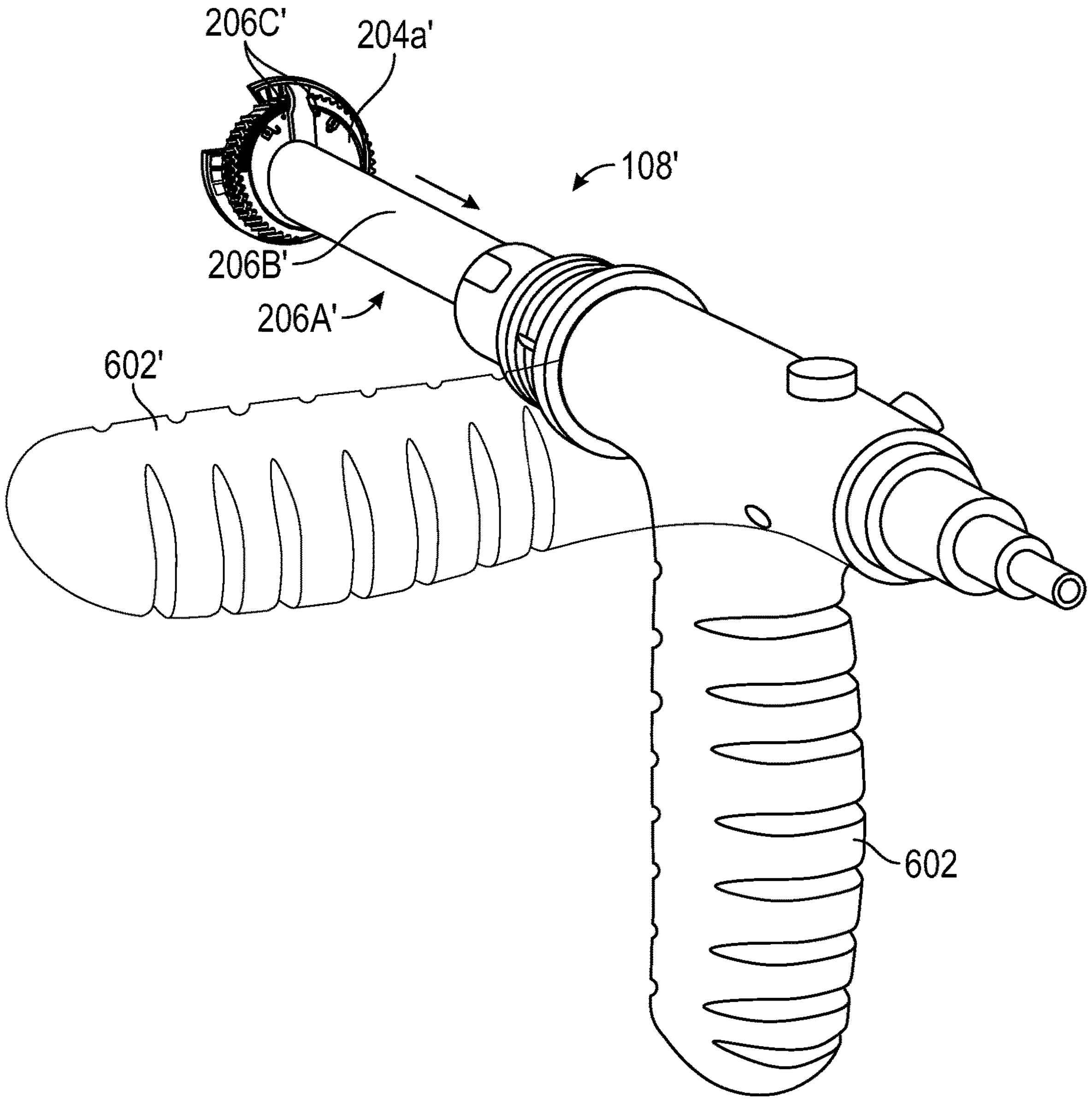
FIG. 51 illustrates one embodiment of an action of re-positioning a handle with respect to the full-wedge housing of the reamer instrument of FIG. 50.
Figure 52:
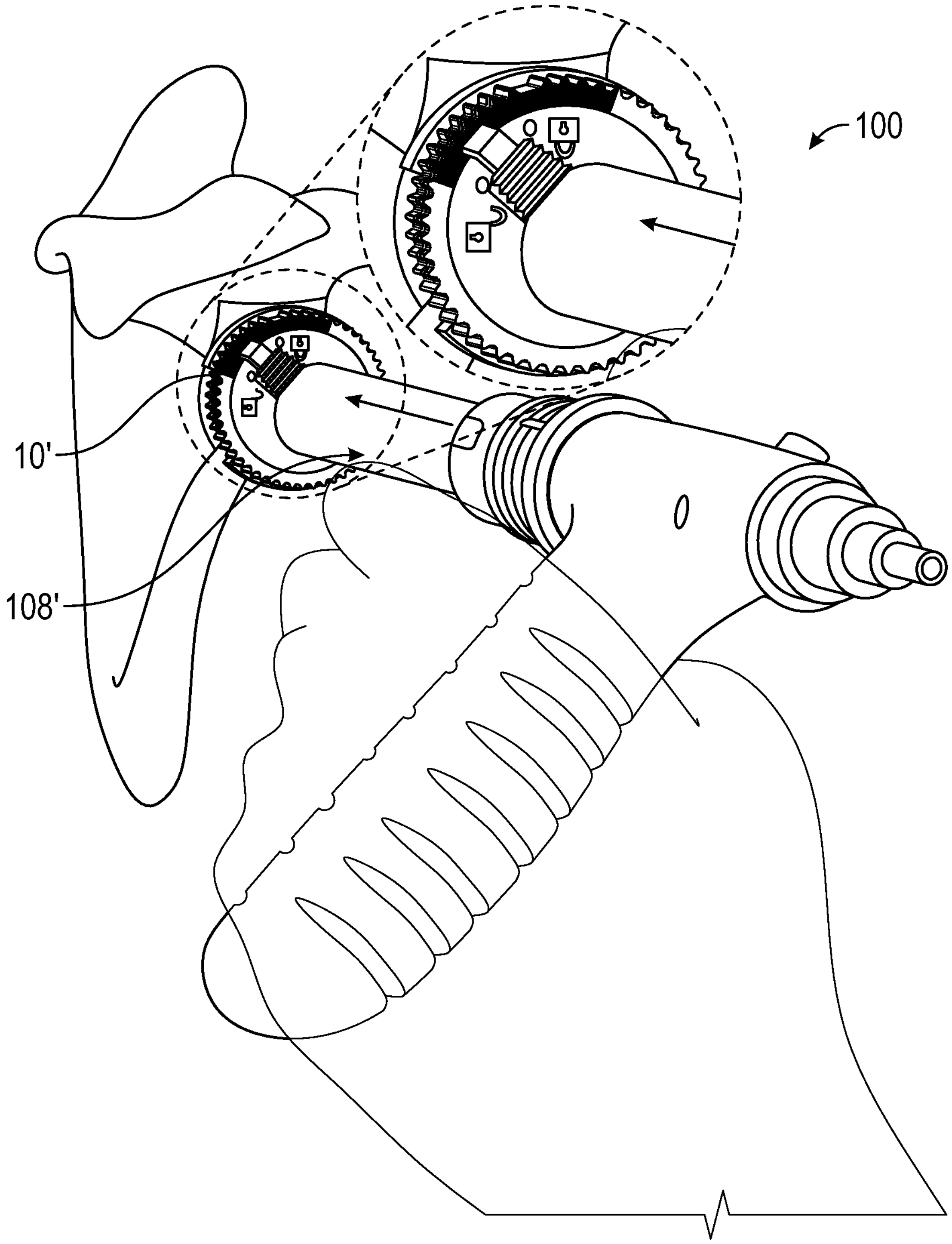
FIG. 52 illustrates one embodiment of an action of reaming bone with the reamer instrument of FIG. 50.

Briefly, and as illustrated in FIG. 50, the full-wedge housing 108' can coupled to the handle 106 by inserting the proximal end of the housing 108' into the distal end of the handle **106*d*. The release collar 118 can be retracted to its unlocked position to enable insertion of the housing 108' into the handle 106. The release collar 118 can be released to return to its resting or locked position to restrict axial and/or rotational movement between the handle 106 and the housing 108'. The arrow 206*b*' can extend along an outer surface of the housing 108' and can indicate the area of maximum wedge preparation. The arrow 206*b*' can point to two dots 206*c*' on the top 204*a*' of the housing reamer attachment 204' that can correspond to two dots on a face of an implant and a sizer (not shown) to be used during the procedure. FIG. 52 and the detailed view in circle inset A show one example of the dots 206*c*' and arrow 206*b*' in alignment with a maximum wedge location, which can correspond to a maximum defect location. The schematic marking 206*a*' on the housing 108' can indicate the orientation of the reamer head 110 and the type of cut to be performed. The handle 106 can be adjusted to the desired position, as shown, for example, in FIG. 51 by the grip 602 in phantom at 602'. The assembled reamer instrument 100 with the full-wedge housing 108' can be connected to a power source (not shown) and slide over a central guide pin previously placed at the bone surface 10'** to be reamed. The reamer instrument can be removed from the reaming site and disassembled, as described above.

Additional Embodiments of Reamer Instruments of the Present Disclosure

Figure 53:
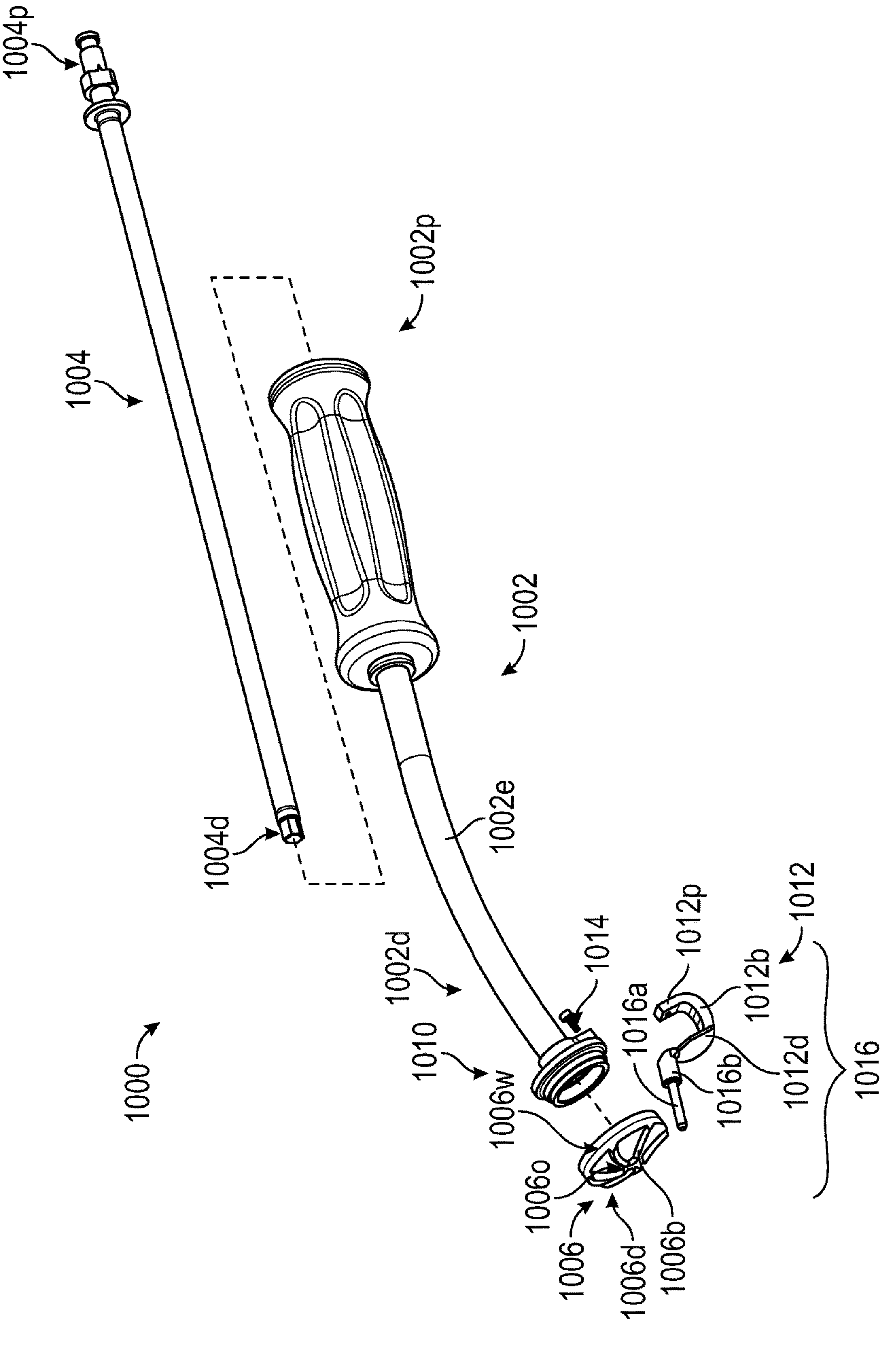
FIG. 53 is an exploded view of another embodiment of a reamer instrument in accordance with the present disclosure, the reamer instrument having a flexible drive shaft.
Figure 54:
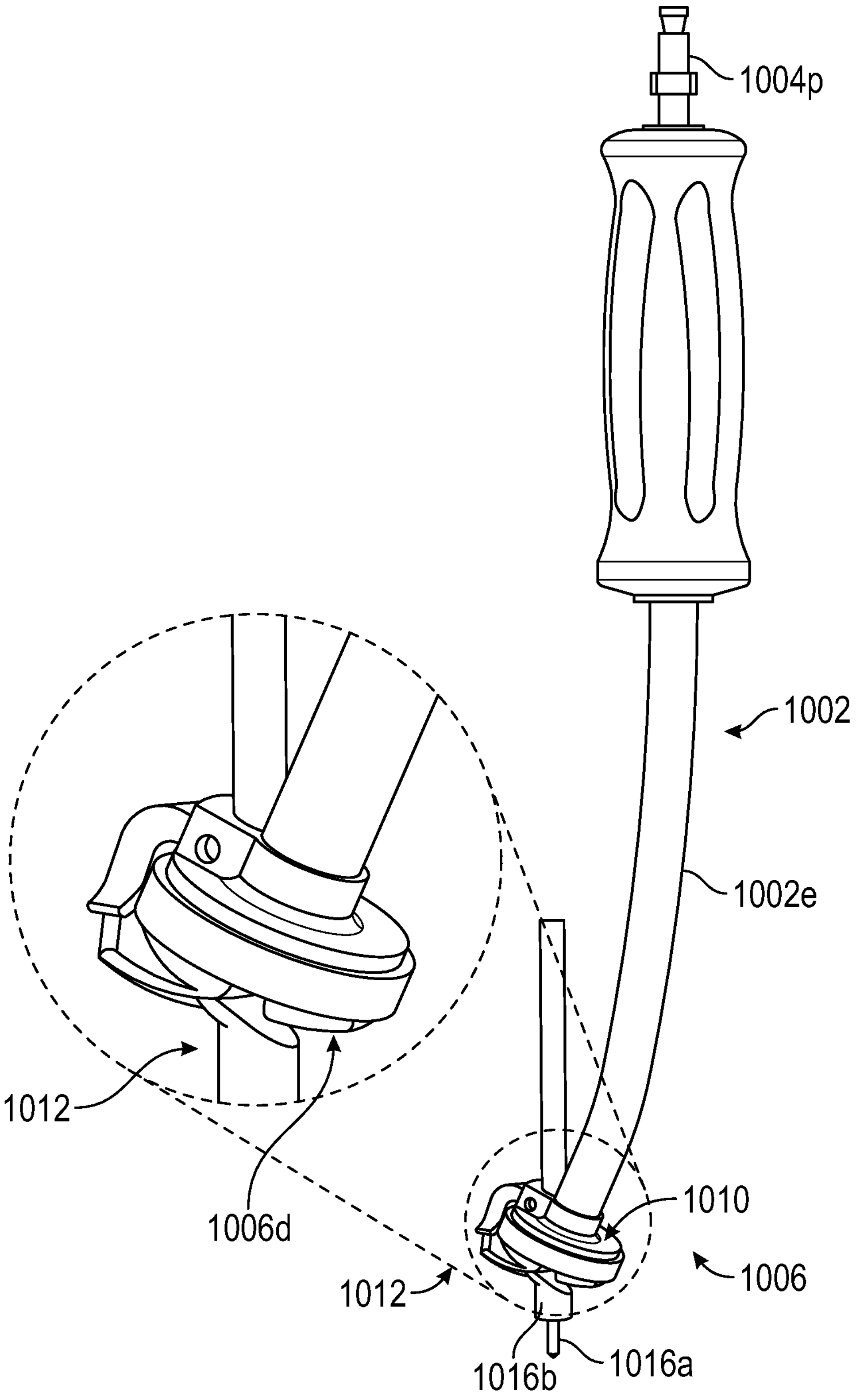
FIG. 54 is an assembled view of the reamer instrument of FIG. 53.
Figure 55:
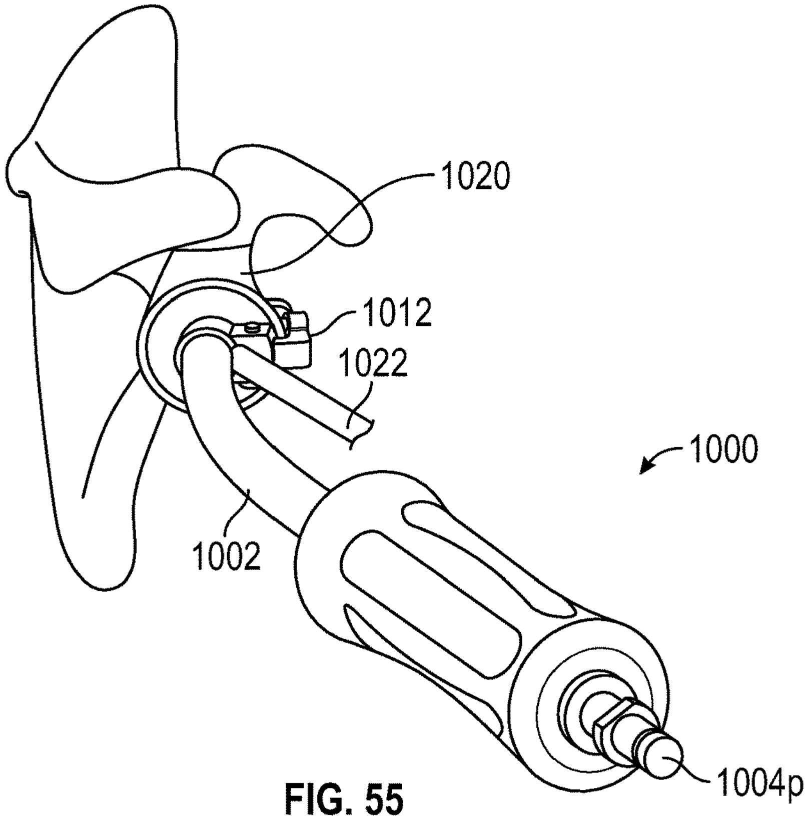
FIG. 55 illustrates one embodiment of an action of reaming bone using the reamer instrument of FIG. 53.
Figure 56:
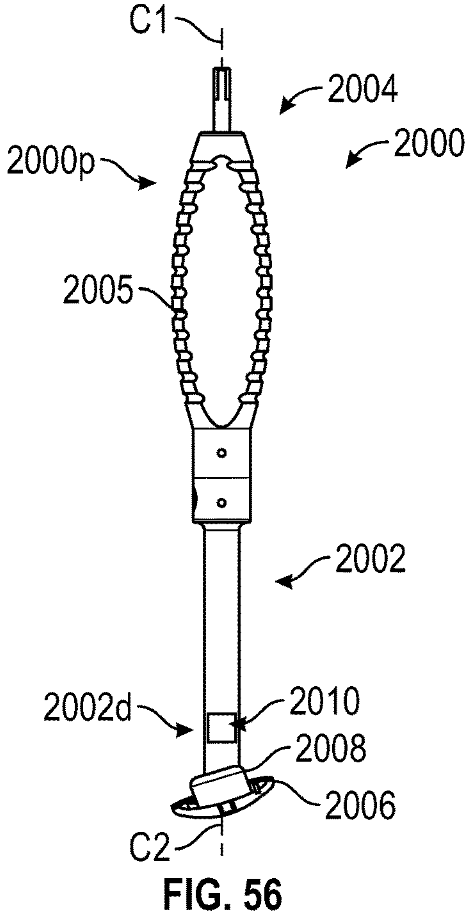
FIG. 56 is a side view of another embodiment of a reamer instrument in accordance with the present disclosure.

Another embodiment of a reamer instrument 1000 of the present disclosure is shown in FIGS. 53-55. The reamer instrument 1000 includes a flexible connection between an outer housing assembly and a handle. In some embodiments, the reamer instrument can be used without a guidewire for placement. Accordingly, in some embodiments, the reamer instrument 1000 need include a cannulated drive shaft. FIG. 53 shows an exploded view of the reamer instrument 1000, which can include a housing 1002, a drive shaft 1004, and a reamer head 1006. A proximal end **1002*p* of the housing 1002 can form a handle of the instrument 1000. For example, a grip 1008 can be located at the proximal end 1000*p* of the housing 1002 that can assist a user in holding the instrument. A distal end 1002*d* of the housing 1002 can have a reamer attachment 1010 that can securely couple to the reamer head 1006. A lumen or throughbore 10021 can extend from the proximal end 1002*p* to the distal end 1002*d* of the housing 1002. The housing 1002 can have an elongate body portion 1002*e* that can extend distally from the grip 1008 in a non-linear manner. For example, as can be seen in FIGS. 53 and 54, the elongate body 1002*e* can have a curvature such that the distal end 1002*d* of the housing 1002 and the proximal end 1002*p* of the housing 1002** are not axially aligned.

The drive shaft 1004 can have a proximal end **1004*p* that can couple to a power source, such as a drill and/or motor, to rotate the drive shaft 1004 under power. As shown, the drive shaft is solid, but in other embodiments, it can be cannulated. Thus, while a benefit of the present design is no guidewire is required, the reamer instrument 1000 can be designed to be used in conjunction with a guide wire, for instance by providing a cannulated drive shaft 1004. The drive shaft 1004 can be inserted into the housing 1002 and extend through the throughbore 10021 of the housing 1002. A distal end 1004***d* of the drive shaft (also referred to as a drive tip) can extend into the reamer attachment 1010. The drive shaft 1004 can be flexible, which can allow the drive shaft 1004 to follow or mimic a curvature of the housing 1002 to extend through the housing.

The reamer head 1006 can have a distal facing surface 1006*d* that can include a plurality of blades 1006*b* to cut or ream a bone surface. The reamer head 1006 can have a connecting portion 1006*c* extending proximally from the distal facing surface 1006*d*. The connecting portion 1006*c* can be designed to securely couple to the reamer attachment 1010 on the distal end 1002*d* of the housing 1002. For example, the connecting portion 1006*c* can include a snap ring that can compress over an inner lip 10101 of the reamer attachment and expand upon alignment with a groove in the reamer attachment 1010. An engagement aperture 10060 can extend through the reamer head 1006. With the reamer head 1006 securely coupled to the reamer attachment 1010, the distal facing surface 1006*d* can extend distally from the housing 1002 and the distal end 1004*d* of the drive shaft 1004 can be received within the engagement aperture 10060 to drive the reamer head 1006. For example, the distal end 1004*d* of the drive shaft 1004 can have a male hex drive feature. The engagement aperture 10060 of the reamer head 1006 can be a female hex drive feature or opening. The drive shaft 1004 can curve or bend with the curvature of the housing 1002 such that the drive tip 1004*d* can axially align with the engagement aperture 10060.

A depth stop 1012 can be coupled to the distal end 1002*d* of the housing 1002. At least a portion of the depth stop 1012 can extend between the distal cutting surface 1006*d* of the reamer head 1006 and a bone surface to prevent the reamer head 1006 from reaming bone at that particular location (see, e.g., the enlarged partial view of the instrument 1000 in the inset B in FIG. 54). The depth stop 1012 can have a generally C-shaped body 1012*b*. A set screw 1014 can couple a proximal arm 1012*p* of the depth stop 1012 to the distal end 1002*d* of the housing 1002. A guide pin 1016 can extend from a distal arm 1012*d* of the depth stop. The guide pin 1016 can have a first cylindrical portion 1016*a* and a second cylindrical portion 1016*b* located proximally of the first cylindrical portion. The first cylindrical portion 1016*a* can have a diameter smaller than a diameter of the second cylindrical portion 1016*b*. In this manner, the first cylindrical portion 1016*a* can engage a guide wire hole that can be drilled into a bone surface to be reamed. The second cylindrical portion 1016*b* can engage a hole drilled into a bone surface to be reamed that has a larger diameter than a guide wire hole that can be drilled into bone by a surgeon.

In use, a post hole can be drilled into a bone surface 1020 with a diameter that can be similar to a diameter of the second cylindrical portion 1016*b* of the guide pin 1012. In some embodiments, the post hole can be drilled at a location that can overlap with a previously drilled guide wire hole or a guide wire hole can be drilled after the post hole at an overlapping location. In some embodiments, the post hole can have a diameter smaller than a post of an implant to be received by the bone surface 1020. The drive shaft 1004 can be inserted through the throughbore 10021 of the housing 1002 and the reamer 1006 can be coupled to the reamer attachment portion 1010 of the housing 1002. The depth stop 1012 can be coupled to the distal end of the housing 1002*d*, e.g., to the reamer attachment 1010, and the proximal end 1004*p* of the drive shaft 1004 can be coupled to a power source. The first cylindrical portion 1016*a* of the depth stop guide post 1016 can be placed into the guide wire hole and/or the second cylindrical portion 1016*b* of the depth stop guide post 1016 can be placed into the post hole. In some embodiments, a vertical alignment tube 1022 can be secured to the distal end 1002*d* of the housing. The vertical alignment tube 1022 can serve as a visual axial guide for a surgeon. The vertical alignment tube 1022 can be cannulated such that a guide wire can be inserted into the tube 1022 and extend proximally from the housing 1022 at a trajectory that will align with a post of an implant to be received by the bone surface 1020. In this manner, the vertical alignment tube 1022 can provide a reference trajectory to a user in instances in which a guide wire is not used to place the reamer instrument 1000. The drive shaft 1004 can be driven by the power supply to rotate the reamer head 1006 and prepare the bone surface 1020.

FIG. 5659 illustrate another embodiment of a reamer instrument 2000 in accordance with the present disclosure. The reamer instrument 2000 can be a cannulated reamer with a housing 2002, a drive shaft 2004, and a reamer head 2006. The housing 2002 can have a proximal end 2002*p*, a distal end 2002*d*, and a lumen or throughbore (not visible) extending therebetween. The proximal end 2002*p* of the housing 2002 can form a handle 2005 for the instrument 2000. The drive shaft 2004 can extend through the housing throughbore. A proximal end 2004*p* of the drive shaft can be coupled to a power source (not shown) to rotate the drive shaft under power. The distal end 2002*d* of the housing 2002 can form a reamer attachment 2008 that can couple the reamer head 2006 to the housing 2002. The reamer attachment 2008 and the reamer head 2006 can have any of the features described herein in connection with various other embodiments of reamer attachments and reamer heads.

The housing 2002 and handle 2005 can extend along a longitudinal axis C1 from the proximal end of the housing 2002*p* to the distal end of the housing 2002*d*. The drive shaft 2004 can extend co-axially with the housing 2002 along the longitudinal axis C1. The reamer attachment 2008 can have a longitudinal axis C2 that can extend longitudinally through a bore (not visible) formed therein. The longitudinal axis C2 of the reamer attachment 2008 can extend at an oblique angle relative to the longitudinal axis C1 of the housing 2002. In this manner the distal end 2004*d* of the drive shaft 2004 can extend into the bore of the reamer attachment 2008 off-axis or obliquely relative the longitudinal axis C2 of the reamer attachment 2008. Accordingly, the distal end of the drive shaft 2004*d* can extend into an engagement aperture of the reamer head 2006 at an oblique angle and can engage with one or more drive features of the reamer head 2006 to drive the reamer head, as discussed herein.

Figure 58:
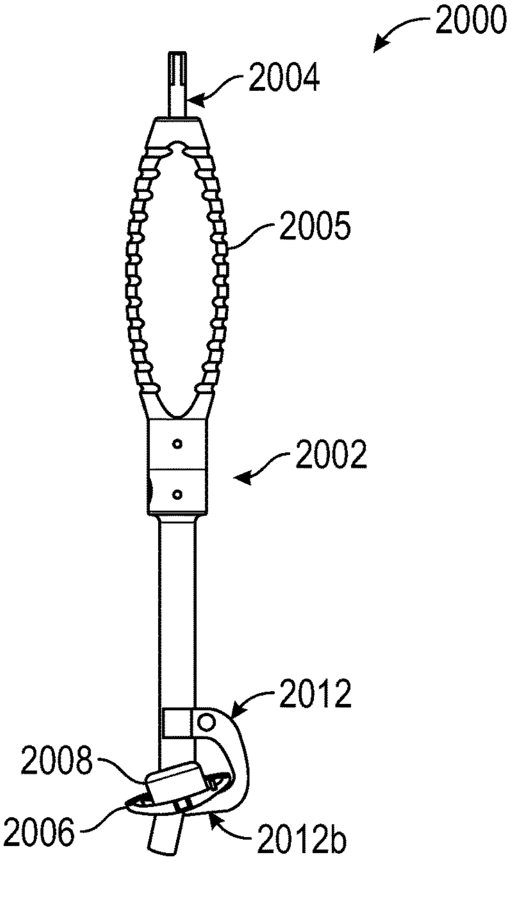
FIG. 58 illustrates the reamer instrument of FIG. 56 with a depth stop coupled thereto.
Figure 59:
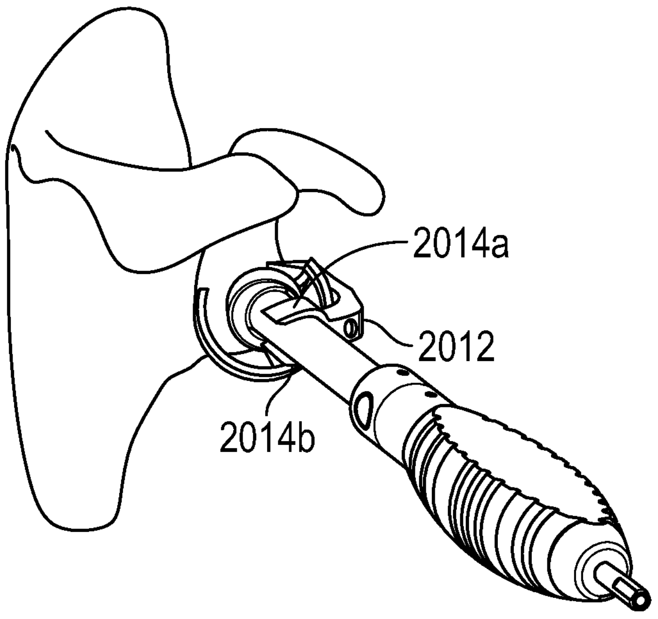
FIG. 59 illustrates one embodiment of an action of reaming bone using the reamer of FIG. 58.

The housing 2002 can have a depth stop attachment 2010 that can securely couple to a depth stop 2012 (see FIGS. 58 and 59). In some embodiments, the depth stop attachment 2010 can include a pair of recessed flats or cutaways 2010*a*, 2010*b* that can have a geometry and size complementary to an attachment feature 2014 of the depth stop. For example, similar to the depth stop 116 described above, the depth stop 2014 can have a pair of spaced apart arms 2014*a*, 2014*b* that can each couple with one of the cutaways 2010*a*, 2010*b* of the depth stop attachment 2010. With the depth stop 2012 coupled to the housing 2002 at the depth stop attachment 2010, a stop guard end 2012*b* can extend distally of a portion of the reamer head 2006 such that the stop guard end 2012*b* can extend between the portion of the reamer head 2006 and a bone surface during operation of the reamer instrument 2000. The depth stop 2012 can thus prevent a portion of the bone surface from being reamed or cut by the reamer head 2006, which can achieve a desired bone surface geometry, e.g., to receive a half-wedge implant.

Figure 57:
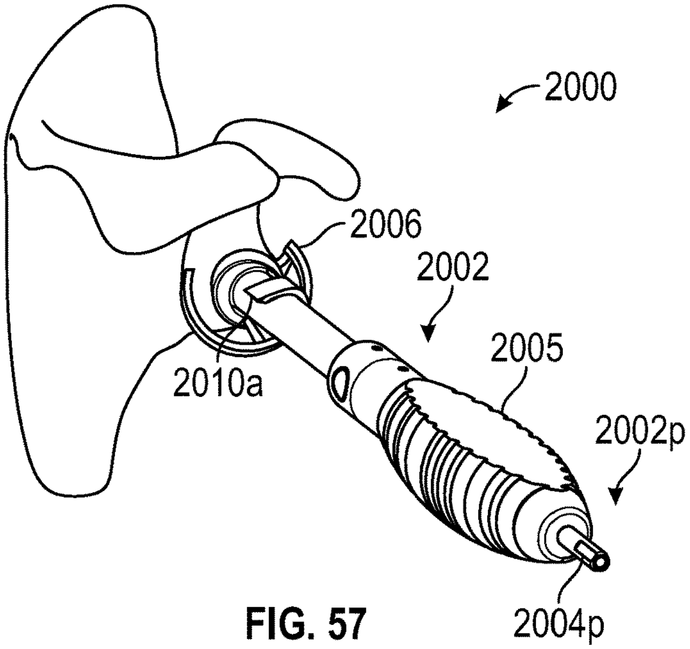
FIG. 57 illustrates one embodiment of an action of reaming bone using the reamer instrument of FIG. 56.

The reamer instrument 2000 can be used with or without the depth stop 2012 coupled thereto, depending upon the particular needs of a surgical procedure. In instances in which the depth stop 2012 is not needed to achieve a desired geometric profile of a bone surface, e.g., when preparing a bone to receive a full-wedge implant, the reamer instrument 2000 can ream bone without the depth stop 2012 coupled to the depth stop attachment (see FIG. 57). In other instances, the depth stop 2012 can be coupled to the housing 2002 at the depth stop attachment location 2010 prior to reaming bone such that a portion of the depth stop 2012 extends between the reamer head 2006 and a bone surface during use.

As discussed herein, at least some portion of the instruments disclosed herein can be designed to be disposed of after a single use, and/or at least some portion of the instruments can be designed to be used multiple times. In either case, however, the instrument can be reconditioned for reuse after at least one use. Reconditioning can include any combination of the steps of disassembly of the instrument, followed by cleaning or replacement of particular pieces, and subsequent reassembly. In particular, the instrument can be disassembled, and any number of the particular pieces or parts of the instrument can be selectively replaced or removed in any combination. Upon cleaning and/or replacement of particular parts, the instrument can be reassembled for subsequent use either at a reconditioning facility, or by a surgical team immediately prior to a surgical procedure. Those skilled in the art will appreciate that reconditioning of an instrument can utilize a variety of techniques for disassembly, cleaning/replacement, and reassembly. Use of such techniques, and the resulting reconditioned instrument, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the instrument is sterilized. This can be done by any number of ways known to those skilled in the art including beta or gamma radiation, ethylene oxide, steam, and a liquid bath (e.g., cold soak).

One skilled in the art will appreciate further features and advantages of the disclosure based on the above-described embodiments. Accordingly, the disclosure is not to be limited by what has been particularly shown and described, except as indicated by the appended claims. All publications and references cited herein are expressly incorporated herein by reference in their entirety.

What is claimed is:

1. A method of assembling a surgical reamer, comprising:
- coupling a proximal end of a drive shaft to a distal end of a handle;
- coupling a proximal end of a housing attachment to the distal end of the handle such that the drive shaft extends through an inner throughbore of the housing attachment;
- coupling a reamer head to a distal end of the housing attachment by placing a locking collar at the distal end of the housing attachment in an unlocked position and inserting the reamer head into the distal end of the housing attachment; and
- releasably locking the reamer head to the distal end of the housing attachment such that a cutting surface of the reamer head extends distally form the housing attachment.

2. The method of claim 1, wherein coupling the proximal end of the housing attachment to the distal end of the handle further comprises:
- inserting the proximal end of the housing attachment into a release collar slidably disposed along the distal end of the handle; and
- orienting the housing attachment relative to the handle in one of a plurality of positions, each of the plurality of positions corresponding to a different rotational orientation of the housing attachment around a longitudinal axis of the handle.

3. The method of claim 2, wherein the plurality of positions correspond to rotational orientations of the housing attachment relative to the longitudinal axis of the handle at 90-degree intervals.

4. The method of claim 1, further comprising:
- assembling the drive shaft by coupling a disposable drive pin drive tip to a distal end of an elongate shaft.

5. The method of claim 1, wherein releasably locking the reamer head to the distal end of the housing attachment further comprises placing the locking collar in a locked position.

6. The method of claim 5, wherein placing the locking collar in a locked position further comprises rotating the locking collar relative to the housing attachment.

7. The method of claim 6, wherein rotating the locking collar relative to the housing attachment further comprises causing ball bearings located at the distal end of the housing attachment to slide along at last one ramp on an inner surface of the locking collar.

8. The method of claim 1, further comprising:
- coupling a depth-stop to a recessed portion formed in the housing attachment such that at least a portion of the depth-stop opposes the cutting surface of the reamer head.

9. The method of claim 1, further comprising:
- coupling at least one of a drill connection or an electrical connection to the handle to enable driving the drive shaft under power.

10. The method of claim 9, wherein the drill connection comprises a Hudson connection.

11. The method of claim 1, wherein the housing attachment is selected from a first housing attachment and a second housing attachment, with the first housing attachment being configured to dispose the reamer head coupled thereto at a first oblique angle relative to a longitudinal axis of the drive shaft, and the second housing attachment being configured to dispose the reamer head coupled thereto at a second oblique angle relative to the longitudinal axis of the drive shaft, the first and second oblique angles being different from each other and the first and second oblique angles being defined by an angle formed by a central longitudinal axis of the reamer head and the longitudinal axis of the drive shaft.

12. The method of claim 1, wherein a central longitudinal axis of the drive shaft extends at an oblique angle relative to a central longitudinal axis of the reamer head when the reamer head is coupled to the housing attachment, the housing attachment is coupled handle, and the drive shaft is also coupled to the handle and extends through the inner throughbore of the housing attachment.

13. The method of claim 1, further comprising coupling the reamer head to a distal end of the drive shaft.

14. The method of claim 13, wherein coupling the reamer head to a distal end of the drive shaft further comprises coupling a plurality of engagement pins located at the distal end of the drive shaft to a plurality of engagement posts of the reamer head.

15. The method of claim 14, wherein the plurality of engagement posts extend at least one of along or substantially parallel to a central longitudinal axis of the reamer head.

16. The method of claim 14, wherein the plurality of engagement pins extend substantially perpendicular to a central longitudinal axis of the drive shaft.

* * * * *